US010517944B2

(12) United States Patent
Bunnik et al.

(10) Patent No.: US 10,517,944 B2
(45) Date of Patent: Dec. 31, 2019

(54) THERAPEUTIC HPV VACCINE COMBINATIONS

(71) Applicants: Janssen Vaccines & Prevention B.V., Leiden (NL); Bavarian Nordic A/S, Kvistgaard (DK)

(72) Inventors: Evelien M. Bunnik, Mico, TX (US); Jerôme H. H. V. Custers, Alphen aan den Rijn (NL); Gerrit C. Scheper, Amstelveen (NL); Selina Khan, Leiden (NL); Markus Kalla, Penzberg (DE); Katrin Weidner, Regensburg (DE)

(73) Assignees: Janssen Vaccines & Prevention B.V., Leiden (NL); Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 16/098,303

(22) PCT Filed: May 1, 2017

(86) PCT No.: PCT/US2017/030338
§ 371 (c)(1),
(2) Date: Nov. 1, 2018

(87) PCT Pub. No.: WO2017/192418
PCT Pub. Date: Nov. 9, 2017

(65) Prior Publication Data
US 2019/0142933 A1 May 16, 2019

Related U.S. Application Data

(60) Provisional application No. 62/447,094, filed on Jan. 17, 2017, provisional application No. 62/330,562, filed on May 2, 2016.

(51) Int. Cl.
| | |
|---|---|
| *A61K 39/00* | (2006.01) |
| *C12N 7/00* | (2006.01) |
| *C12N 15/86* | (2006.01) |
| *C12N 7/02* | (2006.01) |
| *A61K 39/12* | (2006.01) |
| *A61K 39/295* | (2006.01) |
| *C07K 14/025* | (2006.01) |

(52) U.S. Cl.
CPC ............ *A61K 39/295* (2013.01); *A61K 39/12* (2013.01); *C07K 14/025* (2013.01); *A61K 2039/5256* (2013.01); *A61K 2039/53* (2013.01); *A61K 2039/585* (2013.01); *A61K 2039/70* (2013.01); *C12N 2710/20034* (2013.01); *C12N 2710/20071* (2013.01)

(58) Field of Classification Search
CPC ........ A61K 2300/00; A61K 2039/5256; C12N 2710/24143; C12N 7/00; C12N 15/86
See application file for complete search history.

(56) References Cited

U.S. PATENT DOCUMENTS

| | | |
|---|---|---|
| 5,057,540 A | 10/1991 | Kensil et al. |
| 5,122,458 A | 6/1992 | Post et al. |
| 5,385,839 A | 1/1995 | Stinski |
| 5,559,099 A | 9/1996 | Wickham et al. |
| 5,837,511 A | 11/1998 | Falck-Pedersen et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |
| 6,733,994 B2 | 5/2004 | Weiner et al. |
| 7,270,811 B2 | 9/2007 | Bout et al. |
| 8,932,607 B2 | 1/2015 | Custers et al. |
| 9,119,813 B2 | 9/2015 | Radosevic et al. |
| 9,125,870 B2 | 9/2015 | Radosevic et al. |
| 2007/0014810 A1 | 1/2007 | Baker et al. |
| 2013/0122038 A1 | 5/2013 | Radosevic et al. |
| 2015/0196632 A1 | 7/2015 | Radosevic et al. |
| 2015/0320854 A1 | 11/2015 | Radosevic et al. |
| 2016/0122396 A1 | 5/2016 | Bunnik et al. |
| 2017/0051019 A1 | 2/2017 | Bunnik et al. |

FOREIGN PATENT DOCUMENTS

| | | |
|---|---|---|
| EP | 1230354 B1 | 1/2004 |
| EP | 990041 B1 | 6/2006 |
| EP | 1385946 B1 | 12/2009 |
| EP | 1183368 B1 | 4/2012 |
| WO | 90003184 A1 | 4/1990 |
| WO | 9014837 A1 | 12/1990 |
| WO | 96/09378 A1 | 3/1996 |
| WO | 9611711 A1 | 4/1996 |

(Continued)

OTHER PUBLICATIONS

Van Der Burg et al., "Therapeutic vaccination against human papilloma virus induced malignancies," Current Opinion in Immunology, vol. 23, pp. 252-257 (2011).
Wieking et al., "A non-oncogenic HPV 16 E6/E7 vaccine enhances treatment of HPV expressing tumors," Cancer Gene Therapy, vol. 19, pp. 667-674 (2012).

(Continued)

*Primary Examiner* — Barry A Chestnut
(74) *Attorney, Agent, or Firm* — Panitch Schwarze Belisario & Nadel LLP

(57) ABSTRACT

Vectors, vaccines, vaccine compositions and vaccine combinations for use as therapeutics against HPV18 and/or HPV16 are described.

20 Claims, 29 Drawing Sheets

Specification includes a Sequence Listing.

(56) References Cited

FOREIGN PATENT DOCUMENTS

| | | |
|---|---|---|
| WO | 98/39411 A1 | 9/1998 |
| WO | 2000/70071 A1 | 11/2000 |
| WO | 2003/104467 A1 | 12/2003 |
| WO | 2004004762 A1 | 1/2004 |
| WO | 2005002620 A1 | 1/2005 |
| WO | 2005/080556 A2 | 9/2005 |
| WO | 2006048459 A2 | 5/2006 |
| WO | 2007073513 A2 | 6/2007 |
| WO | 2007/104792 A2 | 9/2007 |
| WO | 2007100908 A2 | 9/2007 |
| WO | 2009106362 A1 | 9/2009 |
| WO | 2010/060719 A1 | 6/2010 |
| WO | 2010073043 A1 | 7/2010 |
| WO | 2011/098592 A1 | 8/2011 |
| WO | 2013083287 A1 | 6/2013 |

OTHER PUBLICATIONS

Yan et al., "Induction of antitumor immunity in vivo following delivery of a novel HPV-16 DNA vaccine encoding an E6/E7 fusion antigen," Vaccine, vol. 27, pp. 431-440 (2009).

Yao et al., "A Novel Tetracycline-Inducible Viral Replication Switch," Human Gene Therapy, Mary Ann Liebert, Inc., vol. 10, pp. 419-427 (Feb. 10, 1999).

Yoshida et al., "Adenovirus-Mediated Inducible Gene Expression through Tetracycline-Controllable Transactivator with Nuclear Localization Signal," Biochemical and Biophysical Research Communications, vol. 230, pp. 426-430 (1997).

Yugawa et al., "Molecular mechanisms of cervical carcinogenesis by high-risk human papillomaviruses: novel functions of E6 and E7 oncoproteins," Rev. Med. Virol., vol. 19, pp. 97-113 (2009).

Zwaveling et al., "Established Human Papillomavirus Type 16-Expressing Tumors Are Effectively Eradicated Following Vaccination with Long Peptides," The Journal of Immunology, vol. 169, pp. 350-358 (2002).

Abbink et al., "Comparative Seroprevalence and Immunogenicity of Six Rare Serotype Recombinant Adenovirus Vaccine Vectors from Subgroups Band D," Journal of Virology, vol. 81, No. 9, pp. 4654-4663 (2007).

Brokaw et al., "Amino Acids Critical for the Functions of the Bovine Papillomavirus Type 1 E2 Transactivator, Journal of Virology," vol. 70, No. 1, pp. 23-29 (1996).

Cottingham et al., "Preventing Spontaneous Genetic Rearrangements in the Transgene Cassettes of Adenovirus Vectors," Biotechnology and Bioengineering, vol. 109, pp. 719-728 (2012).

Daayana et al., "Phase II trial of imiquimod and HPV therapeutic vaccination in patients with vulval intraepithelial neoplasia," British Journal of Cancer, vol. 102, pp. 1129-1136 (2010).

De Groot et al., "HIV vaccine development by computer assisted design: the GAIA vaccine," Vaccine, vol. 23, pp. 2136-2148 (2005).

De Jong et al., "Frequent Detection of Human Papillomavirus 16 E2-specific T-helper Immunity in Healthy Subjects," Cancer Research, vol. 62, pp. 472-479 (2002).

Edholm et al., Adenovirus Vector Designed for Expression of Toxic Proteins, Journal of Virology, vol. 75, No. 20, pp. 9579-584 (2001).

Evans et al., "Development of Stable Liquid Formulations for Adenovirus-Based Vaccines," Journal of Pharmaceutical Sciences, vol. 93, No. 10, pp. 2458-2475 (2004).

Fallaux et al., "New Helper Cells and Matched Early Region 1-Deleted Adenovirus Vectors Prevent Generation of Replication-Competent Adenoviruses," Human Gene Therapy, vol. 9, pp. 1909-1917 (1998).

Gao et al., "A Cell Line for High-Yield Production of E1-Deleted Adenovirus Vectors without the Emergence of Replication-Competent Virus," Human Gene Therapy, vol. 11, pp. 213-219 (2000).

Gilbert et al., "Establishment and validation of new complementing cells for production of E1-deleted adenovirus vectors in serum-free suspension culture," Journal of Virological Methods, vol. 208, pp. 177-188 (2014).

Hamid et al., "Anti-programmed death-1 and anti-programmed death-ligand 1 antibodies in cancer therapy," Expert Opinion on Biological Therapy, vol. 13, No. 6, pp. 847-861 (2013).

Havenga et al, "Novel replication-incompetent adenoviral B-group vectors: high vector stability and yield in PER.C6 cells," Journal of General Virology, vol. 87, pp. 2135-2143 (2006).

Hildesheim et al., "Effect of Human Papillomavirus 16/18 L1 Viruslike Particle Vaccine Among Young Women With Preexisting Infection: A Randomized Trial," Journal of American Medical Association, vol. 298, No. 7, pp. 743-753 (2007).

Lin et al., "Treatment of Established Tumors with a Novel Vaccine That Enhances Major Histocompatibility Class II Presentation of Tumor Antigen," Cancer Research, vol. 56, pp. 21-26 (1996).

Massimi et al., "Transformation Assays for HPV Oncoproteins," Methods in Molecular Medicine, vol. 119, pp. 381-395 (2005).

Matthews et al., "Development and use of a 293 cell line expressing lac repressor for the rescue of recombinant adenoviruses expressing high levels of rabies virus glycoprotein," Journal of General Virology, vol. 80, 345-353 (1999).

Mellman et al., "Cancer immunotherapy comes of age," Nature, vol. 480, No. 7378, pp. 480-489 (2011).

Mullick et al., "The cumate gene-switch: a system for regulated expression in mammalian cells," BMC Biotechnology, vol. 6, No. 43, 18 pages (2006).

Munger et al., "The E6 and E7 Genes of the Human Papillomavirus Type 16 Together Are Necessary and Sufficient for Transformation of Primary Human Keratinocytes," Journal of Virology, vol. 63, No. 10, pp. 4417-4421 (1989).

Ogun et al., "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (2008).

Oosterhuis et al., "DNA Vaccines and Intradermal Vaccination by DNA Tattooing," Current Topics Microbiology, 2010, 30 pages, Springer-Verlag Berlin Heidelberg.

Oosterhuis et al., "Preclinical development of highly effective and safe DNA vaccines directed against HPV 16 E6 and E7," International Journal of Cancer, vol. 129, pp. 397-406 (2011).

Hoganson et al., "Development of a Stable Adenoviral Vector Formulation," Bioprocessing Journal, pp. 43-48 (Mar. 2002).

Hoof et al., "NetMHCpan, a method for MHC class I binding prediction beyond humans," Immunogenetics, vol. 61, No. 1, pp. 1-13 (2009).

Horwitz, Marshall S., Adenoviruses, Fields Virology, Third Edition, Chapter 68, pp. 2149-2171 (1996).

Kenter et al., "Vaccination against HPV-16 Oncoproteins for Vulvar Intraepithelial Neoplasia," The New England Journal of Medicine, vol. 361, pp. 1838-1847 (2009).

Kovesdi et al., "Adenoviral Producer Cells," Viruses, vol. 2, pp. 1681-1703 (2010).

Peters et al., "Examining the independent binding assumption for binding of peptide epitopes to MHC-1 molecules," Bioinformatics, vol. 19, No. 14, pp. 1765-1772 (2003).

Rubinchik et al., "Adenoviral vector which delivers FasL-GFP fusion protein regulated by the tet-inducible expression system," Gene Therapy, vol. 7, pp. 875-885 (2000).

Sakai et al., "Targeted Mutagenesis of the Human Papillomavirus Type 16 E2 Transactivation Domain Reveals Separable Transcriptional Activation and DNA Replication Functions," Journal of Virology, vol. 70, No. 3, pp. 1602-1611 (1996).

Sambrook et al., "Molecular Cloning, A Laboratory Manual," Second Edition with table of contents, 32 pages (1989).

Sedman et al., "The Full-Length E6 Protein of Human Papillomavirus Type 16 Has Transforming and trans-Activating Activities and Cooperates with E7 to Immortalize Keratinocytes in Culture," Journal of Virology, vol. 65, No. 9, pp. 4860-4866 (1991).

Smahel et al., Modified HPV16 E7 Genes as DNA Vaccine against E7-Containing Oncogenic Cells, Virology, vol. 281, pp. 231-238 (2001).

GenBank: ACI43214.1. HPV-16 E6/E7 fusion protein [synthetic construct]. Dated Jan. 14, 2009.

(56) References Cited

OTHER PUBLICATIONS

Mishra et al., "Dendritic Cell-Mediated, DNA-Based Vaccination against Hepatitis C Induces the Multi-Epitope-Specific Response of Humanized, HLA Transgenic Mice," PLOS, vol. 9, No. 8, 8 pages (2014).

Moise et al., "VennVax, a DNA-prime, peptide-boost multi-I-cell epitope poxvirus vaccine, induces protective immunity against vaccinia infection by T cell response alone," Vaccine, vol. 29, pp. 501-511 (2011).

Moss et al., "HelicoVax: Epitope-based therapeutic Helicobacter pylori vaccination in a mouse model," Vaccine, vol. 29, pp. 2085-2091 (2011).

Ohlshlager, et al., "An improved rearranged Human Papillomavirus Type 16 E7 DNA vaccine candidate (HPV-16 E7SH) induces an E7 wildtype-specific T cell response," Vaccine, vol. 24, pp. 2880-2893 (2006).

Brandsma et al., "Therapeutic vaccination of rabbits with a ubiquitin-fused papillomavirus E1, E2, E6 and E7 DNA vaccine," Vaccine, vol. 25, 6158-6163 (2007).

Almajhdi et al., "Design of a Highly Effective Therapeutic HPV16 E6/E7-Specific DNA Vaccine: Optimization by Different Ways of Sequence Rearrangements (Shuffling)," PLOS One, vol. 9, No. 11, 15 pages (2014).

Hienken et al., "Preclinical safety evaluation of DNA vaccines encoding modified HPV16 E6 and E7," Vaccine, vol. 30, pp. 4259-4266 (2012).

Oosterhuis et al., "Rational design of DNA vaccines for the induction of HPV16 E6 and E7 specific cytotoxic T cell responses," Human Gene Therapy, Mary Ann Liebert, Inc., pp. 1-42 (2012).

Prakash et al., "Amino acids necessary for DNA contact and dimerization imply novel motifs in the papillomavirus E2 transactivator," Genes & Development, Cold Spring Harbor Laboratory Press, vol. 6, pp. 105-116 (1992).

Lundegaard et al., "NetMHC-3.0: accurate web accessible predictions of human, mouse and monkey MHC class I affinities for peptides of length 8-11," Nucleic Acids Research, vol. 36, pp. W509-W512, vol. 36, web server issue (May 7, 2008).

Kim et al., "Clearance of persistent HPV infection and cervical lesion by therapeutic DNA vaccine in CIN 3 patients," Nature Communications, Macmillan Publishers Limited, pp. 1-14 (Oct. 30, 2014).

Zhang et al., "Immune epitope database analysis resource (IEBD-AR)," Nucleic Acids Research, vol. 36, pp. W513-W518 (2008).

Moscicki, "HPV Vaccines: Today and in the Future," Journal of Adolescent Health, vol. 43, pp. S26-S40 (2008).

Int'l Search Report and Written Opinion dated Oct. 27, 2016 in Int'l Application No. PCT/EP2016/069618.

Int'l Search Report and Written Opinion dated Feb. 23, 2016 in Int'l Application No. PCT/EP2015/075516.

SIPO et al., "An improved Tet-On regulatable FasL-adenovirus vector system for lung cancer therapy," Journal of Molecular Medicine, vol. 84, pp. 215-225 (2006).

Radosevic et al., "The Th1 Immune Response to Plasmodium falciparum Circumsporozoite Protein Is Boosted by Adenovirus Vectors 35 and 26 with a Homologous Insert," Clinical and Vaccine Immunology,—vol. 17, No. 11, pp. 1687-1694 (2010).

He et al., "Viral Recombinant Vaccines to the E6 and E7 Antigens of HPV-16," Virology, vol. 270, pp. 146-161 (2000).

Tatsis et al., "Adenoviruses as Vaccine Vectors," Molecular Therapy, vol. 10, No. 4, pp. 616-629 (Oct. 2004).

Livingston et al., "A Rational Strategy to design Multipitope Immunogens Based on Multiple Th Lymphocyte Epitopes", Journal of Immunology, 168, pp. 5499-5506, 2002.

Int'l Preliminary Report on Patentability dated Nov. 6, 2018 in Int'l Application No. PCT/US2017/030338.

Gall et al., "Rescue and Production of Vaccine and Therapeutic Adenovirus Vectors Expressing Inhibitory Transgenes", Molecular Biotechnology, vol. 35, pp. 263-273, 2007.

Shenk, "Adenoviridae: The Viruses and their Replication", Fields Virology, Third Edition, pp. 2111-2148, 1996.

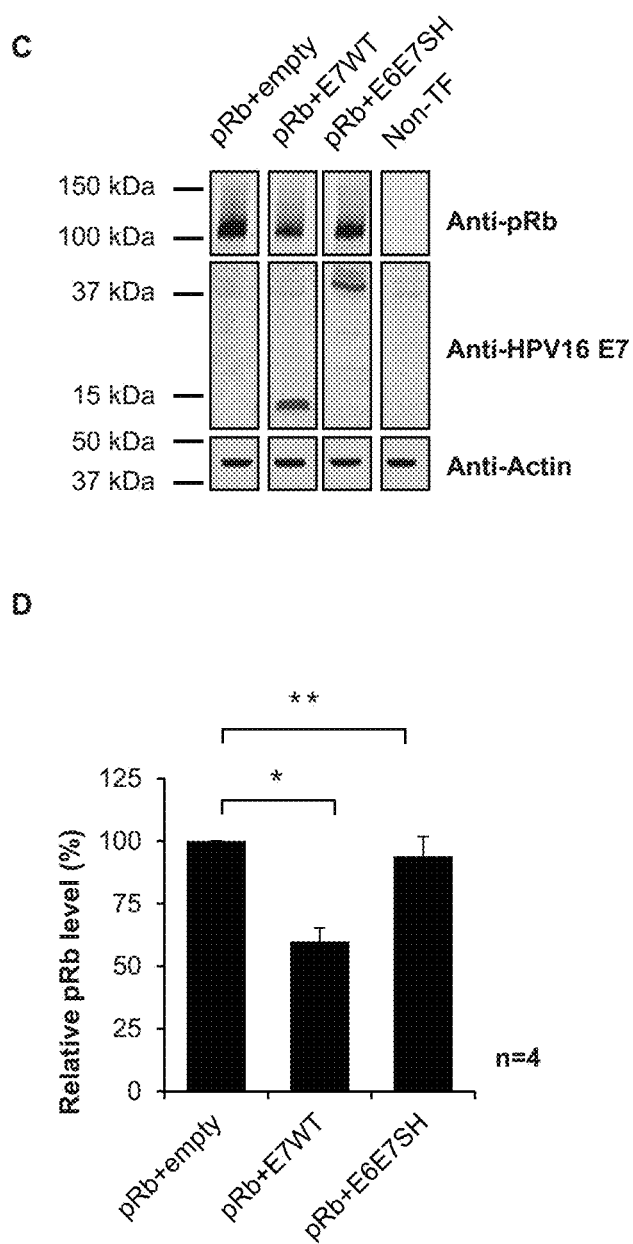
Fig. 3 - continued

A

B

F
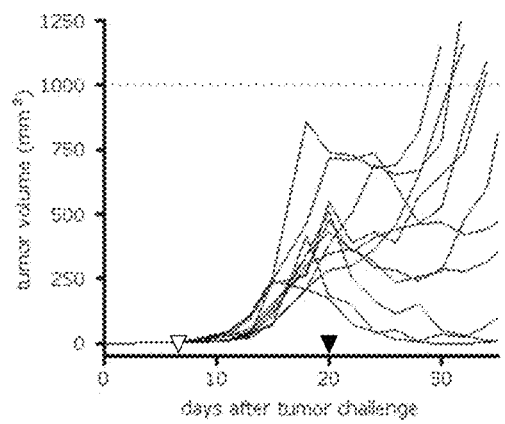
G
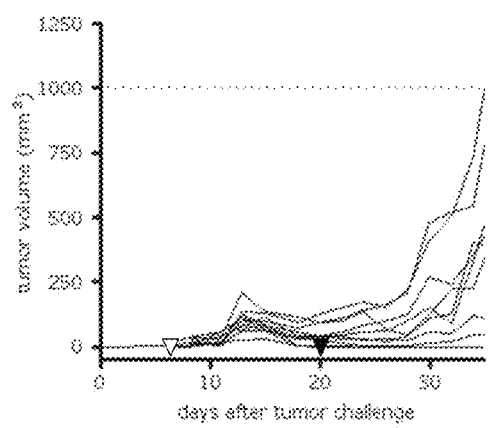
H
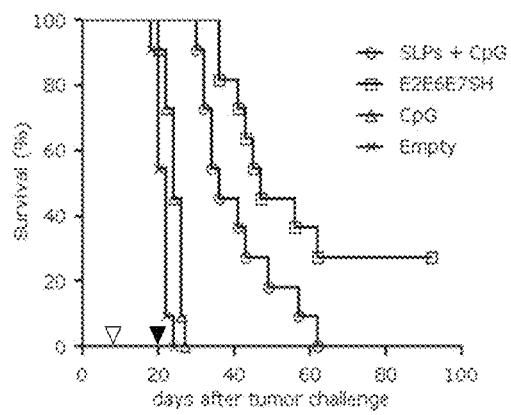
Fig. 12 - continued

A

B

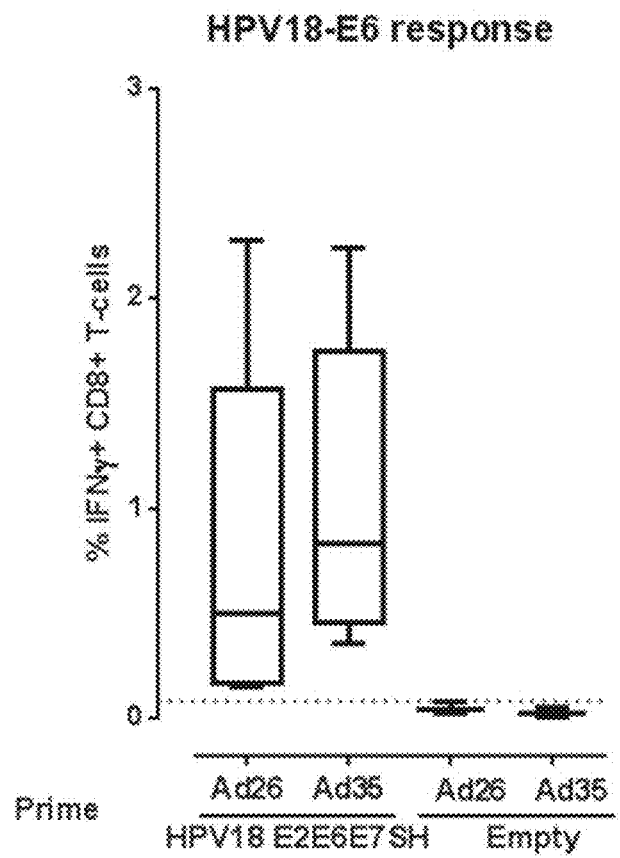
Fig. 19 - continued

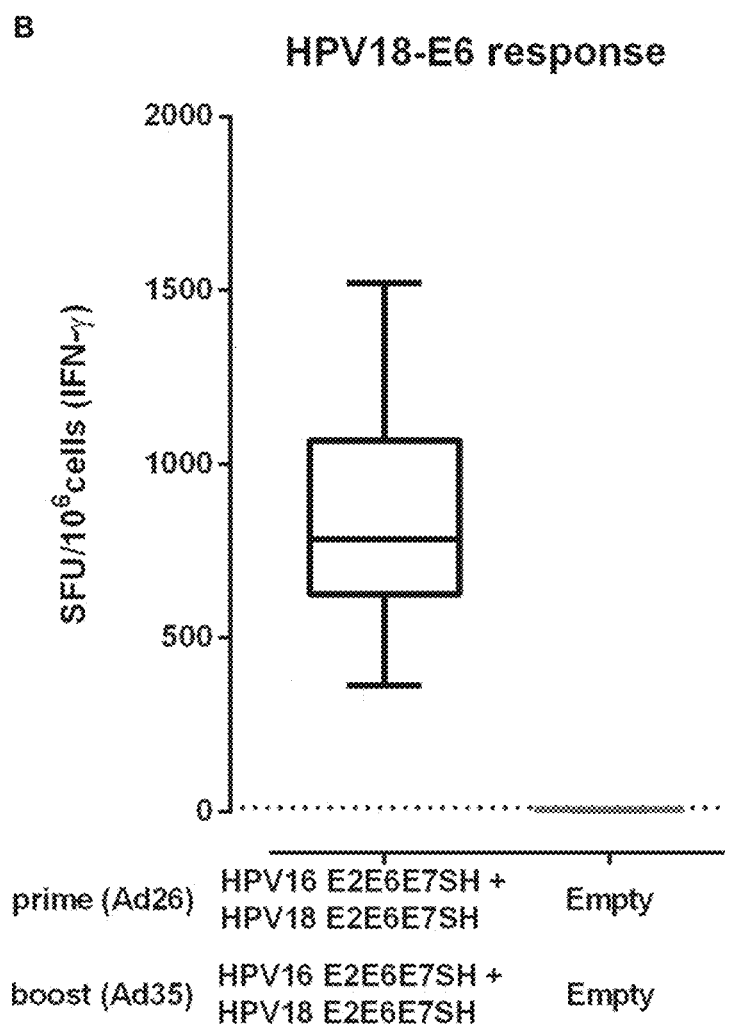
Fig. 20 – continued

SEQUENCE LISTING

```
<160> NUMBER OF SEQ ID NOS: 33

<210> SEQ ID NO 1
<211> LENGTH: 328
<212> TYPE: PRT
<213> ORGANISM: Artificial Sequence
<220> FEATURE:
<223> OTHER INFORMATION: HPV16-E6E7SH designer polypeptide

<400> SEQUENCE: 1
```

| Met | His | Gln | Lys | Arg | Thr | Ala | Met | Phe | Gln | Asp | Pro | Gln | Glu | Arg | Pro |
|---|---|---|---|---|---|---|---|---|---|---|---|---|---|---|---|
| 1 | | | | 5 | | | | | 10 | | | | | 15 | |

| Arg | Lys | Leu | Pro | Gln | Leu | Cys | Thr | Glu | Leu | Gln | Thr | Thr | Ile | His | Asp |
|---|---|---|---|---|---|---|---|---|---|---|---|---|---|---|---|
| | | | 20 | | | | | 25 | | | | | 30 | | |

| Ile | Ile | Leu | Glu | Cys | Val | Tyr | Cys | Lys | Gln | Gln | Leu | Glu | Asp | Glu | Ile |
|---|---|---|---|---|---|---|---|---|---|---|---|---|---|---|---|
| | | | 35 | | | | | 40 | | | | | 45 | | |

| Asp | Gly | Pro | Ala | Gly | Gln | Ala | Glu | Pro | Asp | Arg | Ala | His | Tyr | Asn | Ile |
|---|---|---|---|---|---|---|---|---|---|---|---|---|---|---|---|
| | 50 | | | | | 55 | | | | | 60 | | | | |

| Val | Thr | Phe | Cys | Cys | Lys | Cys | Asp | Ser | Thr | Leu | Arg | Leu | Cys | Val | Gln |
|---|---|---|---|---|---|---|---|---|---|---|---|---|---|---|---|
| 65 | | | | | 70 | | | | | 75 | | | | | 80 |

| Ser | Thr | His | Val | Asp | Ile | Arg | Thr | Leu | Glu | Asp | Leu | Leu | Met | Gly | Thr |
|---|---|---|---|---|---|---|---|---|---|---|---|---|---|---|---|
| | | | | 85 | | | | | 90 | | | | | 95 | |

| Leu | Gly | Ile | Val | Cys | Pro | Ile | Cys | Ser | Gln | Lys | Pro | Gly | Thr | Thr | Leu |
|---|---|---|---|---|---|---|---|---|---|---|---|---|---|---|---|
| | | | 100 | | | | | 105 | | | | | 110 | | |

| Glu | Gln | Gln | Tyr | Asn | Lys | Pro | Leu | Cys | Asp | Leu | Leu | Ile | Arg | Cys | Ile |
|---|---|---|---|---|---|---|---|---|---|---|---|---|---|---|---|
| | | | 115 | | | | | 120 | | | | | 125 | | |

| Asn | Cys | Gln | Lys | Pro | Leu | Cys | Pro | Glu | Glu | Lys | Gln | Arg | His | Leu | Asp |
|---|---|---|---|---|---|---|---|---|---|---|---|---|---|---|---|
| | 130 | | | | | 135 | | | | | 140 | | | | |

| Lys | Lys | Gln | Arg | Phe | His | Asn | Ile | Arg | Gly | Arg | Trp | Thr | Gly | Arg | Cys |
|---|---|---|---|---|---|---|---|---|---|---|---|---|---|---|---|
| 145 | | | | | 150 | | | | | 155 | | | | | 160 |

| Met | Ser | Cys | Cys | Arg | Ser | Ser | Arg | Thr | Arg | Arg | Glu | Thr | Gln | Met | His |
|---|---|---|---|---|---|---|---|---|---|---|---|---|---|---|---|
| | | | | 165 | | | | | 170 | | | | | 175 | |

| Gly | Asp | Thr | Pro | Thr | Leu | His | Glu | Tyr | Met | Leu | Asp | Leu | Gln | Pro | Glu |
|---|---|---|---|---|---|---|---|---|---|---|---|---|---|---|---|
| | | | 180 | | | | | 185 | | | | | 190 | | |

| Thr | Thr | Asp | Leu | Tyr | Cys | Tyr | Glu | Gln | Leu | Asn | Asp | Ser | Ser | Glu | Glu |
|---|---|---|---|---|---|---|---|---|---|---|---|---|---|---|---|
| | | | 195 | | | | | 200 | | | | | 205 | | |

| Glu | Asp | Glu | Ile | Asp | Gly | Pro | Ala | Gly | Gln | Ala | Glu | Pro | Asp | Arg | Ala |
|---|---|---|---|---|---|---|---|---|---|---|---|---|---|---|---|
| | 210 | | | | | 215 | | | | | 220 | | | | |

| His | Tyr | Asn | Ile | Val | Thr | Phe | Cys | Cys | Gln | Leu | Cys | Thr | Glu | Leu | Gln |
|---|---|---|---|---|---|---|---|---|---|---|---|---|---|---|---|
| 225 | | | | | 230 | | | | | 235 | | | | | 240 |

| Thr | Thr | Ile | His | Asp | Ile | Ile | Leu | Glu | Cys | Val | Tyr | Cys | Lys | Gln | Gln |
|---|---|---|---|---|---|---|---|---|---|---|---|---|---|---|---|
| | | | | 245 | | | | | 250 | | | | | 255 | |

| Leu | Leu | Arg | Arg | Glu | Val | Tyr | Asp | Phe | Ala | Phe | Arg | Asp | Leu | Cys | Ile |
|---|---|---|---|---|---|---|---|---|---|---|---|---|---|---|---|
| | | | 260 | | | | | 265 | | | | | 270 | | |

| Val | Tyr | Arg | Asp | Gly | Asn | Pro | Tyr | Ala | Val | Cys | Asp | Lys | Cys | Leu | Lys |

```
            275                 280                 285
Phe Tyr Ser Lys Ile Ser Glu Tyr Arg His Tyr Cys Tyr Ser Leu Tyr
        290                 295                 300
Gly Thr Thr Leu Glu Gln Gln Tyr Asn Lys Pro Leu Cys Asp Leu Leu
305                 310                 315                 320

Ile Arg Cys Ile Asn Cys Gln Lys
                325

<210> SEQ ID NO 2
<211> LENGTH: 990
<212> TYPE: DNA
<213> ORGANISM: Artificial Sequence
<220> FEATURE:
<223> OTHER INFORMATION: nt sequence encoding HPV16-E6E7SH designer
      polypeptide

<400> SEQUENCE: 2
atgcaccaga acggaccgc catgttccag accccaggg aacggcccag aaagctgccc          60
cagctgtgca ccgagctgca gaccaccatc acgacatca tcctggaatg cgtgtactgc        120
aagcagcagc tggaagatga gatcgacggc cctgctggcc aggccgaacc cgacagagcc      180
cactacaata tcgtgacctt ctgctgcaag tgcgacagca ccctgcggct gtgcgtgcag       240
agcacccacg tggacatccg gaccctggaa gatctgctga tgggcacccct gggcatcgtg     300 tgccccatct gcagccagaa gcccggcacc accctggaac agcagtacaa caagcccctg      360
tgcgacctgc tgatccggtg catcaactgc agaaaccccc tgtgccccga ggaaaagcag     420
cggcacctgg acaagaagca gcggttccac aacatccggg gcagatggac aggcagatgc     480
atgagctgct gcagaagcag ccggaccaga cgggaaaccc agatgcacgg cgacaccccc    540
accctgcacg agtacatgct ggacctgcag cccgagacaa ccgacctgta ctgctacgag     600
cagctgaacg acagcagcga ggaagaggac gagattgacg acccgctgg acaggccgag      660 cctgaccggc tcactataa catcgtgaca ttttgctgtc agctctgtac tgaactccag        720
acaacaattc acgatattat tctcgaatgt gtgtattgta aacagcagct cctgcggaga     780
gaggtgtacg acttcgcctt ccgggacctc tgcatcgtgt atcgggacgg caaccccta    840 gccgtgtgcg acaagtgcct gaagttctac agcaagatca gcgagtaccg gcactactgc     900
tacagcctgt acgaacaac actcgaacag cagtataaca aaccactctg tgatctgctg      960
attcgctgta tcaattgtca gaagtgataa                                        990

<210> SEQ ID NO 3
<211> LENGTH: 693
<212> TYPE: PRT
<213> ORGANISM: Artificial Sequence
<220> FEATURE:
<223> OTHER INFORMATION: HPV16 E2E6E7SH designer polypeptide

<400> SEQUENCE: 3

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
```

-continued

```
                65                  70                  75                  80
            Thr Ile Tyr Asn Ser Gln Tyr Ser Asn Glu Lys Trp Thr Leu Gln Asp
                                85                  90                  95

Val Ser Leu Glu Val Tyr Leu Thr Ala Pro Thr Gly Cys Ile Lys Lys
                            100                 105                 110

His Gly Tyr Thr Val Glu Val Gln Phe Asp Gly Asp Ile Cys Asn Thr
                        115                 120                 125

Met His Tyr Thr Asn Trp Thr His Ile Tyr Ile Cys Glu Glu Ala Ser
                    130                 135                 140

Val Thr Val Val Glu Gly Gln Val Asp Tyr Tyr Gly Leu Tyr Tyr Val
            145                 150                 155                 160

His Glu Gly Ile Arg Thr Tyr Phe Val Gln Phe Lys Asp Asp Ala Glu
                                165                 170                 175

Lys Tyr Ser Lys Asn Lys Val Trp Glu Val His Ala Gly Gly Gln Val
                            180                 185                 190

Ile Leu Cys Pro Thr Ser Val Phe Ser Ser Asn Glu Val Ser Ser Pro
                        195                 200                 205

Glu Ile Ile Arg Gln His Leu Ala Asn His Pro Ala Ala Thr His Thr
                    210                 215                 220

Lys Ala Val Ala Leu Gly Thr Glu Glu Thr Gln Thr Thr Ile Gln Arg
            225                 230                 235                 240

Pro Arg Ser Glu Pro Asp Thr Gly Asn Pro Cys His Thr Thr Lys Leu
                                245                 250                 255

Leu His Arg Asp Ser Val Asp Ser Ala Pro Ile Leu Thr Ala Phe Asn
                            260                 265                 270

Ser Ser His Lys Gly Arg Ile Asn Cys Asn Ser Asn Thr Thr Pro Ile
                        275                 280                 285

Val His Leu Lys Val Asp Ala Asn Thr Leu Met Arg Leu Arg Tyr Arg
                    290                 295                 300

Phe Lys Lys His Cys Thr Leu Tyr Thr Ala Val Ser Ser Thr Trp His
            305                 310                 315                 320

Trp Thr Gly His Asn Val Lys His Lys Ser Ala Ile Val Thr Leu Thr
                                325                 330                 335

Tyr Asp Ser Glu Trp Gln Arg Asp Gln Phe Leu Ser Gln Val Lys Ile
                            340                 345                 350

Pro Lys Thr Ile Thr Val Ser Thr Gly Phe Met Ser Ile Met His Gln
                        355                 360                 365

Lys Arg Thr Ala Met Phe Gln Asp Pro Gln Glu Arg Pro Arg Lys Leu
                    370                 375                 380

Pro Gln Leu Cys Thr Glu Leu Gln Thr Thr Ile His Asp Ile Ile Leu
            385                 390                 395                 400

Glu Cys Val Tyr Cys Lys Gln Gln Leu Glu Asp Glu Ile Asp Gly Pro
                                405                 410                 415

Ala Gly Gln Ala Glu Pro Asp Arg Ala His Tyr Asn Ile Val Thr Phe
                            420                 425                 430

Cys Cys Lys Cys Asp Ser Thr Leu Arg Leu Cys Val Gln Ser Thr His
                        435                 440                 445

Val Asp Ile Arg Thr Leu Glu Asp Leu Leu Met Gly Thr Leu Gly Ile
                    450                 455                 460

Val Cys Pro Ile Cys Ser Gln Lys Pro Gly Thr Thr Leu Glu Gln Gln
            465                 470                 475                 480

Tyr Asn Lys Pro Leu Cys Asp Leu Leu Ile Arg Cys Ile Asn Cys Gln
                                485                 490                 495
```

```
Lys Pro Leu Cys Pro Glu Glu Lys Gln Arg His Leu Asp Lys Lys Gln
            500                 505                 510
Arg Phe His Asn Ile Arg Gly Arg Trp Thr Gly Arg Cys Met Ser Cys
        515                 520                 525
Cys Arg Ser Ser Arg Thr Arg Arg Glu Thr Gln Met His Gly Asp Thr
    530                 535                 540
Pro Thr Leu His Glu Tyr Met Leu Asp Leu Gln Pro Glu Thr Thr Asp
545                 550                 555                 560
Leu Tyr Cys Tyr Glu Gln Leu Asn Asp Ser Ser Glu Glu Glu Asp Glu
                565                 570                 575
Ile Asp Gly Pro Ala Gly Gln Ala Glu Pro Asp Arg Ala His Tyr Asn
            580                 585                 590
Ile Val Thr Phe Cys Cys Gln Leu Cys Thr Glu Leu Gln Thr Thr Ile
        595                 600                 605
His Asp Ile Ile Leu Glu Cys Val Tyr Cys Lys Gln Gln Leu Leu Arg
    610                 615                 620
Arg Glu Val Tyr Asp Phe Ala Phe Arg Asp Leu Cys Ile Val Tyr Arg
625                 630                 635                 640
Asp Gly Asn Pro Tyr Ala Val Cys Asp Lys Cys Leu Lys Phe Tyr Ser
                645                 650                 655
Lys Ile Ser Glu Tyr Arg His Tyr Cys Tyr Ser Leu Tyr Gly Thr Thr
            660                 665                 670
Leu Glu Gln Gln Tyr Asn Lys Pro Leu Cys Asp Leu Leu Ile Arg Cys
        675                 680                 685
Ile Asn Cys Gln Lys
    690
```

<210> SEQ ID NO 4
<211> LENGTH: 2085
<212> TYPE: DNA
<213> ORGANISM: Artificial Sequence
<220> FEATURE:
<223> OTHER INFORMATION: nt sequence encoding HPV16 E2E6E7SH designer
      polypeptide

<400> SEQUENCE: 4

| | | |
|---|---|---|
| atggaaaccc tgtgccagcg gctgaacgtg tgccaggaca agatcctgac ccactacgag | 60 |
| aacgacagca ccgacctgcg ggaccacatc gactactgga agcacatgcg gctggaatgc | 120 |
| gccatctact acaaggccag agagatgggc ttcaagcaca tcaaccacca ggtggtgccc | 180 |
| accctggccg tgtccaagaa caaggccctg caggccatcg agctgcagct gaccctggaa | 240 |
| accatctaca catgccagta cagcaacgag aagtggaccc tgcaggacgt gtccctggaa | 300 |
| gtgtacctga ccgctcccac cggctgcatc aagaaacacg gctacaccgt ggaagtgcag | 360 |
| ttcgacggcg acatctgcaa caccatgcac tacaccaact ggacccacat ctacatctgc | 420 |
| gaagaggcca gcgtgaccgt ggtggaaggc caggtggact actacggcct gtactacgtg | 480 |
| cacgagggca tccggaccta cttcgtgcag ttcaaggacg acgccgagaa gtacagcaag | 540 |
| aacaaagtgt gggaggtgca cgctggcggc caggtcatcc tgtgcccccac cagcgtgttc | 600 |
| agcagcaacg aggtgtccag ccccgagatc atccggcagc acctggccaa tcaccctgcc | 660 |
| gccacccaca caaggccgt ggccctgggc accgaggaaa cccagaccac catccagcgg | 720 |
| cccagaagcg agcccgacac cggcaatccc tgccacacca ccaagctgct gaccgggac | 780 |
| agcgtggaca gcgcccctat cctgaccgcc ttcaacagca gccacaaggg ccggatcaac | 840 |

| | |
|---|---|
| tgcaacagca acaccacccc catcgtgcac ctgaaggtgg acgccaacac cctgatgcgg | 900 |
| ctgcggtaca gattcaagaa gcactgcacc ctgtacaccg ccgtgtcctc cacctggcac | 960 |
| tggaccggcc acaacgtgaa gcacaagagc gccatcgtga ccctgaccta cgacagcgag | 1020 |
| tggcagcggg accagttcct gagccaggtc aaaatcccca agaccatcac cgtgtccacc | 1080 |
| ggcttcatga gcatcatgca ccagaaacgg accgccatgt ccaggacccc caggaacgg | 1140 |
| cccagaaagc tgcccccagct gtgcaccgag ctgcagacca ccatccacga catcatcctg | 1200 |
| gaatgcgtgt actgcaagca gcagctggaa gatgagatcg acggccctgc tggccaggcc | 1260 |
| gaacccgaca gagcccacta caatatcgtg accttctgct gcaagtgcga cagcacccctg | 1320 |
| cggctgtgcg tgcagagcac ccacgtggac atccggaccc tggaagatct gctgatgggc | 1380 |
| accctgggca tcgtgtgccc catctgcagc cagaagcccg gcaccaccct ggaacagcag | 1440 |
| tacaacaagc ccctgtgcga cctgctgatc cggtgcatca actgccagaa acccctgtgc | 1500 |
| cccgaggaaa agcagcggca cctggacaag aagcagcggt tccacaacat ccggggcaga | 1560 |
| tggacaggca gatgcatgag ctgctgcaga agcagccgga ccagacggga aacccagatg | 1620 |
| cacggcgaca ccccccaccct gcacgagtac atgctggacc tgcagcccga gacaaccgac | 1680 |
| ctgtactgct acgagcagct gaacgacagc agcgaggaag aggacgagat tgacggaccc | 1740 |
| gctggacagg ccgagcctga ccgggctcac tataacatcg tgacatttttg ctgtcagctc | 1800 |
| tgtactgaac tccagacaac aattcacgat attattctcg aatgtgtgta ttgtaaacag | 1860 |
| cagctcctgc ggagagaggt gtacgacttc gccttccggg acctctgcat cgtgtatcgg | 1920 |
| gacggcaacc cctacgccgt gtgcgacaag tgcctgaagt tctacagcaa gatcagcgag | 1980 |
| taccggcact actgctacag cctgtacgga acaacactcg aacagcagta taacaaacca | 2040 |
| ctctgtgatc tgctgattcg ctgtatcaat tgtcagaagt gataa | 2085 |

<210> SEQ ID NO 5
<211> LENGTH: 693
<212> TYPE: PRT
<213> ORGANISM: Artificial Sequence
<220> FEATURE:
<223> OTHER INFORMATION: HPV16 E6E7E2SH designer polypeptide

<400> SEQUENCE: 5

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Glu Asp Glu Ile
        35                  40                  45

Asp Gly Pro Ala Gly Gln Ala Glu Pro Asp Arg Ala His Tyr Asn Ile
    50                  55                  60

Val Thr Phe Cys Cys Lys Cys Asp Ser Thr Leu Arg Leu Cys Val Gln
65                  70                  75                  80

Ser Thr His Val Asp Ile Arg Thr Leu Glu Asp Leu Leu Met Gly Thr
                85                  90                  95

Leu Gly Ile Val Cys Pro Ile Cys Ser Gln Lys Pro Gly Thr Thr Leu
            100                 105                 110

Glu Gln Gln Tyr Asn Lys Pro Leu Cys Asp Leu Leu Ile Arg Cys Ile
        115                 120                 125

Asn Cys Gln Lys Pro Leu Cys Pro Glu Glu Lys Gln Arg His Leu Asp
    130                 135                 140
```

```
Lys Lys Gln Arg Phe His Asn Ile Arg Gly Arg Trp Thr Gly Arg Cys
145                 150                 155                 160

Met Ser Cys Cys Arg Ser Ser Arg Thr Arg Glu Thr Gln Met His
            165                 170                 175

Gly Asp Thr Pro Thr Leu His Glu Tyr Met Leu Asp Leu Gln Pro Glu
                180                 185                 190

Thr Thr Asp Leu Tyr Cys Tyr Glu Gln Leu Asn Asp Ser Ser Glu Glu
            195                 200                 205

Glu Asp Glu Ile Asp Gly Pro Ala Gly Gln Ala Glu Pro Asp Arg Ala
    210                 215                 220

His Tyr Asn Ile Val Thr Phe Cys Cys Gln Leu Cys Thr Glu Leu Gln
225                 230                 235                 240

Thr Thr Ile His Asp Ile Ile Leu Glu Cys Val Tyr Cys Lys Gln Gln
                245                 250                 255

Leu Leu Arg Arg Glu Val Tyr Asp Phe Ala Phe Arg Asp Leu Cys Ile
            260                 265                 270

Val Tyr Arg Asp Gly Asn Pro Tyr Ala Val Cys Asp Lys Cys Leu Lys
    275                 280                 285

Phe Tyr Ser Lys Ile Ser Glu Tyr Arg His Tyr Cys Tyr Ser Leu Tyr
290                 295                 300

Gly Thr Thr Leu Glu Gln Gln Tyr Asn Lys Pro Leu Cys Asp Leu Leu
305                 310                 315                 320

Ile Arg Cys Ile Asn Cys Gln Lys Met Glu Thr Leu Cys Gln Arg Leu
            325                 330                 335

Asn Val Cys Gln Asp Lys Ile Leu Thr His Tyr Glu Asn Asp Ser Thr
        340                 345                 350

Asp Leu Arg Asp His Ile Asp Tyr Trp Lys His Met Arg Leu Glu Cys
            355                 360                 365

Ala Ile Tyr Tyr Lys Ala Arg Glu Met Gly Phe Lys His Ile Asn His
    370                 375                 380

Gln Val Val Pro Thr Leu Ala Val Ser Lys Asn Lys Ala Leu Gln Ala
385                 390                 395                 400

Ile Glu Leu Gln Leu Thr Leu Glu Thr Ile Tyr Asn Ser Gln Tyr Ser
                405                 410                 415

Asn Glu Lys Trp Thr Leu Gln Asp Val Ser Leu Glu Val Tyr Leu Thr
            420                 425                 430

Ala Pro Thr Gly Cys Ile Lys Lys His Gly Tyr Thr Val Glu Val Gln
        435                 440                 445

Phe Asp Gly Asp Ile Cys Asn Thr Met His Tyr Thr Asn Trp Thr His
450                 455                 460

Ile Tyr Ile Cys Glu Glu Ala Ser Val Thr Val Val Glu Gly Gln Val
465                 470                 475                 480

Asp Tyr Tyr Gly Leu Tyr Tyr Val His Glu Gly Ile Arg Thr Tyr Phe
            485                 490                 495

Val Gln Phe Lys Asp Asp Ala Glu Lys Tyr Ser Lys Asn Lys Val Trp
        500                 505                 510

Glu Val His Ala Gly Gly Gln Val Ile Leu Cys Pro Thr Ser Val Phe
    515                 520                 525

Ser Ser Asn Glu Val Ser Ser Pro Glu Ile Ile Arg Gln His Leu Ala
            530                 535                 540

Asn His Pro Ala Ala Thr His Thr Lys Ala Val Ala Leu Gly Thr Glu
545                 550                 555                 560

Glu Thr Gln Thr Thr Ile Gln Arg Pro Arg Ser Glu Pro Asp Thr Gly
```

```
                      565                 570                 575
Asn Pro Cys His Thr Thr Lys Leu Leu His Arg Asp Ser Val Asp Ser
            580                 585                 590

Ala Pro Ile Leu Thr Ala Phe Asn Ser Ser His Lys Gly Arg Ile Asn
        595                 600                 605

Cys Asn Ser Asn Thr Thr Pro Ile Val His Leu Lys Val Asp Ala Asn
    610                 615                 620

Thr Leu Met Arg Leu Arg Tyr Arg Phe Lys Lys His Cys Thr Leu Tyr
625                 630                 635                 640

Thr Ala Val Ser Ser Thr Trp His Trp Thr Gly His Asn Val Lys His
                645                 650                 655

Lys Ser Ala Ile Val Thr Leu Thr Tyr Asp Ser Glu Trp Gln Arg Asp
            660                 665                 670

Gln Phe Leu Ser Gln Val Lys Ile Pro Lys Thr Ile Thr Val Ser Thr
        675                 680                 685

Gly Phe Met Ser Ile
    690

<210> SEQ ID NO 6
<211> LENGTH: 2085
<212> TYPE: DNA
<213> ORGANISM: Artificial Sequence
<220> FEATURE:
<223> OTHER INFORMATION: nt sequence encoding HPV16 E6E7E2SH designer
      polypeptide

<400> SEQUENCE: 6
atgcaccaga acggaccgc catgttccag accccaggg aacggcccag aaagctgccc      60
cagctgtgca ccgagctgca gaccaccatc cacgacatca tcctggaatg cgtgtactgc    120
aagcagcagc tggaagatga gatcgacggc cctgctggcc aggccgaacc cgacagagcc    180
cactacaata tcgtgacctt ctgctgcaag tgcgacagca ccctgcggct gtgcgtgcag    240
agcacccacg tggacatccg gaccctggaa gatctgctga tgggcaccct gggcatcgtg    300
tgccccatct gcagccagaa gcccggcacc accctggaac agcagtacaa caagcccctg    360
tgcgacctgc tgatccggtg catcaactgc cagaaacccc tgtgccccga ggaaaagcag    420
cggcacctgg acaagaagca gcggttccac aacatccggg gcagatggac aggcagatgc    480
atgagctgct gcagaagcag ccggaccaga cgggaaaccc cgatgcacgg cgacaccccc    540
accctgcacg agtacatgct ggacctgcag cccgagacaa ccgacctgta ctgctacgag    600
cagctgaacg acagcagcga ggaagaggac gagattgacg acccgctgg acaggccgag    660 cctgaccggg ctcactataa catcgtgaca ttttgctgtc agctctgtac tgaactccag    720
acaacaattc acgatattat tctcgaatgt gtgtattgta acagcagct cctgcgggaga   780 gaggtgtacg acttcgcctt ccgggacctc tgcatcgtgt atcgggacgg caacccctac    840
gccgtgtgcg acaagtgcct gaagttctac agcaagatca gcgagtaccg gcactactgc    900
tacagcctgt acggaacaac actcgaacag cagtataaca accactctg tgatctgctg    960 attcgctgta tcaattgtca gaagatggaa acccgtgcc agcggctgaa cgtgtgccag   1020
gacaagatcc tgacccacta cgagaacgac agcaccgacc tgcgggacca catcgactac   1080
tggaagcaca tgcggctgga atgcgccatc tactacaagg ccagagagat gggcttcaag   1140
cacatcaacc accaggtggt gcccacccctg ccgtgtcca agaacaaggc cctgcaggcc   1200
atcgagctgc agctgaccct ggaaaccatc tacaacagcc agtacagcaa cgagaagtgg   1260
```

```
accctgcagg acgtgtccct ggaagtgtac ctgaccgctc ccaccggctg catcaagaaa    1320
cacggctaca ccgtggaagt gcagttcgac ggcgacatct gcaacaccat gcactacacc    1380
aactggaccc acatctacat ctgcgaagag ccagcgtga ccgtggtgga aggccaggtg     1440
gactactacg cctgtacta cgtgcacgag ggcatccgga cctacttcgt gcagttcaag     1500
gacgacgccg agaagtacag caagaacaaa gtgtgggagg tgcacgctgg cggccaggtc    1560
atcctgtgcc ccaccagcgt gttcagcagc aacgaggtgt ccagcccga gatcatccgg     1620 cagcacctgg ccaatcaccc tgccgccacc cacacaaagg ccgtggccct gggcaccgag    1680
gaaacccaga ccaccatcca gcggcccaga agcgagcccg acaccggcaa tccctgccac    1740
accaccaagc tgctgcaccg ggacagcgtg acagcgccc ctatcctgac cgccttcaac     1800
agcagccaca agggccggat caactgcaac agcaacacca cccccatcgt gcacctgaag    1860
gtggacgcca acaccctgat gcggctgcgg tacagattca agaagcactg caccctgtac    1920
accgccgtgt cctccacctg gcactggacc ggccacaacg tgaagcacaa gagcgccatc    1980
gtgaccctga cctacgacag cgagtggcag cgggaccagt tcctgagcca ggtcaaaatc    2040
cccaagacca tcaccgtgtc caccggcttc atgagcatct gataa                    2085
```

```
<210> SEQ ID NO 7
<211> LENGTH: 18
<212> TYPE: PRT
<213> ORGANISM: Artificial Sequence
<220> FEATURE:
<223> OTHER INFORMATION: IgE leader peptide

<400> SEQUENCE: 7

Met Asp Trp Thr Trp Ile Leu Phe Leu Val Ala Ala Thr Arg Val
1               5                   10                  15

His Ser

<210> SEQ ID NO 8
<211> LENGTH: 54
<212> TYPE: DNA
<213> ORGANISM: Artificial Sequence
<220> FEATURE:
<223> OTHER INFORMATION: nt sequence encoding IgE leader peptide

<400> SEQUENCE: 8
atggactgga cctggatcct gttcctggtg gctgccgcaa cccgggtgca cagc           54

<210> SEQ ID NO 9
<211> LENGTH: 21
<212> TYPE: PRT
<213> ORGANISM: Artificial Sequence
<220> FEATURE:
<223> OTHER INFORMATION: HAVT20 leader peptide

<400> SEQUENCE: 9

Met Ala Cys Pro Gly Phe Leu Trp Ala Leu Val Ile Ser Thr Cys Leu
1               5                   10                  15

Glu Phe Ser Met Ala
            20

<210> SEQ ID NO 10
<211> LENGTH: 63
<212> TYPE: DNA
<213> ORGANISM: Artificial Sequence
<220> FEATURE:
<223> OTHER INFORMATION: nt sequence encoding HAVT20 leader peptide
```

<400> SEQUENCE: 10

```
atggcctgcc ccggctttct gtgggccctg gtcatcagca cctgtctgga attcagcatg    60
gcc                                                                   63
```

<210> SEQ ID NO 11
<211> LENGTH: 54
<212> TYPE: DNA
<213> ORGANISM: Artificial Sequence
<220> FEATURE:
<223> OTHER INFORMATION: 2xTetO-containing sequence

<400> SEQUENCE: 11

```
gagctctccc tatcagtgat agagatctcc ctatcagtga tagagatcgt cgac           54
```

<210> SEQ ID NO 12
<211> LENGTH: 28
<212> TYPE: DNA
<213> ORGANISM: Artificial Sequence
<220> FEATURE:
<223> OTHER INFORMATION: 2xCuO-containing sequence

<400> SEQUENCE: 12

```
aacaaacaga caatctggtc tgtttgta                                        28
```

<210> SEQ ID NO 13
<211> LENGTH: 829
<212> TYPE: DNA
<213> ORGANISM: Artificial Sequence
<220> FEATURE:
<223> OTHER INFORMATION: CMV promoter

<400> SEQUENCE: 13

```
tcaatattgg ccattagcca tattattcat tggttatata gcataaatca atattggcta    60
ttggccattg catacgttgt atccatatca taatatgtac atttatattg gctcatgtcc   120
aacattaccg ccatgttgac attgattatt gactagttat taatagtaat caattacggg   180
gtcattagtt catagcccat atatggagtt ccgcgttaca taacttacgg taaatggccc   240
gcctggctga ccgcccaacg acccccgccc attgacgtca ataatgacgt atgttcccat   300
agtaacgcca atagggactt tccattgacg tcaatgggtg gagtatttac ggtaaactgc   360
ccacttggca gtacatcaag tgtatcatat gccaagtacg ccccctattg acgtcaatga   420
cggtaaatgg cccgcctggc attatgccca gtacatgacc ttatgggact ttcctacttg   480
gcagtacatc tacgtattag tcatcgctat taccatggtg atgcggtttt ggcagtacat   540
caatgggcgt ggatagcggt ttgactcacg gggatttcca agtctccacc ccattgacgt   600
caatgggagt ttgttttggc accaaaatca acgggacttt ccaaaatgtc gtaacaactc   660
cgccccattg acgcaaatgg gcggtaggcg tgtacggtgg gaggtctata taagcagagc   720
tcgtttagtg aaccgtcaga tcgcctggag acgccatcca cgctgttttg acctccatag   780
aagacaccgg gaccgatcca gcctccgcgg ccgggaacgg tgcattgga                829
```

<210> SEQ ID NO 14
<211> LENGTH: 657
<212> TYPE: DNA
<213> ORGANISM: Artificial Sequence
<220> FEATURE:
<223> OTHER INFORMATION: nt sequence encoding TetR polypeptide

<400> SEQUENCE: 14

```
atgtctagat tagataaaag taaagtgatt aacagcgcat tagagctgct taatgaggtc    60
```

```
ggaatcgaag gtttaacaac ccgtaaactc gcccagaagc taggtgtaga gcagcctaca    120
ttgtattggc atgtaaaaaa taagcgggct tgctcgacg ccttagccat tgagatgtta    180
gataggcacc atactcactt ttgccctta gaagggaaa gctggcaaga ttttttacgt    240
aataacgcta aaagttttag atgtgcttta ctaagtcatc gcgatggagc aaaagtacat    300
ttaggtacac ggcctacaga aaaacagtat gaaactctcg aaaatcaatt agccttttta    360
tgccaacaag gttttcact agagaatgca ttatatgcac tcagcgctgt ggggcatttt    420
actttaggtt gcgtattgga agatcaagag catcaagtcg ctaaagaaga aagggaaaca    480
cctactactg atagtatgcc gccattatta cgacaagcta tcgaattatt tgatcaccaa    540
ggtgcagagc cagccttctt attcggcctt gaattgatca tatgcggatt agaaaaacaa    600
cttaaatgtg aaagtgggtc cgcgtacagc ggatcccggg aattcagatc ttattaa    657
```

<210> SEQ ID NO 15
<211> LENGTH: 218
<212> TYPE: PRT
<213> ORGANISM: Artificial Sequence
<220> FEATURE:
<223> OTHER INFORMATION: TetR polypeptide

<400> SEQUENCE: 15

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Gly Ser Arg Glu Phe Arg Ser Tyr
    210                 215
```

<210> SEQ ID NO 16
<211> LENGTH: 612
<212> TYPE: DNA
<213> ORGANISM: Artificial Sequence
<220> FEATURE:

<223> OTHER INFORMATION: nt sequence encoding CymR polypeptide

<400> SEQUENCE: 16

```
atgtctccca acgacggac tcaagcggaa agggcaatgg aaactcaggg taagctgatt        60
gccgcggctc tgggagtgct gcgagagaaa gggtatgccg ggtttcgcat agccgacgtt      120
cctggagctg caggcgtaag cagaggagcc aatctcatc actttccgac caagctggag       180
cttttgctgg ctaccttcga atggctgtac gagcagatca cggaaggag tcgtgctagg       240
ctggccaagc tgaaacccga ggatgatgtc attcagcaga tgctggacga tgcagccgag      300
ttcttcctgg acgacgactt cagcatcagt ctcgacctca tcgtagccgc agatcgcgat      360
ccagctttgc gcgagggcat acagagaaca gtcgagcgga atcggtttgt ggtggaggac      420
atgtggcttg gtgttctggt gagcagaggc ctctcacggg atgatgccga ggacatcctg      480
tggctgatct ttaactccgt cagagggttg gcagtgaggt cccttggca gaaggacaaa      540
gaacggtttg aacgtgtgcg aaactcaaca ctcgagattg ctagggaacg ctacgccaag      600
ttcaagagat ga                                                            612
```

<210> SEQ ID NO 17
<211> LENGTH: 203
<212> TYPE: PRT
<213> ORGANISM: Artificial Sequence
<220> FEATURE:
<223> OTHER INFORMATION: CymR polypeptide

<400> SEQUENCE: 17

```
Met Ser Pro Lys Arg Arg Thr Gln Ala Glu Arg Ala Met Glu Thr Gln
  1               5                  10                  15

Gly Lys Leu Ile Ala Ala Ala Leu Gly Val Leu Arg Glu Lys Gly Tyr
             20                  25                  30

Ala Gly Phe Arg Ile Ala Asp Val Pro Gly Ala Ala Gly Val Ser Arg
         35                  40                  45

Gly Ala Gln Ser His His Phe Pro Thr Lys Leu Glu Leu Leu Leu Ala
     50                  55                  60

Thr Phe Glu Trp Leu Tyr Glu Gln Ile Thr Glu Arg Ser Arg Ala Arg
 65                  70                  75                  80

Leu Ala Lys Leu Lys Pro Glu Asp Asp Val Ile Gln Gln Met Leu Asp
                 85                  90                  95

Asp Ala Ala Glu Phe Phe Leu Asp Asp Phe Ser Ile Ser Leu Asp
            100                 105                 110

Leu Ile Val Ala Ala Asp Arg Asp Pro Ala Leu Arg Glu Gly Ile Gln
        115                 120                 125

Arg Thr Val Glu Arg Asn Arg Phe Val Val Glu Asp Met Trp Leu Gly
    130                 135                 140

Val Leu Val Ser Arg Gly Leu Ser Arg Asp Asp Ala Glu Asp Ile Leu
145                 150                 155                 160

Trp Leu Ile Phe Asn Ser Val Arg Gly Leu Ala Val Arg Ser Leu Trp
                165                 170                 175

Gln Lys Asp Lys Glu Arg Phe Glu Arg Val Arg Asn Ser Thr Leu Glu
            180                 185                 190

Ile Ala Arg Glu Arg Tyr Ala Lys Phe Lys Arg
        195                 200
```

<210> SEQ ID NO 18
<211> LENGTH: 25
<212> TYPE: PRT

<213> ORGANISM: Artificial Sequence
<220> FEATURE:
<223> OTHER INFORMATION: HPV16 E6 aa41-65

<400> SEQUENCE: 18

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 19
<211> LENGTH: 35
<212> TYPE: PRT
<213> ORGANISM: Artificial Sequence
<220> FEATURE:
<223> OTHER INFORMATION: HPV16 E7 aa43-77

<400> SEQUENCE: 19

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 20
<211> LENGTH: 331
<212> TYPE: PRT
<213> ORGANISM: Artificial Sequence
<220> FEATURE:
<223> OTHER INFORMATION: HPV18-E6E7SH designer polypeptide

<400> SEQUENCE: 20

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Asp Leu Leu Cys His Glu Gln Leu Ser
                35                  40                  45

Asp Ser Glu Glu Glu Asn Asp Glu Ile Asp Gly Val Asn His Gln His
        50                  55                  60

Leu Pro Ala Arg Arg Ala Glu Pro Gln Arg His Thr Met Leu Cys Met
65                  70                  75                  80

Cys Cys Lys Cys Glu Ala Arg Ile Glu Leu Val Val Glu Ser Ser Ala
                85                  90                  95

Asp Asp Leu Arg Ala Phe Gln Gln Leu Phe Leu Asn Thr Leu Ser Phe
            100                 105                 110

Val Cys Pro Trp Cys Ala Ser Gln His Tyr Ser Asp Ser Val Tyr Gly
        115                 120                 125

Asp Thr Leu Glu Lys Leu Thr Asn Thr Gly Leu Tyr Asn Leu Leu Ile
    130                 135                 140

Arg Cys Leu Arg Cys Gln Lys Pro Leu Asn Pro Ala Glu Lys Leu Arg
145                 150                 155                 160

His Leu Asn Glu Lys Arg Arg Phe His Asn Ile Ala Gly His Tyr Arg
                165                 170                 175

Gly Gln Cys His Ser Cys Cys Asn Arg Ala Arg Gln Glu Arg Leu Gln
            180                 185                 190

Arg Arg Arg Glu Thr Met His Gly Pro Lys Ala Thr Leu Gln Asp Ile
        195                 200                 205

Val Leu His Leu Glu Pro Gln Asn Glu Ile Pro Val Asp Leu Leu Cys
    210                 215                 220

His Glu Gln Leu Ser Asp Ser Glu Glu Asn Asp Glu Ile Asp Gly
225                 230                 235                 240

Val Asn Pro Asp Leu Cys Thr Glu Leu Asn Thr Ser Leu Gln Asp Ile
            245                 250                 255

Glu Ile Thr Cys Val Tyr Cys Lys Thr Val Leu Glu Leu Thr Glu Val
            260                 265                 270

Phe Glu Phe Ala Phe Lys Asp Leu Phe Val Val Tyr Arg Asp Ser Ile
        275                 280                 285

Pro His Ala Ala Cys His Lys Cys Ile Asp Phe Tyr Ser Arg Ile Arg
    290                 295                 300

Glu Leu Arg His Tyr Ser Asp Ser Val Tyr Gly Asp Thr Leu Glu Lys
305                 310                 315                 320

Leu Thr Asn Thr Gly Leu Tyr Asn Leu Leu Ile
                325                 330

<210> SEQ ID NO 21
<211> LENGTH: 999
<212> TYPE: DNA
<213> ORGANISM: Artificial Sequence
<220> FEATURE:
<223> OTHER INFORMATION: nt sequence of HPV18-E6E7SH designer sequence

<400> SEQUENCE: 21
atggccagat tcgaggaccc caccagacgg ccctacaagc tgcccgacct gtgcaccgag    60
ctgaacacat ctctgcagga catcgagatc acatgcgtgt actgcaagac cgtgctggac   120
ctgctgtgcc acgagcagct gtccgactcc gaggaagaaa acgacgagat cgacggcgtg   180
aaccatcagc atctgcccgc cagacgggcc gagccccaga cacaccat gctgtgcatg   240 tgctgcaagt gcgaggcccg gattgagctg gtggtggaaa gcagcgccga cgacctgcgg   300
gccttccagc agctctttct gaatacc ctg agcttcgtgt gcccttggtg cgccagccag   360
cactacagcg actccgtgta cggcgatacc ctggaaaagc tgaccaatac cggcctgtat   420
aacctgctga tccggtgcct gcggtgccag aagcccctga tcccgccga aaactgaga   480 cacctgaacg agaagcggcg gttccacaat atcgccggcc actacagagg ccagtgccac   540
agctgctgca accgggccag acaggaacgg ctgcagcgga ggcgggaaac catgcacgga   600
cccaaggcca ccctccagga cattgtcctg cacctggaac cccagaacga gatccccgtc   660
gatctgctgt gtcatgaaca gctcagcgac agcgaagagg aaaatgacga aattgacggg   720
gtcaaccctg acctctgtac cgaactcaat accagtctcc aggatatcga aattacctgt   780
gtctactgta aaaccgtcct cgagctgacc gaggtgttcg agttcgcctt caaggacctg   840
tttgtggtgt acagagacag catcccccac gccgctgcc acaagtgcat cgacttctac   900
agccggatca gagagctgcg gcactactcc gattctgtgt atggcgacac actcgagaag   960
ctcacaaaca caggactgta caatctgctc atctgataa    999

<210> SEQ ID NO 22
<211> LENGTH: 696
<212> TYPE: PRT
<213> ORGANISM: Artificial Sequence
<220> FEATURE:
<223> OTHER INFORMATION: HPV18-E2E6E7SH designer sequence

<400> SEQUENCE: 22

```
Met Gln Thr Pro Lys Glu Thr Leu Ser Glu Arg Leu Ser Ala Leu Gln
1               5                   10                  15

Asp Lys Ile Ile Asp His Tyr Glu Asn Asp Ser Lys Asp Ile Asp Ser
                20                  25                  30

Gln Ile Gln Tyr Trp Gln Leu Ile Arg Trp Glu Asn Ala Ile Phe Phe
            35                  40                  45

Ala Ala Arg Glu His Gly Ile Gln Thr Leu Asn His Gln Val Val Pro
50                      55                  60

Ala Tyr Asn Ile Ser Lys Ser Lys Ala His Lys Ala Ile Glu Leu Gln
65                      70                  75                  80

Met Ala Leu Gln Gly Leu Ala Gln Ser Ala Tyr Lys Thr Glu Asp Trp
                85                  90                  95

Thr Leu Gln Asp Thr Cys Glu Glu Leu Trp Asn Thr Glu Pro Thr His
                100                 105                 110

Cys Phe Lys Lys Gly Gly Gln Thr Val Gln Val Tyr Phe Asp Gly Asn
            115                 120                 125

Lys Asp Asn Cys Met Thr Tyr Val Ala Trp Asp Ser Val Tyr Tyr Met
        130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
            180                 185                 190

Phe Gly Asn Asn Val Ile Asp Cys Asn Asp Ser Met Cys Ser Thr Ser
        195                 200                 205

Asp Asp Thr Val Ser Ala Thr Gln Leu Val Lys Gln Leu Gln His Thr
    210                 215                 220

Pro Ser Pro Tyr Ser Ser Thr Val Ser Val Gly Thr Ala Lys Thr Tyr
225                 230                 235                 240

Gly Gln Thr Ser Ala Ala Thr Arg Pro Gly His Cys Gly Leu Ala Glu
                245                 250                 255

Lys Gln His Cys Gly Pro Val Asn Pro Leu Leu Gly Ala Ala Thr Pro
            260                 265                 270

Thr Gly Asn Asn Lys Arg Arg Lys Leu Cys Ser Gly Asn Thr Thr Pro
        275                 280                 285

Ile Ile His Leu Lys Val Asp Arg Asn Ser Leu Met Arg Leu Arg Tyr
    290                 295                 300

Arg Leu Arg Lys His Ser Asp His Tyr Arg Asp Ile Ser Ser Thr Trp
305                 310                 315                 320

His Trp Thr Gly Ala Gly Asn Glu Lys Thr Gly Ile Leu Thr Val Thr
                325                 330                 335

Tyr His Ser Glu Thr Gln Arg Thr Lys Phe Leu Asn Thr Val Ala Ile
            340                 345                 350

Pro Asp Ser Val Gln Ile Leu Val Gly Tyr Met Thr Met Met Ala Arg
        355                 360                 365

Phe Glu Asp Pro Thr Arg Arg Pro Tyr Lys Leu Pro Asp Leu Cys Thr
    370                 375                 380

Glu Leu Asn Thr Ser Leu Gln Asp Ile Glu Ile Thr Cys Val Tyr Cys
385                 390                 395                 400

Lys Thr Val Leu Asp Leu Leu Cys His Glu Gln Leu Ser Asp Ser Glu
                405                 410                 415

Glu Glu Asn Asp Glu Ile Asp Gly Val Asn His Gln His Leu Pro Ala
```

```
                    420             425             430
Arg Arg Ala Glu Pro Gln Arg His Thr Met Leu Cys Met Cys Cys Lys
        435                 440                 445

Cys Glu Ala Arg Ile Glu Leu Val Val Glu Ser Ser Ala Asp Asp Leu
    450                 455                 460

Arg Ala Phe Gln Gln Leu Phe Leu Asn Thr Leu Ser Phe Val Cys Pro
465                 470                 475                 480

Trp Cys Ala Ser Gln His Tyr Ser Asp Ser Val Tyr Gly Asp Thr Leu
                485                 490                 495

Glu Lys Leu Thr Asn Thr Gly Leu Tyr Asn Leu Leu Ile Arg Cys Leu
            500                 505                 510

Arg Cys Gln Lys Pro Leu Asn Pro Ala Glu Lys Leu Arg His Leu Asn
        515                 520                 525

Glu Lys Arg Arg Phe His Asn Ile Ala Gly His Tyr Arg Gly Gln Cys
    530                 535                 540

His Ser Cys Cys Asn Arg Ala Arg Gln Glu Arg Leu Gln Arg Arg Arg
545                 550                 555                 560

Glu Thr Met His Gly Pro Lys Ala Thr Leu Gln Asp Ile Val Leu His
                565                 570                 575

Leu Glu Pro Gln Asn Glu Ile Pro Val Asp Leu Leu Cys His Glu Gln
            580                 585                 590

Leu Ser Asp Ser Glu Glu Glu Asn Asp Glu Ile Asp Gly Val Asn Pro
        595                 600                 605

Asp Leu Cys Thr Glu Leu Asn Thr Ser Leu Gln Asp Ile Glu Ile Thr
    610                 615                 620

Cys Val Tyr Cys Lys Thr Val Leu Glu Leu Thr Glu Val Phe Glu Phe
625                 630                 635                 640

Ala Phe Lys Asp Leu Phe Val Val Tyr Arg Asp Ser Ile Pro His Ala
                645                 650                 655

Ala Cys His Lys Cys Ile Asp Phe Tyr Ser Arg Ile Arg Glu Leu Arg
            660                 665                 670

His Tyr Ser Asp Ser Val Tyr Gly Asp Thr Leu Glu Lys Leu Thr Asn
        675                 680                 685

Thr Gly Leu Tyr Asn Leu Leu Ile
    690                 695

<210> SEQ ID NO 23
<211> LENGTH: 2094
<212> TYPE: DNA
<213> ORGANISM: Artificial Sequence
<220> FEATURE:
<223> OTHER INFORMATION: nt sequence encoding HPV18-E2E6E7SH designer
      sequence

<400> SEQUENCE: 23
atgcagaccc ccaaagagac actgagcgag cggctgagcg ccctgcagga caagatcatc      60
gaccactacg agaacgacag caaggacatc gacagccaga tccagtactg gcagctgatc     120
agatgggaga acgccatctt cttcgccgcc agagagcacg gcatccagac cctgaaccac     180
caggtggtgc cgcctacaa catcagcaag agcaaggccc acaaggctat cgagctgcag     240
atggccctgc agggactggc ccagagcgcc tacaagaccg aggactggac cctgcaggat     300
acctgcgagg aactgtggaa caccgagccc acccactgct tcaagaaagg cggccagacc     360
gtgcaggtgt acttcgacgg caacaaggac aactgcatga cctacgtggc ctgggacagc     420
gtgtactaca tgaccgacgc cggcacctgg gacaagaccg ccacctgtgt gtcccaccgg     480
```

```
ggcctgtact acgtgaaaga gggctacaac accttctaca tcgagttcaa gagcgagtgc    540
gagaagtacg gcaacaccgg cacatgggag gtgcacttcg gcaacaacgt gatcgactgc    600
aacgacagca tgtgcagcac cagcgacgac accgtgtccg ccacccagct ggtgaaacag    660
ctgcagcaca cccccagccc ctacagcagc accgtgtctg tgggcaccgc caagacctac    720
ggccagacca gcgccgccac cagacctgga cactgtggcc tggccgagaa gcagcactgc    780
ggccctgtga accctctgct gggagccgcc acccccaccg caacaacaa gcggagaaag    840 ctgtgcagcg gcaacaccac ccccatcatc cacctgaagg tggaccggaa cagcctgatg    900
cggctgcggt acagactgcg gaagcacagc gaccactacc gggacatcag cagcacctgg    960
cactggaccg gcgctggcaa cgagaaaacc ggcatcctga ccgtgaccta ccacagcgaa   1020
acccagcgga ccaagttcct gaacaccgtg ccatcccg acagcgtgca gatcctggtg    1080
ggatatatga ccatgatggc cagattcgag accccacca gacggcccta caagctgccc    1140
gacctgtgca ccgagctgaa cacatctctg caggacatcg agatcacatg cgtgtactgc   1200
aagaccgtgc tggacctgct gtgccacgag cagctgtccg actccgagga agaaaacgac   1260
gagatcgacg gcgtgaacca tcagcatctg cccgccagac gggccgagcc ccagagacac   1320
accatgctgt gcatgtgctg caagtgcgag gcccggattg agctggtggt ggaaagcagc   1380
gccgacgacc tgcgggcctt ccagcagctc tttctgaata ccctgagctt cgtgtgccct   1440
tggtgcgcca gcagcactac agcgactcc gtgtacggcg ataccctgga aaagctgacc   1500
aataccggcc tgtataacct gctgatccgg tgcctgcggt gccagaagcc cctgaatccc   1560
gccgagaaac tgagacacct gaacgagaag cggcggttcc acaatatcgc cggccactac   1620
agaggccagt gccacagctg ctgcaaccgg gccagacagg aacggctgca gcggaggcgg   1680
gaaaccatgc acggacccaa ggccacccctc caggacattg tcctgcacct ggaacccag    1740 aacgagatcc ccgtcgatct gctgtgtcat gaacagctca gcgacagcga agaggaaaat   1800
gacgaaattg acggggtcaa ccctgacctc tgtaccgaac tcaataccag tctccaggat   1860
atcgaaatta cctgtgtcta ctgtaaaacc gtcctcgagc tgaccgaggt gttcgagttc   1920
gccttcaagg acctgttttgt ggtgtacaga gacagcatcc cccacgccgc ctgccacaag   1980
tgcatcgact tctacagccg gatcagagag ctgcggcact actccgattc tgtgtatggc   2040
gacacactcg agaagctcac aaacacagga ctgtacaatc tgctcatctg ataa         2094
```

<210> SEQ ID NO 24
<211> LENGTH: 2085
<212> TYPE: DNA
<213> ORGANISM: Artificial Sequence
<220> FEATURE:
<223> OTHER INFORMATION: nt sequence encoding HPV16 E2E6E7SH designer
      polypeptide

<400> SEQUENCE: 24

```
atggaaacgc tctgccagag actcaatgtc tgccaggata agattctcac gcattatgag     60
aacgattcca cggacctgcg cgatcacatt gattattgga aacacatgcg ccttgagtgt    120
gctatctatt ataaggctcg cgaaatgggt ttcaaacata tcaatcatca ggtcgtccct    180
accctcgccg tcagcaaaaa caaagctctg caggctattg aactccagct cacccctcgag   240 acaatctaca attcccagta ctccaatgag aaatggacgc tccaggatgt gtctctcgag    300
gtctacctga cagctcctac aggatgtatt aagaaacacg gtacacggt ggaagtccag    360 tttgatggcg atatatgtaa taccatgcat tatacgaatt ggacgcatat ctatatttgt    420
```

```
gaagaggcct ctgtgacagt ggtcgaggga caggtcgact attatgggct gtattatgtg    480
cacgaaggga tcagaacata ctttgtccag tttaaggatg atgctgagaa gtattctaag    540
aacaaagttt gggaagtcca tgccggtgga caagtgattc tgtgtcctac ctccgtgttc    600
agctctaatg aggtgtcctc tccagagatc attagacagc atctggccaa ccatcctgct    660
gctacacata ccaaggctgt ggctctggga acagaagaga cacagacaac aatccagagg    720
cctcggagcg agcctgatac aggcaaccct tgtcacacaa caaaactgct gcacagagac    780
tccgtggact ccgctcctat tctgacagcc tttaactcct cccacaaagg gagaatcaat    840
tgcaattcca ataccacgcc gatcgtccac ctcaaagtgg atgctaatac tctcatgcgg    900
ctccgctacc gcttcaagaa acactgtaca ctgtatacag ctgtgtccag cacatggcat    960
tggacgggac acaatgtgaa cataagtcc gccatcgtca cgctcacata cgattccgag    1020
tggcagagag atcagtttct gtcccaagtc aagattccga aaacgatcac cgtcagcacc    1080
ggctttatgt ctattatgca ccagaaacgc acggctatgt tcaagatcc acaagagcga    1140 cccagaaaac tgcctcagct gtgtacagaa ctgcaaacaa ccatccatga catcattctt    1200
gagtgtgttt attgcaagca acagctcgag gacgaaatcg atggacctgc tggacaggcc    1260
gaacccgata gggctcacta caacatcgtc acgttttgtt gcaagtgtga ctccacccctg   1320 agactgtgtg tgcagtctac ccatgtggat atcagaaccc tcgaggacct gctcatggga    1380
acactcggta ttgtgtgtcc tatctgctcc cagaagcctg aacaactct cgagcaacag    1440 tacaacaagc cgctctgtga tctcctgatc agatgcatta actgtcagaa gcctctctgc    1500
cctgaagaga agcagagaca cctcgataag aaacagcgct tcacaatat cagaggccgg    1560 tggaccggca gatgcatgtc ctgctgtcgg agcagcagaa ccagacgcga gacacagatg    1620
catggcgata cacctacact ccatgagtat atgctcgatc tccagcctga aaccaccgat    1680
ctctactgtt atgagcagct caatgacagc agcgaagagg aagatgagat tgacggacca    1740
gctgggcaag ccgagccaga tcgcgcacat acaatatcg ttaccttttg ttgtcagctc    1800
tgcacagagt tgcaaacgac gattcacgac attatattgg agtgcgtgta ctgtaaacaa    1860
cagctgctgc ggagagaagt ctacgatttc gcctttagag atctctgcat cgtctacaga    1920
gatgggaatc cctatgccgt ctgtgataag tgtctcaagt tttactccaa gatctccgag    1980
tatcgccatt actgttactc cctgtacggg acaaccttgg agcagcagta taacaagcca    2040
ttgtgtgatc tgctcattcg gtgtattaac tgccaaaagt gatga                    2085
```

<210> SEQ ID NO 25
<211> LENGTH: 2094
<212> TYPE: DNA
<213> ORGANISM: Artificial Sequence
<220> FEATURE:
<223> OTHER INFORMATION: nucleotide sequence encoding HPV16 E2E6E7SH
      designer polypeptide

<400> SEQUENCE: 25

```
atgcagacgc cgaaagaaac cctgtccgag agactgagcg ctctccaaga taagattatt    60
gatcactatg agaatgactc caaggacatt gattcccaga ttcagtattg gcaacttatt    120
cgctgggaaa atgccatctt ctttgccgct cgggaacacg ggattcagac actgaatcat    180
caagtggtcc cagcctacaa tatctccaag tccaaagccc acaaagctat cgaactccaa    240
atggctctcc aggactggc tcagtccgct tataagacag aagattggac actccaggac    300
acgtgtgaag aactctggaa taccgaaccg acgcactgtt ttaagaaggg tggacagaca    360
```

```
gttcaagtct actttgatgg gaacaaagat aattgcatga catatgtcgc ttgggattcc      420
gtctactata tgacagatgc tgggacgtgg gataagacag ccacatgcgt cagccacaga      480
gggctgtact atgtcaaaga agggtataat acgttctata tcgagtttaa gtctgaatgc      540
gagaaatatg gaatacggg aacctgggaa gtgcattttg gaacaatgt catcgattgc        600 aatgactcca tgtgctccac ctccgatgac acagtcagcg ccacacagct cgtgaaacag      660
ctccagcata caccatctcc ctactcctcc actgtgtccg tgggaacagc caaaacatat      720
ggacagacct ccgctgccac acggcctggc cattgcggac tggccgagaa acagcattgt      780
ggaccagtca accctctgct gggagctgct actccaacag gaacaacaa gaggcggaaa       840 ctgtgttccg gcaatacgac acctatcatt cacctcaagg tcgacagaaa ctccctgatg      900
agactgagat accggctgag aaagcactcc gatcactaca gagatatcag ctctacttgg      960
cattggacag gtgctggaaa cgaaaagaca gggatcctga cagtgacgta tcactccgag     1020
actcagcgca ccaaatttct caatactgtg gccattcccg attccgtgca gattcttgtc     1080
ggatatatga cgatgatggc tcgctttgag gatcctacaa gaaggcctta taagctccct     1140
gatctctgca ctgagcttaa caccagcctg caagacattg aaatcacttg tgtctattgc     1200
aaaacggtcc tggacctcct ctgtcacgaa caactgtctg atagtgaaga ggagaatgat     1260
gagatcgatg tgtcaacca ccagcacctc cctgctcgga gagccgagcc tcagcggcat      1320
acaatgctct gtatgtgttg taaatgcgag gccagaatcg aactcgtggt cgagtcctcc     1380
gccgacgatc tgagagcttt tcagcaactg tttctcaaca ccctgtcctt tgtctgtcct     1440
tggtgtgcct cccagcatta ctccgattct gtgtatggcg acactctcga aagctcact     1500 aacacgggac tgtataatct gctcatccgc tgtctgagat gccagaaacc tctgaatcct     1560
gccgagaaac tgcgccacct caatgagaag agaagattcc acaacattgc cggacattat      1620
cgaggccagt gtcactcctg ctgtaacaga gctcggcaag agagactgca gagaaggcgc     1680
gagacaatgc acggacctaa agccaccctc caggacattg tgctgcatct cgagcctcag     1740
aatgagattc ctgtcgactt gctctgccat gagcaactgt ccgattctga ggaagaaaat     1800
gacgaaatag atggcgtgaa ccctgacttg tgcactgaac tcaatacttc cctgcaagat     1860
atagagataa cgtgcgttta ctgtaagacg gtcctcgaac tcaccgaagt ctttgagttt     1920
gcctttaagg atctctttgt cgtctaccgc gactccatcc ctcacgctgc ttgtcacaaa     1980
tgtatcgatt tttactctcg catcagagaa ctgcggcact actctgactc agtgtatggc     2040
gatactttgg agaagcttac caatacgggc ctctataact tgctgatctg atga           2094
```

<210> SEQ ID NO 26
<211> LENGTH: 124
<212> TYPE: DNA
<213> ORGANISM: Artificial Sequence
<220> FEATURE:
<223> OTHER INFORMATION: PrMVA Promoter

<400> SEQUENCE: 26

```
taaaaataga aactataatc atataatagt gtaggttggt agtattgctc ttgtgactag       60
agactttagt taaggtactg taaaaataga aactataatc atataatagt gtaggttggt      120
agta                                                                   124
```

<210> SEQ ID NO 27
<211> LENGTH: 227
<212> TYPE: DNA

-continued

```
<213> ORGANISM: Artificial Sequence
<220> FEATURE:
<223> OTHER INFORMATION: PrHyb Promoter

<400> SEQUENCE: 27
gttttgaaaa ttttttttata ataaatatcc ggtaaaaatt gaaaaactat tctaatttat      60
tgcacggtcc ggtaaaaatt gaaaaactat tctaatttat tgcacggtcc ggtaaaaatt     120
gaaaaactat tctaatttat tgcacggtcc ggtaaaaatt gaaaaactat tctaatttat     180
tgcacggtcc ggtaaaaatt gaaaaactat tctaatttat tgcacgg                   227

<210> SEQ ID NO 28
<211> LENGTH: 365
<212> TYPE: PRT
<213> ORGANISM: Artificial Sequence
<220> FEATURE:
<223> OTHER INFORMATION: HPV 16 E2 fragment

<400> SEQUENCE: 28
```

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Val Asp Ala Asn Thr Leu Met Arg Leu Arg Tyr Arg

```
                290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
                340                 345                 350

Pro Lys Thr Ile Thr Val Ser Thr Gly Phe Met Ser Ile
                355                 360                 365

<210> SEQ ID NO 29
<211> LENGTH: 1095
<212> TYPE: DNA
<213> ORGANISM: Artificial Sequence
<220> FEATURE:
<223> OTHER INFORMATION: nt sequence encoding HPV 16 E2 fragment

<400> SEQUENCE: 29
atggaaaccc tgtgccagcg gctgaacgtg tgccaggaca agatcctgac ccactacgag      60
aacgacagca ccgacctgcg ggaccacatc gactactgga agcacatgcg gctggaatgc     120
gccatctact acaaggccag agagatgggc ttcaagcaca tcaaccacca ggtggtgccc     180
accctggccg tgtccaagaa caaggccctg caggccatcg agctgcagct gaccctggaa     240
accatctaca cagccagta cagcaacgag aagtggaccc tgcaggacgt gtccctggaa      300
gtgtacctga ccgctcccac cggctgcatc aagaaacacg gctacaccgt ggaagtgcag     360
ttcgacggcg acatctgcaa caccatgcac tacaccaact ggacccacat ctacatctgc     420
gaagaggcca gcgtgaccgt ggtggaaggc caggtggact actacggcct gtactacgtg     480
cacgagggca tccggaccta cttcgtgcag ttcaaggacg acgccgagaa gtacagcaag     540
aacaaagtgt gggaggtgca cgctggcggc caggtcatcc tgtgccccac cagcgtgttc     600
agcagcaacg aggtgtccag ccccgagatc atccggcagc acctggccaa tcaccctgcc     660
gccacccaca caaaggccgt ggccctgggc accgaggaaa cccagaccac catccagcgg     720
cccgaaagcg agcccgacac cggcaatccc tgccacacca ccaagctgct gcaccgggac     780
agcgtggaca gcgcccctat cctgaccgcc ttcaacagca gccacaaggg ccggatcaac     840
tgcaacagca caccaccccc catcgtgcac ctgaaggtgg acgccaacac cctgatgcgg     900
ctgcggtaca gattcaagaa gcactgcacc ctgtacaccg ccgtgtcctc cacctggcac     960
tggaccggcc acaacgtgaa gcacaagagc gccatcgtga ccctgaccta cgacagcgag    1020
tggcagcggg accagttcct gagccaggtc aaaatcccca gaccatcac cgtgtccacc     1080 ggcttcatga gcatc                                                    1095

<210> SEQ ID NO 30
<211> LENGTH: 1095
<212> TYPE: DNA
<213> ORGANISM: Artificial Sequence
<220> FEATURE:
<223> OTHER INFORMATION: nucleotide sequence encoding HPV 16 E2 fragment

<400> SEQUENCE: 30
atggaaacgc tctgccagag actcaatgtc tgccaggata agattctcac gcattatgag      60
aacgattcca cggacctgcg cgatcacatt gattattgga aacacatgcg ccttgagtgt     120
gctatctatt ataaggctcg cgaaatgggt ttcaaacata tcaatcatca ggtcgtccct     180
accctcgccg tcagcaaaaa caaagctctg caggctattg aactccagct caccctcgag     240
```

```
acaatctaca attcccagta ctccaatgag aaatggacgc tccaggatgt gtctctcgag    300
gtctacctga cagctcctac aggatgtatt aagaaacacg ggtacacggt ggaagtccag    360
tttgatggcg atatatgtaa taccatgcat tatacgaatt ggacgcatat ctatatttgt    420
gaagaggcct ctgtgacagt ggtcgaggga caggtcgact attatgggct gtattatgtg    480
cacgaaggga tcagaacata ctttgtccag tttaaggatg atgctgagaa gtattctaag    540
aacaaagttt gggaagtcca tgccggtgga caagtgattc tgtgtcctac ctccgtgttc    600
agctctaatg aggtgtcctc tccagagatc attagacagc atctggccaa ccatcctgct    660
gctacacata ccaaggctgt ggctctggga acagaagaga cacagacaac aatccagagg    720
cctcggagcg agcctgatac aggcaaccct tgtcacacaa caaaactgct gcacagagac    780
tccgtggact ccgctcctat tctgacagcc tttaactcct cccacaaagg gagaatcaat    840
tgcaattcca ataccacgcc gatcgtccac ctcaaagtgg atgctaatac tctcatgcgg    900
ctccgctacc gcttcaagaa acactgtaca ctgtatacag ctgtgtccag cacatggcat    960
tggacgggac acaatgtgaa acataagtcc gccatcgtca cgctcacata cgattccgag   1020
tggcagagag atcagtttct gtcccaagtc aagattccga aaacgatcac cgtcagcacc   1080
ggctttatgt ctatt                                                    1095
```

<210> SEQ ID NO 31
<211> LENGTH: 365
<212> TYPE: PRT
<213> ORGANISM: Artificial Sequence
<220> FEATURE:
<223> OTHER INFORMATION: HPV 18 E2 fragment

<400> SEQUENCE: 31

```
Met Gln Thr Pro Lys Glu Thr Leu Ser Glu Arg Leu Ser Ala Leu Gln
1               5                   10                  15

Asp Lys Ile Ile Asp His Tyr Glu Asn Asp Ser Lys Asp Ile Asp Ser
            20                  25                  30

Gln Ile Gln Tyr Trp Gln Leu Ile Arg Trp Glu Asn Ala Ile Phe Phe
        35                  40                  45

Ala Ala Arg Glu His Gly Ile Gln Thr Leu Asn His Gln Val Val Pro
    50                  55                  60

Ala Tyr Asn Ile Ser Lys Ser Lys Ala His Lys Ala Ile Glu Leu Gln
65                  70                  75                  80

Met Ala Leu Gln Gly Leu Ala Gln Ser Ala Tyr Lys Thr Glu Asp Trp
                85                  90                  95

Thr Leu Gln Asp Thr Cys Glu Glu Leu Trp Asn Thr Glu Pro Thr His
            100                 105                 110

Cys Phe Lys Lys Gly Gly Gln Thr Val Gln Val Tyr Phe Asp Gly Asn
        115                 120                 125

Lys Asp Asn Cys Met Thr Tyr Val Ala Trp Asp Ser Val Tyr Tyr Met
    130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
            180                 185                 190

Phe Gly Asn Asn Val Ile Asp Cys Asn Asp Ser Met Cys Ser Thr Ser
        195                 200                 205
```

```
Asp Asp Thr Val Ser Ala Thr Gln Leu Val Lys Gln Leu Gln His Thr
        210                 215                 220

Pro Ser Pro Tyr Ser Ser Thr Val Ser Val Gly Thr Ala Lys Thr Tyr
225                 230                 235                 240

Gly Gln Thr Ser Ala Ala Thr Arg Pro Gly His Cys Gly Leu Ala Glu
                245                 250                 255

Lys Gln His Cys Gly Pro Val Asn Pro Leu Leu Gly Ala Ala Thr Pro
                260                 265                 270

Thr Gly Asn Asn Lys Arg Arg Lys Leu Cys Ser Gly Asn Thr Thr Pro
        275                 280                 285

Ile Ile His Leu Lys Val Asp Arg Asn Ser Leu Met Arg Leu Arg Tyr
        290                 295                 300

Arg Leu Arg Lys His Ser Asp His Tyr Arg Asp Ile Ser Ser Thr Trp
305                 310                 315                 320

His Trp Thr Gly Ala Gly Asn Glu Lys Thr Gly Ile Leu Thr Val Thr
                325                 330                 335

Tyr His Ser Glu Thr Gln Arg Thr Lys Phe Leu Asn Thr Val Ala Ile
                340                 345                 350

Pro Asp Ser Val Gln Ile Leu Val Gly Tyr Met Thr Met
        355                 360                 365

<210> SEQ ID NO 32
<211> LENGTH: 1095
<212> TYPE: DNA
<213> ORGANISM: Artificial Sequence
<220> FEATURE:
<223> OTHER INFORMATION: nucleotide sequence encoding HPV 18 E2 fragment

<400> SEQUENCE: 32
atgcagaccc ccaaagagac actgagcgag cggctgagcg ccctgcagga caagatcatc      60
gaccactacg agaacgacag caaggacatc gacagccaga tccagtactg cagctgatc     120 agatgggaga cgccatcttt cttcgccgcc agagagcacg gcatccagac cctgaaccac    180
caggtggtgc ccgcctacaa catcagcaag agcaaggccc acaaggctat cgagctgcag    240 atgccctgc agggactggc ccagagcgcc tacaagaccg aggactggac cctgcaggat     300
acctgcgagg aactgtggaa caccgagccc acccactgct tcaagaaagg cggccagacc    360
gtgcaggtgt acttcgacgg caacaaggac aactgcatga cctacgtggc ctgggacagc    420
gtgtactaca tgaccgacgc cggcacctgg acaagaccg ccacctgtgt gtcccaccgg     480
ggcctgtact acgtgaaaga gggctacaac accttctaca tcgagttcaa gagcgagtgc    540
gagaagtacg gcaacaccgg cacatgggag gtgcacttcg caacaacgt gatcgactgc    600 aacgacagca tgtgcagcac cagcgacgac accgtgtccg ccacccagct ggtgaaacag    660
ctgcagcaca ccccccagcc ctacagcagc accgtgtctg tgggcaccgc caagacctac    720
ggccagacca gcgccgccac cagacctgga cactgtggcc tggccgagaa gcagcactgc    780
ggccctgtga accctctgct gggagccgcc accccaccg caacaacaa gcggagaaag     840 ctgtgcagcg gcaacaccac ccccatcatc cacctgaagg tggaccggaa cagcctgatg    900
cggctgcggt acagactgcg gaagcacagc gaccactacc gggacatcag cagcacctgg    960
cactggaccg gcgctggcaa cgagaaaacc ggcatcctga ccgtgaccta ccacagcgaa   1020
acccagcgga ccaagttcct gaacaccgtg gccatccccg acagcgtgca gatcctggtg   1080
ggatatatga ccatg                                                   1095
```

<210> SEQ ID NO 33
<211> LENGTH: 1095
<212> TYPE: DNA
<213> ORGANISM: Artificial Sequence
<220> FEATURE:
<223> OTHER INFORMATION: nucleotide sequence encoding HPV 18 E2 fragment

<400> SEQUENCE: 33

```
atgcagacgc cgaaagaaac cctgtccgag agactgagcg ctctccaaga taagattatt      60
gatcactatg agaatgactc caaggacatt gattcccaga ttcagtattg gcaacttatt     120
cgctgggaaa atgccatctt ctttgccgct cgggaacacg ggattcagac actgaatcat     180
caagtggtcc cagcctacaa tatctccaag tccaaagccc acaaagctat cgaactccaa     240
atggctctcc agggactggc tcagtccgct tataagacag aagattggac actccaggac     300
acgtgtgaag aactctggaa taccgaaccg acgcactgtt ttaagaaggg tggacagaca     360
gttcaagtct actttgatgg gaacaaagat aattgcatga catatgtcgc ttgggattcc     420
gtctactata tgacagatgc tgggacgtgg gataagacag ccacatgcgt cagccacaga     480
gggctgtact atgtcaaaga agggtataat acgttctata tcgagtttaa gtctgaatgc     540
gagaaatatg gaatacggg aacctgggaa gtgcattttg ggaacaatgt catcgattgc     600
aatgactcca tgtgctccac ctccgatgac acagtcagcg ccacacagct cgtgaaacag     660
ctccagcata caccatctcc ctactcctcc actgtgtccg tgggaacagc caaaacatat     720
ggacagacct ccgctgccac acggcctggc cattgcggac tggccgagaa acagcattgt     780
ggaccagtca accctctgct gggagctgct actccaacag gaacaacaa gaggcggaaa      840
ctgtgttccg gcaatacgac acctatcatt cacctcaagg tcgacagaaa ctccctgatg     900
agactgagat accggctgag aaagcactcc gatcactaca gagatatcag ctctacttgg     960
cattggacag gtgctggaaa cgaaaagaca gggatcctga cagtgacgta tcactccgag    1020
actcagcgca ccaaatttct caatactgtg gccattcccg attccgtgca gattcttgtc    1080
ggatatatga cgatg                                                     1095
```

THERAPEUTIC HPV VACCINE COMBINATIONS

CROSS REFERENCE TO RELATED APPLICATIONS

This application is a Section 371 of International Application No. PCT/US2017/030338, filed on May 1, 2017, which published in the English Language on Nov. 9, 2017, under International Publication No. WO 2017/192418, which is entitled to priority pursuant to 35 U.S.C. § 119(e) to U.S. Provisional Patent Application No. 62/330,562, filed May 2, 2016, and to U.S. Provisional Patent Application No. 62/447,094 filed Jan. 17, 2017, the disclosures of which are herein incorporated by reference in their entirety.

FIELD OF THE INVENTION

The invention relates to the field of medicine and more in particular to nucleic acid constructs, polypeptides, vectors, vaccines, vaccine combinations that can be used as therapeutics against human papillomavirus type 18, and/or type 16.

REFERENCE TO SEQUENCE LISTING SUBMITTED ELECTRONICALLY

This application contains a sequence listing, which is submitted electronically via EFS-Web as an ASCII formatted sequence listing with a file name "Sequence_Listing_688097-124U1", creation date of Nov. 1, 2018, and having a size of about 64.5 kB. The sequence listing submitted via EFS-Web is part of the specification and is herein incorporated by reference in its entirety.

BACKGROUND OF THE INVENTION

The family of human papillomaviruses (HPVs) consist of more than 100 types (also referred to as subtypes) that are capable of infecting keratinocytes of the skin or mucosal membranes. Over 40 types of HPV are typically transmitted through sexual contact and HPV infections of the anogenital region are very common in both men and women. Some sexually transmitted HPV types may cause genital warts. Persistent infections with "high-risk" HPV types (e.g. types 16, 18, 31, 45)—different from the ones that cause skin warts—may progress to precancerous lesions and invasive cancer, e.g. of the cervix, vulva, vagina, penis, oropharynx and anus. The majority of HPV infections are spontaneously cleared within one to two years after infection. In healthy individuals circulating Th1- and Th2-type CD4+ T-cells specific for the viral early proteins E2, E6 and E7 of HPV-16 as well as E6-specific CD8+ T-cells, migrate into the skin upon antigenic challenge, indicating that successful defense against HPV-16 infection is commonly associated with a systemic effector T-cell response against these viral early antigens. In a minority (~1%) of infected individuals, HPV infection persists, ultimately resulting in genital neoplastic lesions. Among the high-risk HPVs, HPV16 and HPV18 are the main causes of cervical cancer, together causing about 70% of the cases, and these two types also play a major role in other HPV-induced cancers such as anal and oropharyngeal cancer. Worldwide, HPV is one of the most important infectious agents causing cancer.

Vaccination against HPV is deemed a feasible strategy to reduce the incidence or effects of infection by HPV (van der Burg and Melief, 2011, *Curr Opinion Immunol* 23: 252-257).

Prophylactic HPV vaccines based on virus like particles (VLPs) formed by the (envelope) protein L1 of the HPV types 16 and 18, are very efficient in the prevention of persistent infection and the associated disease by HPV16 and HPV18. These vaccines are believed to provide sterile immunity via the induction of neutralizing antibodies against the L1 proteins. Addition of L1-based VLPs from additional high-risk HPV types may further increase the breadth of protection conferred by such vaccines.

However, while such vaccines can prevent initial infection (i.e., they result in prophylaxis), there is no evidence of a beneficial effect on established genital lesions caused by HPV16 and HPV18, so they are not considered therapeutic vaccines against HPV (Hildesheim et al., 2007, *JAMA* 298: 743-53).

Despite the introduction of these prophylactic vaccines, large numbers of people have already obtained or are still at risk of obtaining persistent high-risk HPV infections and, therefore, are at risk of getting cancer. Therapeutic vaccines for the eradication of established HPV infections and associated diseases are an urgent unmet medical need.

Some attempts to address this need have been described. For example, clinical trials have been carried out with a variety of different vaccination strategies, such as a fusion protein consisting of a heat shock protein (Hsp) from *Mycobacterium bovis* and HPV-16 E7 or a fusion protein of E6, E7 and L2 from HPV-16 and HPV-18, chimeric L1-E7 VLPs, recombinant vaccinia viruses expressing either E6 and E7 of HPV-16 and HPV-18 or bovine papilloma virus E2, DNA vaccines expressing CTL epitopes of E6 and E7 of HPV-16 and HPV-18, a live-attenuated *Listeria monocytogenes* (Lm) that secretes the HPV-16 E7 antigen, and synthetic long-peptides (SLPs) comprising HPV-16 E6 and E7 peptides. While some of these approaches show some, but limited, clinical efficacy, most have failed, demonstrating that improvement of the current strategies is needed.

Integration of the genes encoding the early HPV proteins E6 and E7 is a necessary step in the process from infection to cancer and continuous expression of E6 and E7 is required for the maintenance of the neoplastic phenotype of cervical cancer cells. E6 and E7 are therefore considered good targets for therapeutic vaccination. As mentioned some studies have shown that therapeutic vaccination of women infected with high-risk HPV can induce regression of existing lesions. Kenter et al showed a durable and complete regression in 47% of patients having Vulvar Intraepithelial Neoplasia (VIN) using SLPs derived from the HPV16 E6 and E7 proteins and an adjuvant as a therapeutic vaccine (Kenter et al., 2009, *N Engl J Med* 361: 1838-47). Similarly, a study in which a protein-based vaccine (TA-CIN, consisting of a fusion protein of HPV16 E6, E7 and L2) was combined with local immune modulation in VIN 2/3 patients, showed complete regression in 63% of patients (Daayana et al., 2010, *Br J Cancer* 102: 1129-36). Possible drawbacks of the synthetic long peptides as a vaccine include manufacturability at large scale and costs associated therewith, the need for potentially reactogenic adjuvant and the associated adverse effects associated with immunization (especially pain and swelling). Due to the high level of discomfort it is not likely that SLPs will be used in early stage disease when the spontaneous clearance rate is still high. Similarly, due to the need for local imiquimod treatment in the case of TA-CIN treatment, tolerability is a significant issue as the majority of women experience local and systemic side effects lasting for the duration of imiquimod treatment, which may affect daily activities.

A possible alternative is to use nucleic acid based vaccination such as DNA vaccines or viral vectored vaccines encoding the HPV E6 and/or E7 protein for vaccination.

However, the HPV E6 and E7 proteins have oncogenic potential and thus vaccination with vaccines that comprise nucleic acids encoding these proteins poses a risk of inducing cellular transformation due to the possibility of prolonged expression of the antigens.

Therefore, in case of genetic vaccination, non-oncogenic/detoxified versions of E6 and/or E7 can be used in order to exclude any risk of cellular transformation due to the vaccination. Loss of oncogenic potential of wild-type E6 and E7 is commonly achieved by deletion and/or substitution of residues known to be important for the function of these proteins (e.g., Smahel et al., 2001, *Virology* 281:231-38; Yan et al., 2009, *Vaccine* 27: 431-40; Wieking et al., 2012, *Cancer Gene Ther* 19: 667-74). However, a disadvantage of these approaches is that they carry the risk of removing important T-cell epitopes from and/or introducing new undesired T-cell epitopes into the proteins, and may thus not lead to the desired immune response.

In an alternative strategy to remove the oncogenic potential of HPV16 E6 and E7, shuffled versions (i.e. polypeptides wherein fragments of the wild-type protein are re-ordered) of the E6 and E7 proteins have been constructed (e.g. Öhlschläger et al., 2006, *Vaccine* 24: 2880-93; Oosterhuis et al., 2011, *Int J Cancer* 129: 397-406; Oosterhuis et al., 2012, *Hum Gen Ther* 23: 1301-12). However, these approaches would still require manufacturing, formulation and administration of multiple molecules to ensure inclusion of all possible epitopes of both the E6 and E7 proteins, resulting in sub-optimal logistics and relatively high costs, and moreover the strategies described introduce potentially strong non-natural epitopes that are not present in E6 and E7 and since immune responses could be diverted from relevant E6/E7 epitopes towards such non-natural epitopes, the described constructs may not have the optimal immunological characteristics. A therapeutic DNA vaccine expressing an intracellularly targeted fusion protein with built-in genetic adjuvant and shuffled fragments of E6 and E7 of both HPV16 and HPV18 has also been described, and electroporation-enhanced immunization therewith elicited a significant E6/E7-specific T-cell response in CIN3 patients (Kim et al., 2014).

There remains a need in the art for therapeutic vaccines against HPV, preferably having less of the drawbacks of the approaches described before.

SUMMARY OF THE INVENTION

The present invention provides one or more vectors, vaccines, and vaccine combinations that can be used for generating an immune response against HPV infections. In various embodiments, the present invention comprises nucleic acid molecules that encode polypeptides, or fusion proteins, that comprise essentially all possible T-cell epitopes of HPV16 or HPV18 oncoproteins E6 and E7, but nevertheless have a strongly reduced (as compared to wt E6 and E7), up to non-detectable, transforming activity, by comprising fragments of the E6 and E7 proteins that have been re-ordered, while at the same time containing a minimized number of undesired strong neo-epitopes. This is in contrast to molecules previously reported by others. The invention provides molecules that can be used in therapeutic vaccines against either HPV16 or HPV18.

In various additional embodiments, the vectors, vaccines, and vaccine combinations comprise nucleic acid molecules that encode polypeptides, or fusion proteins, that comprise essentially all possible T-cell epitopes of HPV16 or HPV18 oncoproteins E6 and E7, but nevertheless have a strongly reduced (as compared to wt E6 and E7), up to non-detectable transforming activity. At least in one aspect this is accomplished as the vectors, vaccines, and vaccine combinations comprise fragments of the E6 and E7 proteins that have been re-ordered, while at the same time containing a minimized number of undesired strong neo-epitopes. This is in contrast to molecules previously reported by others. In preferred embodiments, the polypeptides or fusion proteins encoded by the vectors, vaccines or vaccine combinations further comprise E2 protein or fragments thereof of HPV16 or HPV18. The invention provides molecules that can be used in therapeutic vaccines against either HPV16 or HPV18. Such molecules can also be combined in therapeutic vaccines against both HPV16 and HPV18.

In certain embodiments, the invention for HPV16 provides vectors, vaccines, and vaccine combinations comprising a nucleic acid molecule encoding a polypeptide comprising the amino acid sequence as set forth in SEQ ID NO: 1, SEQ ID NO: 3, SEQ ID NO:5, SEQ ID NO: 28, or combinations thereof. In certain preferred embodiments, the invention for HPV16 provides vectors, vaccines, and vaccine combinations comprising a nucleic acid molecule encoding a polypeptide comprising the amino acid sequence as set forth in SEQ ID NO: 3. In other embodiments, for HPV18, the invention provides vectors, vaccines, and vaccine combinations comprising a nucleic acid molecule encoding a polypeptide comprising the amino acid sequence as set forth in SEQ ID NO: 20, SEQ ID NO: 22, SEQ ID NO: 31, or combinations thereof. In certain preferred embodiments, for HPV18, the invention provides vectors, vaccines, and vaccine combinations comprising a nucleic acid molecule encoding a polypeptide comprising the amino acid sequence as set forth in SEQ ID NO: 22.

In some aspects, the encoded polypeptide of the invention can further comprise a leader sequence.

In certain embodiments, the encoded polypeptide comprises at least one epitope of an HPV16 E2 protein or an HPV18 E2 protein. The E2 protein can be inactivated in for instance its transactivation and/or DNA binding domain, e.g. by deletion, mutation or by structural rearrangement of different parts of the protein. In certain embodiments for HPV16, the encoded polypeptide comprises the amino acid sequence as set forth in SEQ ID NO: 28. In certain embodiments for HPV18, the encoded polypeptide comprises the amino acid sequence as set forth in SEQ ID NO: 31.

In certain embodiments, for HPV16, the nucleic acid sequence comprises the polynucleotide sequence as set forth in SEQ ID NO: 2, SEQ ID NO: 4, SEQ ID NO: 6, SEQ ID NO: 24, SEQ ID NO: 29, SEQ ID NO: 30, or combinations thereof. In certain preferred embodiments, for HPV16, the nucleic acid sequence comprises the polynucleotide sequence as set forth in SEQ ID NO: 2, SEQ ID NO: 4, or SEQ ID NO: 24.

In certain other embodiments, for HPV18, the nucleic acid sequence comprises the polynucleotide sequence as set forth in SEQ ID NO: 21, SEQ ID NO: 23, SEQ ID NO:25, SEQ ID NO: 32, SEQ ID NO: 33, or combinations thereof. In certain preferred embodiments, for HPV18, the nucleic acid sequence comprises the polynucleotide sequence as set forth in SEQ ID NO: 21, SEQ ID NO: 23, or SEQ ID NO: 25.

The invention also provides a vaccines, and vaccine combinations comprising a recombinant virus vector according to the invention, and a pharmaceutically acceptable excipient. The recombinant virus vector comprises one or more nucleic acid molecules according to the invention, wherein the sequence encoding the polypeptide is operably linked to a promoter.

In certain embodiments the vector is a viral vector, such as an recombinant poxviral vector or a recombinant adenoviral vector. In certain preferred embodiments, the vector is a recombinant adenovirus or a recombinant MVA virus. In additional preferred embodiments, the MVA virus vector is MVA-BN or derivatives thereof. In still additional preferred embodiments, the adenoviral vector is selected from rAd26 and rAd35, and most preferably it is rAd26.

In certain preferred embodiments, there is a vaccine combination comprising:

a) a first vaccine comprising an immunologically effective amount of one or more recombinant adenovirus vectors together comprising a first nucleic acid encoding a first polypeptide comprising the amino acid sequence of SEQ ID NO: 1 and a second nucleic acid encoding a second polypeptide comprising the amino acid sequence of SEQ ID NO: 20, together with a pharmaceutically acceptable carrier; and b) a second vaccine comprising an immunologically effective amount of a recombinant Modified Vaccinia Ankara (MVA) vector comprising a third nucleic acid encoding a third polypeptide comprising the amino acid sequence of SEQ ID NO: 1 and a fourth nucleic acid encoding a fourth polypeptide comprising the amino acid sequence of SEQ ID NO: 20, together with a pharmaceutically acceptable carrier;

wherein the MVA vector comprises MVA-BN or derivatives thereof.

According to embodiments of the invention, the first polypeptide and the third polypeptide can be identical or different. For example, one of the first and third polypeptides can contain an additional amino acid sequence that is absent from the other polypeptide, or the first and third polypeptides can contain additional amino acid sequences that are different from each other. Similarly, the second and the fourth polypeptides can be identical or different. The first nucleic acid and the third nucleic acid can be identical or different. For example, the first and third nucleic acids can be different because they encode different first and third polypeptides, and/or use different codons for the same amino acids. Similarly, the second and fourth nucleic acids can be identical or different.

In certain additional preferred embodiments, the first vaccine and the second vaccine of both a) and b) each further comprise a nucleic acid encoding a fifth polypeptide comprising the amino acid sequence of SEQ ID NO: 28 and a nucleic acid encoding a sixth polypeptide comprising the amino acid sequence of SEQ ID NO: 31. The fifth and the sixth polypeptides can each be expressed independently or preferably as a part of a fusion protein that contains an E6 and E7 polypeptide of the invention.

In other additional preferred embodiments, the nucleic acid encoding the polypeptide comprising the amino acid sequence of SEQ ID NO:1 of each of the first vaccine and second vaccine further encodes the fifth polypeptide. Preferably, the polypeptide comprising the amino acid sequence of SEQ ID NO:1 and the fifth polypeptide are expressed together in a fusion protein, such as a polypeptide comprising the amino acid sequence of SEQ ID NO:3 or SEQ ID NO:5. The nucleic acid encoding the polypeptide comprising the amino acid sequence of SEQ ID NO: 20 of each of the first and second vaccines preferably further encodes the sixth polypeptide. Preferably, the polypeptide comprising the amino acid sequence of SEQ ID NO:20 and the sixth polypeptide are expressed together in a fusion protein, such as a polypeptide comprising the amino acid sequence of SEQ ID NO:22.

In still other preferred embodiments, the nucleic acid encoding the polypeptide comprising SEQ ID NO:1 of one or both the first vaccine and second vaccine is part of a nucleic acid encoding a polypeptide comprising SEQ ID NO: 3. In still additional preferred embodiments, the nucleic acid encoding the polypeptide comprising SEQ ID NO: 20 of one or both the first vaccine and second vaccine is part of a nucleic acid encoding a polypeptide comprising SEQ ID NO: 22.

In various embodiments, the nucleic acid encoding a polypeptide comprising the amino acid sequence of SEQ ID NO: 1 has at least 90% sequence identity to the polynucleotide sequence of SEQ ID NO: 2 and the nucleic acid encoding a polypeptide comprising the amino acid sequence of SEQ ID NO: 20 has at least 90% sequence identity to the polynucleotide sequence of SEQ ID NO: 21. In other embodiments, the nucleic acid encoding a polypeptide comprising the amino acid sequence of SEQ ID NO: 3 has at least 90% sequence identity to the polynucleotide sequence of SEQ ID NO: 4 or SEQ ID NO: 24 and the nucleic acid encoding a polypeptide comprising the amino acid sequence of SEQ ID NO: 22 has at least 90% sequence identity to the polynucleotide sequence of SEQ ID NO: 23 or SEQ ID NO: 25.

The invention also provides a method of inducing an immune response against HPV, in particular HPV16 or HPV18, or HPV16 and HPV18 in a subject in need thereof, the method comprises administering to the subject a vector, vaccine, or vaccine combination according to the invention. The invention also provides a vector, vaccine, or vaccine combination according to the invention for use in inducing an immune response against HPV, in particular HPV16 or HPV18, or both HPV16 and HPV18 in a subject in need thereof.

In certain embodiments, the vectors or vaccines of the present invention are administered to the subject more than once.

In certain embodiments, the vector, vaccine, or vaccine combination according to the invention are administered to a subject in need thereof, preferably a human subject, as a prime-boost regimen. In a preferred embodiment, the prime-boost regimen comprises a priming vaccine comprising an immunologically effective amount of either (i) a recombinant adenovirus vector comprising a nucleic acid encoding a polypeptide according to the invention, together with a pharmaceutically acceptable carrier; or (ii) a first recombinant adenovirus vector comprising a nucleic acid encoding a polypeptide according to the invention and a second recombinant adenovirus vector comprising a nucleic acid encoding a different polypeptide according to the invention, together with a pharmaceutically acceptable carrier. There is also a boosting vaccine comprising an immunologically effective amount of a recombinant Modified Vaccinia Ankara (MVA) vector comprising a nucleic acid encoding a polypeptide according to the invention, preferably encoding two different polypeptides according to the invention, together with a pharmaceutically acceptable carrier.

In other various embodiments, the prime-boost regimen comprises a priming vaccine comprising an immunologically effective amount of a recombinant Modified Vaccinia Ankara (MVA) vector comprising a nucleic acid encoding a polypeptide according to the invention, together with a pharmaceutically acceptable carrier. There is also a boosting vaccine comprising an immunologically effective amount of either (i) a recombinant adenovirus vector comprising a nucleic acid encoding a polypeptide according to the invention, together with a pharmaceutically acceptable carrier; or (ii) a first recombinant adenovirus vector comprising a nucleic acid encoding a polypeptide according to the invention and a second recombinant adenovirus vector comprising a nucleic acid encoding a different polypeptide according to the invention, together with a pharmaceutically acceptable carrier.

The invention also provides a method for treating any of: persistent HPV infection (in particular persistent HPV16 or HPV18 infection), vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC)), oropharyngeal cancer, penile cancer, vaginal cancer or anal cancer in a subject in need thereof, the method comprises administering to the subject a vector, vaccine, or vaccine combination according to the invention. The invention also provides a vector, vaccine, or vaccine combination according to the invention for use in treatment of any of: persistent HPV infection (in particular persistent HPV16 or HPV18 infection), vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC)), oropharyngeal cancer, penile cancer, vaginal cancer or anal cancer in a subject in need thereof.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

FIG. 24H shows the number of antigens per animal per time point. The cut-off was set to 50 SFU per $1*10^6$ PBMCs. FIG. 24I shows the cumulative responses for all six tested peptide pools at different time points. Statistical analysis for panel B-H: Wilcoxon Signed Rank test comparing week 13 with week 2, and week 24 with week 13. A Bonferroni correction for 2 comparisons was applied (adjusted p-values).

DETAILED DESCRIPTION OF THE INVENTION

Figure 1:
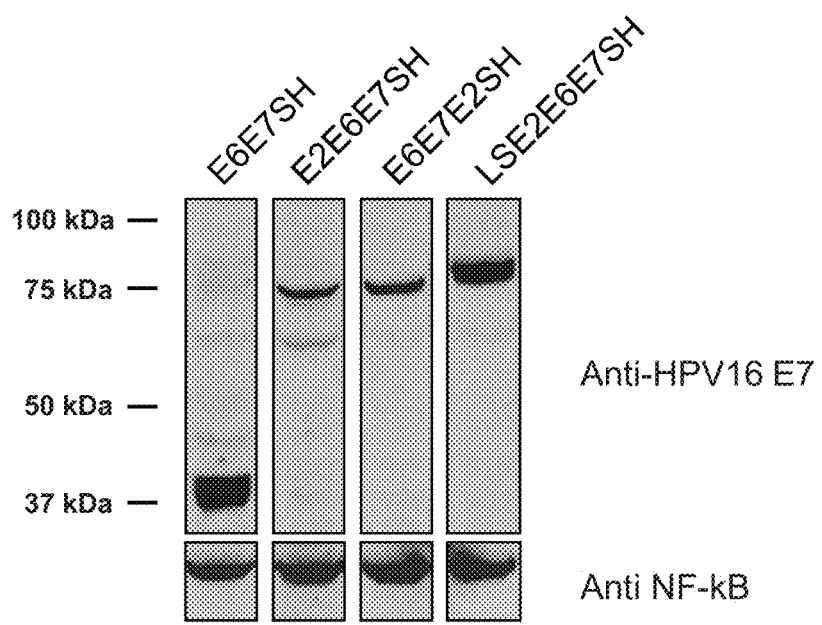
FIG. 1. Expression of fusion proteins of HPV16 E6 and E7. HEK-293T cells were transiently transfected with DNA vectors expressing the transgenes indicated above the figure. 24 hr after transfection the cells were harvested and cell extracts were analyzed by SDS-PAGE and western blotting with an antibody against HPV16 E7 (upper panel). A loading control showing NF-kB (lower panel) confirms similar loading of cell lysates in all lanes. A molecular weight marker is indicated on the left. Expected sizes of the fusion proteins: E6E7SH approx. 38 kDa; E2E6E7SH and E6E7E2SH approx. 75 kDa, LSE2E6E7SH approx. 78 kDa.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a", "an", and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

The invention provides one or more vectors, vaccines, and vaccine combinations that can be used for generating an immune response against HPV infections and diseases associated therewith.

The vectors, vaccines, and vaccine combinations of embodiments of the present invention comprise a nucleic acid molecule encoding one or more polypeptides that are carefully designed molecules containing virtually the complete E6 and E7 amino acid sequences, and in some embodiments E2 as well, of HPV16 in the form of fragments that are re-ordered and partly overlapping such that (essentially) all T-cell epitopes of the HPV16 E6 and E7 protein are present. The vectors, vaccines, and vaccine combinations of embodiments of the present invention additionally comprise a nucleic acid molecule encoding one or more polypeptides that are carefully designed molecules containing virtually the complete E6 and E7 amino acid sequences, and in some embodiments E2 as well, of HPV18 in the form of fragments that are re-ordered and partly overlapping such that (essentially) all T-cell epitopes of the HPV18 E6 and E7 protein are present. Earlier molecules with some potential as HPV vaccines have been described by others (e.g. Kenter et al., 2009, N Engl J Med 361: 1838-47; Daayana et al., 2010, Br J Cancer 102: 1129-36; Smahel et al., 2001, Virology 281: 231-38; Yan et al., 2009, Vaccine 27: 431-40; Öhlschläger et al., 2006, Vaccine 24: 2880-93; Oosterhuis et al., 2011, Int J Cancer 129: 397-406; EP1183368, WO 2013/083287), but each of these molecules has one or more drawbacks. The vectors, vaccines, and vaccine combinations of the present invention are advantageous in at least one and typically several aspects with respect to the approaches described earlier. In particular, advantages of the present invention include, but are not limited to: (i) they have a desired safety profile, as the nucleic acid molecules have a strongly reduced (as compared to native E6 and E7 proteins), down to non-detectable, transforming activity; (ii) they are single nucleic acid molecules, which are easy to manufacture at industrial scale in an economically feasible manner, and do not pose logistic challenges unlike multiple molecule approaches; (iii) the encoded polypeptides of the vaccines, and vaccine combinations comprise essentially all T-cell epitopes of the native HPV16 and HPV 18 E6 and E7 proteins; (iv) the design of the encoded polypeptides has minimized the introduction of undesired potential strong neo-epitopes (i.e. epitopes not present in the native E6 and E7 proteins); (v) in certain embodiments, they are not dependent on highly reactogenic adjuvants to raise a desired immune response; and (vi) in certain embodiments, as shown herein, the combined administration (e.g. in prime-boost schedule) of the adenoviral vaccine and the MVA vaccine provide an enhanced immune response, as compared to administrations of the vaccines alone.

Thus, the vectors, vaccines, and vaccine combinations of embodiments of the invention represent a major step forward by combining various advantageous characteristics in a single design, and are excellent candidates primarily for therapeutic vaccination against HPV16 and HPV18. These vectors, vaccines, and vaccine combinations could also be used as prophylactic vaccines against HPV16 and HPV18, meaning that they are likely to prevent persistent infection with HPV16, HPV18, or both HPV16 and HPV18 of vaccinated subjects.

In developing certain embodiments of the invention, we used the IEDB-AR to determine the possible formation of non-natural strong epitopes that could be introduced at the newly created junctions between the different E6 and E7 fragments. In certain embodiments for the HPV16 designer molecule, by careful design, the number of neo-epitopes with a length of nine amino acids with a predicted binding affinity <50 nM for the 20 most common HLA-A, 20 most common HLA-B and 20 most common HLA-C alleles in the re-ordered HPV16 E6 and E7 sequences was minimized to only 1. This is a significant improvement over constructs described by others, which for a single shuffled HPV16 E6 protein already contained more than 30 of such neo-epitopes, and which constructs will highly likely comprise even several more neo-epitopes in sequences that were appended to these constructs to prevent loss of epitopes (Öhlschläger et al., 2006, *Vaccine* 24: 2880-93). Hence the constructs of the invention have a significantly improved immunologic profile since chances of an altered immune response as compared to native E6 and E7 have been minimized in the molecules of the invention, as compared to approaches described by others.

Skilled persons can, using routine techniques, make nucleotide substitutions that do not affect the polypeptide sequence encoded by the polynucleotides described to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

In a preferred embodiment, nucleic acid molecules encoding the polypeptides, or HPV fusion proteins, according to the invention have been configured for optimal expression and efficacy in one or more vectors of the present invention. For example, a nucleic acid molecule encoding an HPV 16 polypeptide comprising the amino acid sequence of SEQ ID NO:1 in certain embodiments comprises the polynucleotide sequence of SEQ ID NO: 2, a nucleic acid molecule encoding an HPV16 polypeptide comprising the amino acid sequence of SEQ ID NO:3 in certain embodiments comprises the polynucleotide sequence of SEQ ID NO:4 or SEQ ID NO:24, and a nucleic acid molecule encoding an HPV16 polypeptide comprising the amino acid sequence of SEQ ID NO:5 in certain embodiments comprises the polynucleotide sequence of SEQ ID NO:6. Additionally, a nucleic acid molecules encoding an HPV 18 polypeptide comprising the amino acid sequence of SEQ ID NO:20 in certain embodiments comprises the polynucleotide sequence of SEQ ID NO: 21 and a nucleic acid molecule encoding an HPV18 polypeptide comprising the amino acid sequence of SEQ ID NO:22 in certain embodiments comprises the polynucleotide sequence of SEQ ID NO:23 or SEQ ID NO:25.

In certain embodiments, the nucleic acids according to the invention encompass homologous or variant sequences. These sequences are defined as having a percentage of sequence identity to the nucleic acids of the invention.

Preferably, such homologues or variants have at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% sequence identity to the referenced nucleic acid sequence. The term homologue or variant also encompasses truncated, deleted or otherwise modified nucleotide sequences.

Techniques for determining sequence identity between nucleic acids are known in the art. Two or more sequences can be compared by determining their "percent identity." The percent identity of two sequences is the number of exact matches between two aligned sequences divided by the length of the shorter sequences and multiplied by 100.

"Percent (%) sequence identity" with respect to nucleotide sequence or nucleic acids is defined as the percentage of nucleotide residues in a candidate sequence that are identical with the nucleotide residues in the reference sequence (i.e., the nucleic acid sequence from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

For example, an appropriate alignment for nucleic acid sequences is provided by the local homology algorithm of Smith and Waterman, (1981), Advances in Applied Mathematics 2:482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), Nucl. Acids Res. 14(6):6745-6763. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://http://blast.ncbi.nlm.nih.gov/.

Nucleic acid sequences can be cloned using routine molecular biology techniques, or generated de novo by DNA synthesis, which can be performed using routine procedures by service companies having business in the field of DNA synthesis and/or molecular cloning (e.g. GeneArt, GenScripts, Invitrogen, Eurofins).

It will be appreciated by a skilled person that changes can be made to a protein, e.g. by amino acid substitutions, deletions, additions, etc, e.g. using routine molecular biology procedures. Generally, conservative amino acid substitutions may be applied without loss of function or immunogenicity of a polypeptide. This can be checked according to routine procedures well known to the skilled person.

In certain embodiments, the encoded polypeptides according to at least one aspect of the invention further comprise a leader sequence, also referred to as signal sequence or signal peptide. This is a short (typically 5-30 amino acids long) peptide present at the N-terminus of the majority of newly synthesized proteins that are destined towards the secretory pathway. The presence of such a sequence may lead to increased expression and immunogenicity. Non-limiting examples that can be used are an IgE leader peptide (see e.g. U.S. Pat. No. 6,733,994; e.g. having sequence MDWTWILFLVAAATRVHS (SEQ ID NO: 7)) or a HAVT20 leader peptide (e.g. having sequence MACPGFLWALVISTCLEFSMA (SEQ ID NO: 9)). One of these can optionally be added to the N-terminus of a polypeptide of the invention. In other embodiments, a polypeptide according to the invention does not comprise a leader sequence.

Diverse types of HPV exist (over 120 types have been identified and are referred to by number), and generally for each type that needs to be covered by a vaccine, type-specific antigens may need to be incorporated in the vaccine, although for certain antigens some cross-reactivity might exist. Types 16, 18, 31, 33, 35, 39, 45, 51, 52, 56, 58, 59, 68, 73, and 82 are carcinogenic "high-risk" sexually transmitted HPVs and may lead to the development of cervical intraepithelial neoplasia (CIN), vulvar intraepithelial neoplasia (VIN), vaginal intraepithelial neoplasia (VaIN), penile intraepithelial neoplasia (PIN), and/or anal intraepithelial neoplasia (AIN). The HPV according to the invention (i.e. the HPV from which the E6 and E7 fragments in the encoded polypeptide are derived) is HPV16 (for SEQ ID NOs: 1-6), or HPV18 (for SEQ ID NOs: 20-23). It can be used for subjects that are infected with HPV16 or HPV18, respectively. It can in certain embodiments also suitably be combined with vaccines against other HPV types. In certain embodiments, this combination is with a vaccine against HPV of a high risk type as identified above, e.g. a vaccine against HPV16 with a vaccine against HPV18. In other embodiments, the vaccine of the invention is combined with a vaccine against one or more of HPV-16, -18, -31, -33, -35, -39, -45, -51, -52, -56, -58, -59, -68, -73, or -82. Such combinations could for instance be used if the exact type of HPV infection is not yet certain, or if an immune response with a prophylactic effect is desired against more than one HPV type. Also combinations of the vaccines of the invention with vaccines against HPV types that cause genital warts, such as HPV6 and/or HPV11, are envisaged. Sequences of these HPV types and the proteins encoded thereby (e.g. E6, E7, E2) are available to the skilled person in public databases, such as the GenBank sequence database provided by the National Center for of technology Information (NCBI).

A polypeptide according to one aspect of the invention for HPV16 comprises the amino acid sequence of SEQ ID NO: 1, and in one embodiment a nucleic acid molecule according to the invention comprises the polynucleotide sequence of SEQ ID NO: 2. A polypeptide according to the invention for HPV18 comprises the amino acid sequence of SEQ ID NO: 20, and in one embodiment a nucleic acid molecule according to the invention comprises the polynucleotide sequence of SEQ ID NO: 21.

Sequences herein are provided from 5' to 3' direction or from N- to C-terminus, as custom in the art.

The encoded polypeptides according to the invention comprise the epitopes of HPV16 E6 and E7 proteins, or alternatively the epitopes of HPV18 E6 and E7 proteins. In certain embodiments, the polypeptide according to the invention further comprises (and hence the nucleic acid encoding the polypeptide further encodes) at least one further antigen or epitope(s) of such further antigen. Such a further antigen preferably is an HPV antigen, preferably of the same HPV type as the E6 and E7 proteins in the polypeptide, i.e. HPV16 or HPV18 respectively. Such a further antigen can thus be an HPV protein or an immunogenic fragment thereof, and in certain embodiments comprises an E2 protein or a fragment thereof comprising at least one epitope of E2 of HPV, preferably from HPV16 or HPV18. Such further antigens or epitopes can be expressed independently of an E6 and E7 polypeptide according to the invention. Such further antigens or epitopes can also be expressed as a part of a fusion protein, for example, being placed internally between two fragments of an E6 and/or E7 in a polypeptide comprising the amino acid sequence of SEQ ID NO: 1 or SEQ ID NO: 20, but preferably being fused N-terminally or C-terminally to an E6/E7 in a polypeptide comprising the amino acid sequence of SEQ ID NO: 1 or SEQ ID NO: 20. Alternatively or in addition, amino acid sequences can be present that stimulate the immune response. Thus, in certain embodiments the invention provides nucleic acid molecules according to the invention, encoding a polypeptide comprising the amino acid sequence of SEQ ID NO: 1 or SEQ ID NO: 20, and wherein the polypeptide further comprises at least one other antigen, e.g. HPV E2 protein or at least one epitope, but preferably more epitopes, thereof. One advantage of the addition of E2 antigen for the instant invention is that E2 is known to be expressed early during infection/in low grade lesions where E6 and E7 expression is still very low.

During the development towards cervical cancer E2 expression is lost and as a result E6 and E7 levels are increased (Yugawa and Kiyono, 2009, *Rev Med Virol* 19: 97-113). Combining epitopes from E2, E6 and E7 in one vaccine allows for treatment in a broad target group of patients, ranging from having persistent infection to invasive cervical cancer (or other HPV16-caused cancers). In certain embodiments, the E2 protein is a wild-type E2 protein. In certain other embodiments, the E2 protein has a deletion or one or more mutations in its DNA binding domain (as compared to a wild type E2 protein). The sequence of the HPV16 and HPV18 E2 proteins can be found in the NCBI protein database (www.ncbi.nlm.nih.gov/protein) under numbers NP_041328.1 and AAP20597.1, respectively. Several single amino acid changes in HPV16 E2 such as G293V, K299M, or C300R in the C-terminal part of this protein are known to abrogate DNA binding. For HPV18 E2, the corresponding amino acid changes are G294V, K300M, C301R.

An advantage of using a variant or fragment of E2 that lacks DNA binding capacity is that it could prevent unpredictable transcriptional changes via direct binding to host cell DNA in the cells where it is expressed. In addition to or as an alternative to mutations in the DNA binding domain described above, further approaches to prevent E2 activity are to introduce mutations that abrogate activity of the more N-terminally located E2 transactivation domain, and/or that are reported to affect the structure of the E2 polypeptide. For HPV16 E2, non-limiting examples of amino acid changes at positions that have previously been described (e.g. Brokaw et al, 1996; Sakai et al, 1996) are R37A, I73A, W92A, E39A, W33A, P106A and G156A, and HPV16 E2 according to the invention could optionally comprise one or more of these mutations in the transactivation domain. In one preferred embodiment, the HPV16 E2 fragment comprises a nucleic acid encoding a polypeptide comprising the amino acid sequence of SEQ ID NO: 28. In a more particular embodiment, the nucleic acid sequence encoding for SEQ ID NO: 28 comprises the polynucleotide sequence of SEQ ID NO: 29 or SEQ ID NO: 30. For HPV18 E2, the corresponding amino acid changes are R41A, I77A, W96A, E43A, W37A, P110A and G161A, and HPV18 E2 according to the invention could thus optionally comprise one or more of these mutations in the transactivation domain. In one preferred embodiment, the HPV18 E2 fragment comprises a nucleic acid encoding a polypeptide comprising the amino acid sequence of SEQ ID NO: 31. In a more particular embodiment, the nucleic acid sequence encoding for SEQ ID NO: 31 comprises the polynucleotide sequence of SEQ ID NO: 32 or SEQ ID NO: 33.

In certain embodiments, E2 has mutations in the transactivation domain, in other embodiments E2 has mutations in the DNA binding domain, and in further embodiments E2 has mutations in both the transactivation domain and in the DNA binding domain. In yet another alternative embodiment, the E2 polypeptide according to the invention is divided in fragments which are reordered (shuffled), to abrogate E2 activity while maintaining the E2 epitopes for immunogenicity. Such embodiment could optionally be combined with one or more of the mutations described above, e.g. in the DNA binding domain and/or in the transactivation domain. Besides wild-type HPV E2 polypeptides, all such E2 mutants can be used as the E2 protein or part or variant thereof according to the invention.

The E2 protein or part or variant thereof, such as, but not limited to those described herein, can be added internally, but preferably is fused to the N-terminus or to the C-terminus of a polypeptide of the invention having the amino acid sequence of SEQ ID NO: 1 or SEQ ID NO: 20. In one embodiment for HPV16, a nucleic acid molecule of the invention encodes a polypeptide comprising the amino acid sequence of SEQ ID NO: 3. In one embodiment thereof, the nucleic acid molecule of the invention comprises the polynucleotide sequence of SEQ ID NO: 4 or SEQ ID NO:24. In another embodiment for HPV16, a nucleic acid molecule of the invention encodes a polypeptide comprising the amino acid sequence of SEQ ID NO: 5. In one embodiment thereof, a nucleic acid molecule of the invention comprises the polynucleotide sequence of SEQ ID NO: 6. In one embodiment for HPV18, a nucleic acid molecule of the invention encodes a polypeptide comprising the amino acid sequence of SEQ ID NO: 22. In one embodiment thereof, a nucleic acid molecule of the invention comprises the polynucleotide sequence of SEQ ID NO: 23 or SEQ ID NO: 25.

It is also possible to make further fusions of the designer polypeptides of the invention with further proteins, e.g. so called carrier proteins, such as Calreticulin, *Mycobacterium* Tubercelosis heat shock protein-70, IP10, or Tetanus toxin fragment C (see Oosterhuis et al., *Human Gene Ther*, 2012, supra, for more examples), which could further enhance the immune response to the HPV E6 and E7 (and optionally E2) epitopes. The invention thus also provides such further fusion proteins, and nucleic acids encoding such.

In certain embodiments, one or more of the nucleic acid molecules according to the invention are incorporated into a vector. A "vector" as used herein, is typically a vehicle to artificially carry foreign genetic material into another cell, where it can be replicated and/or expressed, and according to the invention can be any nucleic acid molecule that incorporates a nucleic acid molecule according to the invention. These can be prepared according to routine molecular biology techniques such as cloning. Typically such vectors can be propagated in at least one type of suitable hosts such as bacteria, yeast, insect cells, mammalian cells, and the like. Four major types of vectors are plasmids, viral vectors, cosmids, and artificial chromosomes. The vector itself is generally a DNA sequence that consists of an insert (transgene; in the present invention the nucleic acid encoding the fusion polypeptide of the invention) and a sequence that serves as the "backbone" of the vector. The purpose of a vector which transfers genetic information to another cell is typically to isolate, multiply, or express the insert in the target cell.

Preferably, the sequence encoding the polypeptide is operably linked to a promoter in the vector. The term "operably linked" is intended to mean that the nucleotide sequence of interest is linked to the promoter in a manner that allows for expression of the nucleotide sequence (e.g., in a host cell when the vector is introduced into the host cell). Expression regulatory sequences can be operably linked to a transgene. In certain embodiments, vectors are designed for the expression of the transgene in the target cell, and generally have a promoter sequence that drives expression of the transgene. In certain embodiments, one or more of routinely used vector elements such as transcription terminator sequences, polyadenylation tail sequences, Kozak sequences, UTRs, origin of replication, multiple cloning sites, genetic markers, antibiotic resistance, and further sequences may be present, and the skilled person can design a vector such that it has the desired properties, e.g. for replication in certain cells for propagation and multiplication of the vector, and for expression of the transgene of the vector in target cells into which the vector is introduced. Vectors comprising the nucleic acid encoding the polypeptide according to the invention, preferably designed for expression in mammalian cells, are suitable as vaccines according to the invention. In certain embodiments, a vector according to the invention is a plasmid, a cosmid, a yeast artificial chromosome, a bacterial artificial chromosome, a viral vector, or the like. The person skilled in the art is aware that various promoters can be used to obtain expression of a gene in host cells. Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (e.g. obtainable from pIRES, cat. no. 631605, BD Sciences), and the like. Suitable promoters can also be derived from eukaryotic cells, such as methallothionein (MT) promoters, elongation factor 1α (EF-1α) promoter, ubiquitin C or UB6 promoter, actin promoter, an immunoglobulin promoter, heat shock promoters, and the like (see e.g. WO 2006/048459). A non-limiting example of a suitable promoter for obtaining expression in eukaryotic cells is a CMV-promoter (U.S. Pat. No. 5,385,839), e.g. the CMV immediate early promoter, for instance comprising nt. −735 to +95 from the CMV immediate early gene enhancer/promoter, e.g. a CMV promoter as provided herein with a sequence as set forth in SEQ ID NO: 13. A polyadenylation signal, for example the bovine growth hormone polyA signal (U.S. Pat. No. 5,122,458), may be present behind the transgene(s). In another, non-limiting example, the promoter can be a PrMVA13.5long promoter (WO 2014/063832) or a PrHyb promoter (U.S. Pat. Nos. 8,394,385, 8,613,936), which comprise the polynucleotide sequence of SEQ ID NO: 26 and SEQ ID NO: 27, respectively, and which are particularly useful for driving expression of transgenes in MVA vectors.

Further regulatory sequences may also be added. The term "regulatory sequence" is used interchangeably with "regulatory element" herein and refers to a segment of nucleic acid, typically but not limited to DNA, that modulate the transcription of the nucleic acid sequence to which it is operatively linked, and thus acts as a transcriptional modulator. A regulatory sequence often comprises nucleic acid sequences that are transcription binding domains that are recognized by the nucleic acid-binding domains of transcriptional proteins and/or transcription factors, enhancers or repressors etc. For example, it is possible to operably couple a repressor sequence to the promoter, which repressor sequence can be bound by a repressor protein that can decrease or prevent the expression of the transgene in a production cell line that expresses this repressor protein. This may improve genetic stability and/or expression levels of the nucleic acid molecule upon passaging and/or when this is produced at high quantities in the production cell line. Such systems have been described in the art. For example, a regulatory sequence could include one or more tetracycline operon operator sequences (tetO), such that expression is inhibited in the presence of the tetracycline operon repressor protein (tetR). In the absence of tetracycline, the tetR protein is able to bind to the tetO sites and repress transcription of a gene operably linked to the tetO sites. In the presence of tetracycline, however, a conformational change in the tetR protein prevents it from binding to the operator sequences, allowing transcription of operably linked genes to occur. In certain embodiments, a nucleic acid molecule, e.g. when present in a recombinant adenovirus vector, of the present invention can optionally include tetO operatively linked to a promoter, such that expression of one or more transgenes is inhibited in recombinant adenoviruses that are produced in the producer cell line in which tetR protein is expressed. Subsequently, expression would not be inhibited if the recombinant adenovirus is introduced into a subject or into cells that do not express the tetR protein (e.g., international patent application WO 07/073513). In certain other embodiments, a nucleic acid molecule of the present invention, e.g. when present in a recombinant adenovirus, can optionally include a cumate gene-switch system, in which regulation of expression is mediated by the binding of the repressor (CymR) to the operator site (CuO), placed downstream of the promoter (e.g., Mullick et al. *BMC Biotechnol.* 2006 6:43). As used herein, the term "repressor," refers to entities (e.g., proteins or other molecules) having the capacity to inhibit, interfere, retard and/or repress the production of heterologous protein product of a recombinant expression vector. For example, by interfering with a binding site at an appropriate location along the expression vector, such as in an expression cassette. Examples of repressors include tetR, CymR, the lac repressor, the trp repressor, the gal repressor, the lambda repressor, and other appropriate repressors known in the art. Examples of the use of the tetO/tetR operator/repressor system and of the CuO/CymR operator/repressor system are provided herein. Repression of vector transgene expression during vector propagation can prevent transgene instability, and may increase yields of vectors having a transgene of the invention during production. Hence, in some embodiments, the vectors of the invention have a promoter that can be repressed by binding of a repressor protein, e.g. by having a promoter that is operably coupled to a repressor operator sequence (e.g. in non-limiting embodiments, a TetO-containing sequence, e.g. the one set forth in the polynucleotide sequence of SEQ ID NO: 11, or a CuO-containing sequence, e.g. the one set forth in the polynucleotide sequence of SEQ ID NO: 12), to which a repressor protein (e.g. the TetR protein, e.g. having the amino acid sequence as set forth in SEQ ID NO: 15, or the CymR protein, e.g. having the amino acid sequence as set forth in SEQ ID NO: 17) can bind.

In preferred embodiments, the vector is a recombinant viral vector, which can be replication competent or replication deficient or defective. In certain embodiments, a viral vector comprises a recombinant DNA genome. In certain embodiments, a vector according to the invention is, for instance, a recombinant adenovirus, a recombinant pox virus such as an orthopoxvirus (e.g., a vaccinia virus, Modified Vaccinia Ankara (MVA)).

In one or more preferred embodiments, the vector according to the invention is recombinant poxvirus such as, but not limited to an orthopoxvirus. The recombinant orthopoxvirus can be a vaccinia virus (VV), a Wyeth strain, ACAM 1000, ACAM 2000, MVA, or MVA-BN.

In a more preferred embodiment, the recombinant poxvirus is MVA. In certain preferred embodiments, the MVA is MVA-BN. MVA-BN is replication incompetent, which is a significant advantage over other types of MVA. MVA-BN was deposited on Aug. 30, 2000, at the European Collection of Cell Cultures (ECACC) under number V00083008, and is described in International PCT publication WO2002042480 (see also e.g. EP Patent No. 1335987, U.S. Pat. Nos. 6,761,893, 6,913,752, 7,335,364, 7,459,270, 7,939,086, and 8,268,325). As described in those patent publications, MVA-BN does not reproductively replicate in cell lines 293, 143B, HeLa and HaCat.

In certain embodiments, a recombinant MVA is a derivative of MVA-BN. Such "derivatives" include viruses exhibiting essentially the same replication characteristics as the deposited strain (ECACC No. V00083008), but exhibiting differences in one or more parts of its genome. MVA-BN derivatives, as used herein, are characterized: i) in being capable of reproductive replication in chicken embryo fibroblasts (CEF) cells and the Baby Hamster Kidney cell line BHK but not capable of reproductive replication in the human cell lines HaCat, HeLa, and 143B; and ii) by a failure to replicate in a mouse strain that is incapable of producing mature B and T cells and as such is severely immune compromised and highly susceptible to a replicating virus. These characteristics and tests therefor have been well defined in the art (e.g. WO2002042480, U.S. Pat. Nos. 6,761,893 and 6,913,752).

In certain embodiments, the nucleic acid molecules described herein are incorporated in a variety of insertion sites, or intergenic regions in the MVA genome, or in the MVA-BN genome. The nucleic acid molecules can be inserted into the recombinant MVA, or MVA-BN as separate transcriptional units or as fusion genes, as described herein. In certain embodiments, the nucleic acid molecules are inserted into one or more intergenic regions (IGR) of the MVA, or MVA-BN. The IGR may be selected from IGR07/08, IGR 44/45, IGR 64/65, IGR 88/89, IGR 136/137, and IGR 148/149, preferably from IGR64/65, IGR88/89, and/or IGR 148/149. These IGRs are further characterized in WO 03/097845 (see also, e.g., EP Patent No. 1407033 and U.S. Pat. Nos. 7,550,147, 7,964,374, 8,034,354, and 8,741,308). The nucleic acid molecules may, additionally or alternatively, be inserted into one or more of the naturally occurring deletion sites I, II, II, IV, V, or VI of the MVA, or MVA-BN. In certain embodiments, less than 5, 4, 3, or 2 of the integration sites comprise the nucleic acid molecules of the present disclosure.

The number of insertion sites of MVA, or MVA-BN comprising the nucleic acid molecules can be 1, 2, 3, 4, 5, 6, 7, or more. The recombinant MVA, or MVA-BN can comprise the nucleic acid molecules inserted into 4, 3, 2, or 1 insertion sites.

In certain preferred embodiments, the nucleic acid molecules of the present disclosure are inserted into a single insertion site. In a preferred embodiment, nucleic acid molecules inserted in the single insertion site is a nucleic acid molecule encoding a polypeptide comprising an amino acid sequence selected from the group consisting of: SEQ ID NO: 1, SEQ ID NO: 3, SEQ ID NO: 5, SEQ ID NO: 20, SEQ ID NO: 22, and combinations thereof. In other preferred embodiments, nucleic acid molecules inserted in the single insertion site encode the amino acid sequences of SEQ ID NO: 3 and SEQ ID NO: 22. In still other preferred embodiments, a nucleic acid molecule inserted in the single insertion site is one or more nucleic acid molecules having at least 90% sequence identity to a polynucleotide sequence selected from the group consisting of SEQ ID NO: 2, SEQ ID NO: 4, SEQ ID NO: 6, SEQ ID NO: 21, SEQ ID NO: 23, SEQ ID NO: 24, and SEQ ID NO: 25, preferably comprising a polynucleotide sequence selected from the group consisting of SEQ ID NO: 2, SEQ ID NO: 4, SEQ ID NO: 6, SEQ ID NO: 21, SEQ ID NO: 23, SEQ ID NO: 24, and SEQ ID NO: 25. In still more preferred embodiments, two or more nucleic acid molecules are inserted in the single insertion site, the nucleic acid molecules have at least 90% sequence identity to the polynucleotide sequences of SEQ ID NO: 24 and ID NO: 25, respectively, preferably, comprise the polynucleotide sequences of SEQ ID NO: 24 and ID NO: 25, respectively. In another preferred embodiment the single insertion site is IGR88/89.

The recombinant MVA viruses provided herein can be generated by routine methods known in the art in view of the present disclosure. Methods to obtain recombinant poxviruses or to insert heterologous nucleotide sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) [J. Sambrook et al., Cold Spring Harbor Laboratory Press (1989)], and techniques for the handling and manipulation of viruses are described in Virology Methods Manual [B. W. J. Mahy et al. (eds.), Academic Press (1996)]. Similarly, techniques and know-how for the handling, manipulation and genetic engineering of MVA are described in Molecular Virology: A Practical Approach [A. J. Davison & R. M. Elliott (Eds.), The Practical Approach Series, IRL Press at Oxford University Press, Oxford, UK (1993)(see, e.g., Chapter 9: Expression of genes by Vaccinia virus vectors)] and Current Protocols in Molecular Biology [John Wiley & Son, Inc. (1998)(see, e.g., Chapter 16, Section IV: Expression of proteins in mammalian cells using vaccinia viral vector)].

For the generation of the various recombinant MVAs disclosed herein, different methods can be applicable. The nucleotide sequences to be inserted into the virus can be placed into an E. coli plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within E. coli bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture such as, e.g., CEF cells, can be infected with a poxvirus. The infected cell can be, subsequently, transfected with a first plasmid vector comprising a foreign gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter. Suitable marker or selection genes are, e.g., the genes encoding the green or red fluorescent protein, beta-galactosidase, neomycin-phosphoribosyltransferase, ecogpt, or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign gene or genes. In case, this gene can be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, coinfect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in E. coli or another bacterial species between a vaccinia virus genome cloned as a bacterial artificial chromosome (BAC) and a linear foreign sequence flanked with DNA sequences homologous to sequences flanking the desired site of integration in the vaccinia virus genome.

In other preferred embodiments, a vector according to the invention is a recombinant adenovirus. Advantages of adenoviruses for use as vaccines include ease of manipulation, good manufacturability at large scale, and an excellent safety record based on many years of experience in research, development, manufacturing and clinical trials with numerous adenoviral vectors that have been reported. Adenoviral vectors that are used as vaccines generally provide a good immune response to the transgene-encoded protein, including a cellular immune response. An adenoviral vector according to the invention can be based on any type of adenovirus, and in certain embodiments is a human adenovirus, which can be of any serotype. In other embodiments, it is a simian adenovirus, such as chimpanzee or gorilla adenovirus, which can be of any serotype. In certain embodiments, a vector according to the invention is of a human adenovirus serotype 26 or 35. The preparation of recombinant adenoviral vectors is well known in the art. In certain embodiments, an adenoviral vector according to the invention is deficient in at least one essential gene function of the E1 region, e.g. the E1a region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region.

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in Virology, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual*, 2d ed., Cold Spring Harbor Press, Cold Spring Harbor, N.Y. (1989), Watson et al., *Recombinant DNA*, 2d ed., Scientific American Books (1992), and Ausubel et al., *Current Protocols in Molecular Biology*, Wiley Interscience Publishers, NY (1995), and other references mentioned herein.

Figure 6:
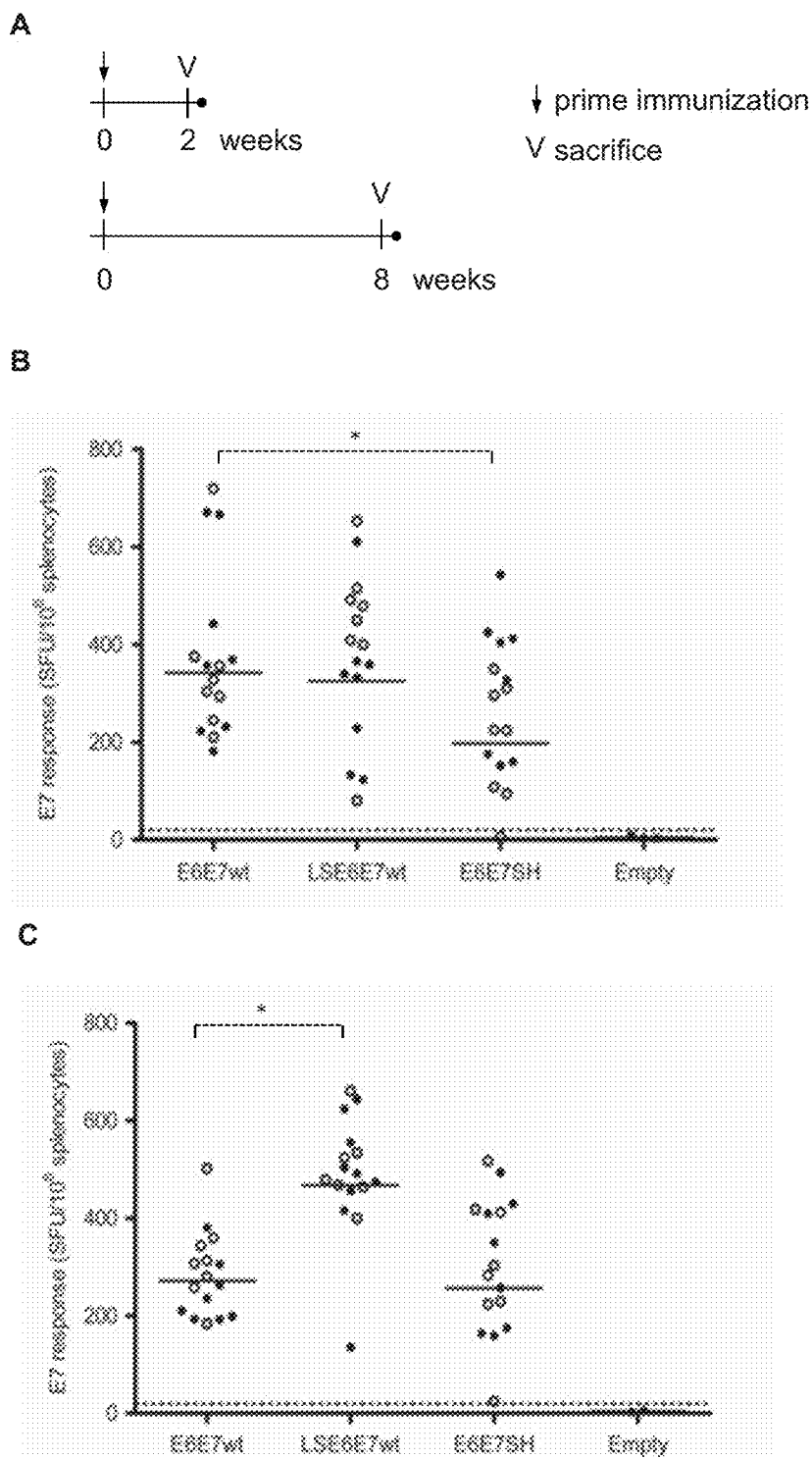
FIG. 6. Immunogenicity of HPV16 E6E7SH—IFNγ ELISPOT analysis. (A). Immunization scheme. Mice were immunized with adenovectors with inserts as indicated. E7-specific responses at two weeks (B) and at eight weeks (C) were analyzed by IFNγ ELISPOT (represented as spot-forming units (SFU) per $10^6$ splenocytes). The closed circles represent mice immunized with a dosage of $1*10^{10}$ vp, and open circles represent mice immunized with $5*10^9$ vp. The black bar represents the geometric mean of the responses. The dotted line indicates the lower detection limit in the ELISPOT assay. ANOVA Post-hoc Bonferroni statistical analysis was performed on log transformed data. *: $p<0.05$. For details see example 3.

Particularly preferred serotypes for the recombinant adenovirus are human serotype 35 or human serotype 26, most preferably human serotype 26 (rAd26). Preparation of rAd26 vectors is described, for example, in WO 2007/104792 and in Abbink et al., 2007 *Virology* 81: 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., 2003, *J Virol* 77: 8263-71. Exemplary genome sequences of Ad35 are found in GenBank Accession AC_000019 and in FIG. 6 of WO 00/70071.

In certain embodiments, the adenovirus is replication deficient, e.g. because it contains a deletion in the E1 region of the genome. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as 'packaging cell' or 'complementing cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al., 2000, *Hum Gene Ther* 11: 213-19), 293, and the like. In certain embodiments, the producer cells are for instance HEK293 cells, or PER.C6 cells, or 911 cells, or IT293 SF cells, and the like. Production of adenoviral vectors in producer cells is reviewed in (Kovesdi et al., 2010, *Viruses* 2: 1681-703).

In certain embodiments, an E1-deficient adenovirus comprises the E4-orf6 coding sequence of an adenovirus of subgroup C such as Ad5. This allows propagation of such adenoviruses in well known complementing cell lines that express the E1 genes of Ad5, such as for example 293 cells or PER.C6 cells (see, e.g. Havenga et al., 2006, *J Gen Virol* 87: 2135-43; WO 03/104467, incorporated in its entirety by reference herein).

"Heterologous nucleic acid" (also referred to herein as 'transgene') in vectors of the invention is nucleic acid that is not naturally present in the vector, and according to the present invention the nucleic acid encoding the fusion polypeptide of the invention is considered heterologous nucleic acid when present in a vector. It is introduced into the vector for instance by standard molecular biology techniques. It can for instance be cloned into a deleted E1 or E3 region of an adenoviral vector, or in the region between the E4 region and the rITR. A transgene is generally operably linked to expression control sequences. In preferred embodiments, the transgene is cloned into the E1-region of an adenoviral vector.

Production of vectors such as MVA vectors, or recombinant adenovirus vectors, can be performed according to various methods well known to the person skilled in the art in view of the present disclosure. Generally, the production entails propagation in cultured cells to generate a substantial amount of vector material, followed by harvest of the vector from the cell culture, and typically followed by further purification of the vector to remove other substances and obtain purified vectors that can be formulated into pharmaceutical compositions (e.g., Hoganson et al., 2002, *BioProcessing J* 1: 43-8; Evans et al., 2004, *J Pharm Sci* 93:2458-75). For example, methods for harvesting adenovirus from cultures of producer cells have for instance been extensively described in WO 2005/080556. For example WO 2010/060719, and WO 2011/098592, both incorporated by reference herein, describe suitable methods for obtaining and purifying large amounts of recombinant adenoviruses.

In additional aspects, the invention further provides vaccines, and vaccine combinations comprising nucleic acid molecules, vectors, or recombinant viruses according to the invention, wherein embodiments for each of these aspects can include those as described herein. In certain embodiments, a vaccine according to the invention comprises a nucleic acid molecule described herein. In preferred embodiments, the vaccine comprises a vector according to the invention, preferably a recombinant poxvirus vector such as an MVA vector, preferably MVA-BN vector or derivatives thereof, and/or a recombinant adenovirus vector, such as a rAd26 vector.

In certain embodiments, a vaccine according to the invention that encodes the HPV16 designer polypeptide comprises further active ingredients, e.g. nucleic acid encoding at least one epitope of E6 and/or E7 protein of at least one HPV type different from HPV16, e.g. a high risk HPV type such as HPV18, -31, -33, -35, -39, -45, -51, -52, -56, -58, -59, -68, -73, or -82. In certain embodiments, a vaccine according to the invention that encodes the HPV18 designer polypeptide comprises further active ingredients, e.g. nucleic acid encoding at least one epitope of E6 and/or E7 protein of at least one HPV type different from HPV18, e.g. a high risk HPV type such as HPV16, -31, -33, -35, -39, -45, -51, -52, -56, -58, -59, -68, -73, or -82.

Particularly preferred are vectors, vaccines, or vaccine combinations comprising nucleic acids encoding both HPV16 and HPV18 designer polypeptides of the invention, e.g., encoding a polypeptide comprising the amino acid sequence of SEQ ID NO: 1 as well as a polypeptide comprising the amino acid sequence of SEQ ID NO: 20; e.g., encoding a polypeptide comprising the amino acid sequence of SEQ ID NO: 3 as well as a polypeptide comprising the amino acid sequence of SEQ ID NO: 22. In such vectors, vaccines, vaccine compositions, or vaccine combinations, the HPV16 and HPV18 components can be in the same composition as separate molecules, or they can be in the same molecule e.g. encoded on the same vector. One advantage of such combinations is that such vaccines can work therapeutically in subjects that are infected with either HPV16 or with HPV18 (the two most prevailing high risk HPV types that together account for the majority of HPV-induced cancers), so that such vaccines have increased applicability over the monotype vaccines that have either HPV16 or HPV18 designer molecules.

In other embodiments, the HPV16 and HPV18 components could be provided as a kit or composition of parts with a separate HPV16 component and a separate HPV18 component for combined use in vaccination, e.g. for reconstitution prior to administration, or for separate but essentially simultaneous administration. One advantage of such combinations is that such vaccines can work therapeutically in subjects that are infected with either HPV16 or with HPV18. The term "vaccine" refers to an agent or composition containing an active component effective to induce a prophylactic and/or therapeutic degree of immunity in a subject against a certain pathogen or disease, in this case therapeutically against HPV. The vaccine typically comprises the nucleic acid molecule, or vector, or recombinant virus according to the invention, and a pharmaceutically acceptable excipient. Upon administration to a subject, the polypeptide encoded by the nucleic acid molecule according to the invention will be expressed in the subject, which will lead to an immune response towards antigenic fragments that are present in the encoded polypeptide. The advantage of a vaccine of the present invention is that essentially all T-cell epitopes of E6 and E7 of HPV16 (e.g., SEQ ID NOs: 1-6, and 24) or HPV18 (e.g., SEQ ID NOs: 20-23, and 25), and optionally epitopes of E2 of HPV16 or HPV18 are present and thus a T-cell response to any epitope present in wild-type E6, or E7, or optionally E2, can be mounted in the vaccinee. Further, the vaccine has all the safety and efficacy advantages as outlined above for the nucleic acid molecules according to the invention.

For administering to humans, the invention may employ pharmaceutical compositions comprising the vector and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). An excipient is generally a pharmacologically inactive substance formulated with the active ingredient of a medication. Excipients are commonly used to bulk up formulations that contain potent active ingredients (thus often referred to as "bulking agents," "fillers," or "diluents"), to allow convenient and accurate dispensation of a drug substance when producing a dosage form. They also can serve various therapeutic-enhancing purposes, such as facilitating drug absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients also depends upon the route of administration and the dosage form, as well as the active ingredient and other factors.

The purified nucleic acid molecule, vector or polypeptide preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g., pH 5.0 to 7.5. The nucleic acid molecule or vector or polypeptide typically is in a solution having a suitable buffer, and the solution of vector may also contain a salt. Optionally stabilizing agent may be present, such as albumin. In certain embodiments, detergent is added. In certain embodiments, vaccine may be formulated into an injectable preparation. These formulations contain effective amounts of nucleic acid molecule, vector or polypeptide are either sterile liquid solutions, liquid suspensions or lyophilized versions and optionally contain stabilizers or excipients.

For instance recombinant adenovirus vector may be stored in the buffer that is also used for the Adenovirus World Standard (Hoganson et al., 2002, *Bioprocessing J* 1: 43-8): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Another formulation buffer that is suitable for recombinant adenovirus comprises 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. An exemplary formulation buffer suitable for MVA vectors can be 10 mM Tris, 140 mM NaCl, pH 7.7 (or 7.4). Obviously, many other buffers can be used, and several examples of suitable formulations for the storage and for pharmaceutical administration of purified vectors are known.

In certain embodiments a composition comprising the vector further comprises one or more adjuvants. Adjuvants are known in the art to further increase the immune response to an applied antigenic determinant. The terms "adjuvant" and "immune stimulant" are used interchangeably herein, and are defined as one or more substances that cause stimulation of the immune system. In this context, an adjuvant is used to enhance an immune response to the polypeptides encoded by the nucleic acid molecules in the vectors of the invention. Examples of suitable adjuvants include aluminium salts such as aluminium hydroxide and/or aluminium phosphate and/or aluminium potassium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, and the like. It is also possible to use vector-encoded adjuvant, e.g. by using heterologous nucleic acid that encodes a fusion of the oligomerization domain of C4-binding protein (C4 bp) to the antigen of interest (e.g. Solabomi et al., 2008, *Infect Immun* 76: 3817-23), or by using a vector encoding both the transgene of interest and a TLR-3 agonist such as heterologous dsRNA (e.g. WO 2007/100908), or the like.

In other embodiments, the compositions of the invention do not comprise adjuvants.

Pharmaceutical compositions can be administered to a subject, e.g. a human subject. The total dose of the vaccine active component provided to a subject during one administration can be varied as is known to the skilled practitioner, and for adenovirus is generally from $1\times10^7$ viral particles (vp) to $1\times10^{12}$ vp, preferably from $1\times10^8$ vp to $1\times10^{11}$ vp, for instance from $3\times10^8$ to $5\times10^{10}$ vp, for instance from $10^9$ to $3\times10^{10}$ vp; for MVA virus a total dose of the vaccine is generally from $1\times10^5$ $TCID_{50}$ (tissue culture infection dose) to $1\times10^{10}$ $TCID_{50}$, preferably from $1\times10^7$ $TCID_{50}$ to $1\times10^{10}$, and more preferably from $1\times10^8$ $TCID_{50}$ to $1\times10^9$ $TCID_{50}$. Administration of pharmaceutical compositions can be performed using standard routes of administration. Non-limiting embodiments include parenteral administration, such as by injection, e.g. intradermal, intramuscular, etc, or subcutaneous or transcutaneous, or mucosal administration, e.g. intranasal, oral, intravaginal, rectal, and the like. In one embodiment a composition is administered by intramuscular injection, e.g. into the deltoid muscle of the arm, or vastus lateralis muscle of the thigh. In certain embodiments the vaccine is a DNA vaccine, and this can for instance be administered intradermally, e.g. by DNA tattooing (see, e.g. Oosterhuis et al., 2012, *Curr Top Microbiol Immunol* 351: 221-50). This route is also feasible for adenoviral vectors and poxviral vectors. In certain embodiments a composition according to the invention comprises an adenoviral vector or a poxviral vector, or both an adenoviral vector and a poxviral vector and is administered by intramuscular injection. The skilled person knows the various possibilities to administer a composition, such as a vaccine in order to induce an immune response to the antigen(s) in the vaccine.

A subject as used herein preferably is a mammal, for instance a rodent, e.g. a mouse, or a non-human-primate, or a human. Preferably, the subject is a human subject.

The vaccines of the invention can be used to treat patients having one of various stages of diseases caused by HPV (in particular type 16 for vaccines comprising or encoding any of SEQ ID NOs: 1-6, 24, and 28 or type 18 for vaccines comprising or encoding any of SEQ ID NOs: 20-23, 25, and 31 or both types for vaccines that comprise or encode both HPV16 and HPV18 designer molecules described herein), from incident and persistent HPV infection as such (e.g. as detected by HPV DNA testing), thus before (pre-)cancerous lesions are formed, as well as cervical intraepithelial neoplasia (CIN; also known as cervical dysplasia and cervical interstitial neoplasia, which is the potentially premalignant transformation and abnormal growth (dysplasia) of squamous cells on the surface of the cervix) up to and including cervical cancer (such as cervical squamous cell carcinoma (SCC)). In addition, other HPV-induced neoplasias, such as vulvar intraepithelial neoplasia (VIN), vaginal intraepithelial neoplasia (VaIN), penile intraepithelial neoplasia (PIN), anal intraepithelial neoplasia (AIN) can be targeted as well as more advanced stages of oropharyngeal cancer (also known as head- and neck cancer), penile cancer, vaginal cancer, vulvar cancer and anal cancer. The vaccines of the invention thus can target a wide range of HPV induced lesions, and are likely most effective at the precancerous stages of HPV-induced disease, e.g. at the (persistent) infection and/or the neoplasia stages, where expression of E2, E6 and/or E7 is highest. It is also possible to combine the treatment using a vaccine of the invention with compounds that counteract or can overcome immune escape mechanisms in advanced cancer cells e.g. anti-PD1/PD-L1 antibodies, anti CTLA-4 antibodies such as Ipilimumab, anti-LAG-3 antibodies, anti-CD25 antibodies, IDO-inhibitors, CD40 agonistic antibodies, CD137 agonistic antibodies, etc (see, e.g. Hamid and Carvajal, 2013, *Expert Opinion Biol Ther* 13: 847-861; Mellman et al., 2011, Nature Rev 480: 480-89).

As used herein, 'treating' means administration of the vaccine to induce a therapeutic immune response against cells that express (epitopes of) HPV16 or 18 E6, and/or E7, and/or optionally E2, in the patient, which leads to at least reduction of the level of and preferably complete removal of HPV16 or 18 infection, which results in at least slowing and preferably stopping the progress of HPV16- or HPV18-caused disease such as neoplasias and/or symptoms thereof. Preferably treatment with the vaccine results also in remission of more advanced stages of HPV-induced cancers. It is preferred to administer the vaccine to patients that have an established HPV infection that has been typed, so that the vaccine that encodes the polypeptide of the corresponding HPV type can be administered. In the absence of screening the vaccine can also be administered in the part of the population that is likely to be HPV infected, i.e. sexually active people. It is also possible to administer a vaccine of the invention to subjects that have not been infected by HPV16 or 18, e.g. for prophylactic use, possibly in combination with a vaccine against another HPV type by which the patient has been infected, or alternatively in non-infected subjects. A vaccine of the invention can also be administered to a subject that is subject to further treatment by other means, e.g. surgery (removal of a lesion caused by HPV16 or 18 infection), or treatment with imiquimod (comprising a TLR-7/8 agonist, see e.g. Dayaana et al., 2010, *Br J Cancer* 102: 1129-36). The effect of the treatment can be measured either by cytology or by HPV testing.

In certain embodiments, the vaccination and methods described herein comprise administering the vaccine of the invention to a subject or patient at least once. It is also possible to provide one or more booster administrations of one or more further vaccines. If a boosting vaccination is performed, typically, such a boosting vaccination will be administered to the same subject at a moment between one week and one year, preferably between two weeks and four months, after administering an immunogenic composition with the same antigen to the subject for the first time (which is in such cases referred to as 'priming vaccination'). In alternative boosting regimens, it is also possible to administer different vectors, e.g. one or more adenoviruses of different serotype, or other vectors such as MVA, or DNA, or protein, to the subject as a priming or boosting vaccination. In certain embodiments, the same form of a vaccine of the invention is administered at least twice to the same patient in a prime-boost regimen, e.g. with the same recombinant adenovirus (such as Ad26) according to the invention.

In certain preferred embodiments, a vaccine of the invention is administered at least twice in a prime-boost regimen, but the vector of the vaccine is different, e.g. two different viral vectors are used, e.g. priming with recombinant Ad26 and boosting with a recombinant poxvirus, or vice versa. Non-limiting exemplary embodiments include: a) priming with a recombinant Ad26 vector and boosting with a recombinant MVA vector; b) priming with a recombinant Ad26 vector and a recombinant Ad35 vector and boosting with a recombinant MVA vector; c) priming with a recombinant poxviral vector (e.g., MVA) and boosting with a recombinant Ad26 vector; d) priming with a recombinant poxviral vector (e.g., MVA) and boosting with a recombinant Ad26 vector and a recombinant Ad35 vector; wherein in each case the priming and boosting vector each comprise at least one nucleic acid encoding a designer polypeptide of the invention. In certain preferred embodiments the priming and boosting vector each encode the same designer polypeptide of the invention. Each of the priming and/or boosting administrations can optionally be administered more than once to the same subject.

In certain embodiments, a vaccine, or recombinant virus according to the invention is administered at least three times in a prime-boost-boost regimen, for example, first in a priming administration, and second and third in two subsequent boosting administrations. In additional embodiments, further booster administrations might be added to the regimen. It is also possible to simultaneously or substantially simultaneously (e.g. not more than 10 minutes apart) administer an adenoviral vector and an MVA vector (which can either be in the same composition or in different compositions), to induce an immune response (see e.g. WO 2010/073043).

It is also an aspect of the invention to induce a CTL response against HPV16 or HPV18 in a subject, comprising administering a vector, vaccine, or vaccine combination according to the invention to the subject. The skilled person will understand that the vaccines that include HPV16 sequences (e.g., encoding or comprising any of SEQ ID NOs: 1-6, 24, and 28) work best against and are intended for use against HPV16 infection, while the vaccines that include HPV18 sequences (e.g., encoding or comprising any of SEQ ID NOs: 20-23, 25, and 31) work best against and are intended for use against HPV18 infection.

1. The invention provides also the following non-limiting embodiments:

1) A vaccine combination comprising:
   a) a first vaccine comprising an immunologically effective amount of one or more recombinant adenovirus vectors together comprising a first nucleic acid encoding a first polypeptide comprising the amino acid sequence of SEQ ID NO: 1 and a second nucleic acid encoding a second polypeptide comprising the amino acid sequence of SEQ ID NO: 20, together with a pharmaceutically acceptable carrier; and
   b) a second vaccine comprising an immunologically effective amount of a recombinant Modified Vaccinia Ankara (MVA) vector comprising a third nucleic acid encoding a third polypeptide comprising the amino acid sequence of SEQ ID NO: 1 and a fourth nucleic acid encoding a fourth polypeptide comprising the amino acid sequence of SEQ ID NO: 20, together with a pharmaceutically acceptable carrier;
2. wherein the MVA vector comprises MVA-BN or derivatives thereof.

2) The vaccine combination according to embodiment 1, wherein the first vaccine and the second vaccine each further comprise a nucleic acid encoding a fifth polypeptide comprising the amino acid sequence of SEQ ID NO: 28 and a nucleic acid encoding a sixth polypeptide comprising the amino acid sequence of SEQ ID NO: 31.

3) The vaccine combination according to any one of embodiments 1-2, wherein the first and third polypeptides each further comprise SEQ ID NO:28 and wherein the second and fourth polypeptides each further comprise SEQ ID NO: 31.

4) A vaccine combination according to embodiment 1, wherein the first nucleic acid and the third nucleic acid each encode a polypeptide comprising the amino acid sequence of SEQ ID NO: 3 or SEQ ID NO:5, and wherein the second nucleic acid and the fourth nucleic acid each encode a polypeptide comprising the amino acid sequence of SEQ ID NO: 22.

5) The vaccine combination according to any one of embodiments 1-4, wherein the nucleic acid encoding a polypeptide comprising SEQ ID NO: 1 has at least 90% sequence identity to the polynucleotide sequence of SEQ ID NO: 2 and the nucleic acid encoding a polypeptide comprising SEQ ID NO: 20 has at least 90% sequence identity to the polynucleotide sequence of SEQ ID NO: 21.

6) The vaccine combination according to any one of embodiments 1-5, wherein the nucleic acid encoding a polypeptide comprising SEQ ID NO: 1 has at least 95% sequence identity to SEQ ID NO: 2 and the nucleic acid encoding a polypeptide comprising SEQ ID NO: 20 has at least 95% sequence identity to SEQ ID NO: 21.

7) The vaccine combination according to any one of embodiments 1-6, wherein the nucleic acid encoding a polypeptide comprising SEQ ID NO: 1 comprises SEQ ID NO: 2 and the nucleic acid encoding a polypeptide comprising SEQ ID NO: 20 comprises SEQ ID NO: 21.

8) The vaccine combination according to embodiment 4, wherein the nucleic acid encoding a polypeptide comprising SEQ ID NO: 3 has at least 90% sequence identity to the polynucleotide sequence of SEQ ID NO: 4 or SEQ ID NO: 24, and the nucleic acid encoding a polypeptide comprising SEQ ID NO: 22 has at least 90% sequence identity to the polynucleotide sequence of SEQ ID NO: 23 or SEQ ID NO: 25.

9) The vaccine combination according to any one of embodiments 4 and 8, wherein the nucleic acid encoding a polypeptide comprising SEQ ID NO: 3 has at least 95% sequence identity to SEQ ID NO: 4 or SEQ ID NO: 24, and the nucleic acid encoding a polypeptide comprising SEQ ID NO: 22 has at least 95% sequence identity to SEQ ID NO: 23 or SEQ ID NO: 25.

10) The vaccine combination according to any one of embodiments 4 and 8-9, wherein the nucleic acid encoding a polypeptide comprising SEQ ID NO: 3 comprises SEQ ID NO: 4 or SEQ ID NO: 24 and the nucleic acid encoding a polypeptide comprising SEQ ID NO: 22 comprises SEQ ID NO: 23 or SEQ ID NO: 25.

11) The vaccine combination according to any one of embodiments 4 and 8-10, wherein the nucleic acid encoding a polypeptide comprising SEQ ID NO: 3 has at least 90% sequence identity to SEQ ID NO: 4 and the nucleic acid encoding a polypeptide comprising SEQ ID NO: 22 has at least 90% sequence identity to SEQ ID NO: 23.

12) The vaccine combination according to any one of embodiments 4 and 8-11, wherein the nucleic acid encoding a polypeptide comprising SEQ ID NO: 3 has at least 95% sequence identity to SEQ ID NO: 4 and the nucleic acid encoding a polypeptide comprising SEQ ID NO: 22 has at least 95% sequence identity to SEQ ID NO: 23.

13) The vaccine combination according to any one of embodiments 4 and 8-12, wherein the nucleic acid encoding a polypeptide comprising SEQ ID NO: 3 comprises SEQ ID NO: 4 and the nucleic acid encoding a polypeptide comprising SEQ ID NO: 22 comprises SEQ ID NO: 23.

14) The vaccine combination according to any one of embodiments 4 and 8-10, wherein the nucleic acid encoding a polypeptide comprising SEQ ID NO: 3 has at least 90% sequence identity to SEQ ID NO: 24 and the nucleic acid encoding a polypeptide comprising SEQ ID NO: 22 has at least 90% sequence identity to SEQ ID NO: 25.

15) The vaccine combination according to any one of embodiments 4, 8-10 and 14, wherein the nucleic acid encoding a polypeptide comprising SEQ ID NO: 3 has at least 95% sequence identity to SEQ ID NO: 24 and the nucleic acid encoding a polypeptide comprising SEQ ID NO: 22 has at least 95% sequence identity to SEQ ID NO: 25.

16) The vaccine combination according to any one of embodiments 4, 8-10 and 14-15, wherein the nucleic acid encoding a polypeptide comprising SEQ ID NO: 3 comprises SEQ ID NO: 24 and the nucleic acid encoding a polypeptide comprising SEQ ID NO: 22 comprises SEQ ID NO: 25.

17) The vaccine combination according to any one of embodiments 2-3, wherein the nucleic acid encoding a polypeptide comprising SEQ ID NO: 28 has at least 90% sequence identity to the polynucleotide sequence of SEQ ID NO: 29 or SEQ ID NO: 30, and wherein the nucleic acid encoding SEQ ID NO: 31 has at least 90% sequence identity to the polynucleotide sequence of SEQ ID NO: 32 or SEQ ID NO: 33.

18) The vaccine combination according to any one of embodiments 2-3 and 17, wherein the nucleic acid encoding a polypeptide comprising SEQ ID NO: 28 has at least 95% sequence identity to SEQ ID NO: 29 or SEQ ID NO: 30, and wherein the nucleic acid encoding SEQ ID NO: 31 has at least 95% sequence identity to SEQ ID NO: 32 or SEQ ID NO: 33.

19) The vaccine combination according to any one of embodiments 2-3 and 17-18, wherein the nucleic acid encoding a polypeptide comprising SEQ ID NO: 28 comprises SEQ ID NO: 29 or SEQ ID NO: 30, and wherein the nucleic acid encoding SEQ ID NO: 31 comprises SEQ ID NO: 32 or SEQ ID NO: 33.

20) The vaccine combination according to embodiments 2-3 and 17-19, wherein the nucleic acid encoding a polypeptide comprising SEQ ID NO: 28 has at least 90% sequence identity to SEQ ID NO: 29 and wherein the nucleic acid encoding SEQ ID NO: 31 has at least 90% sequence identity to SEQ ID NO: 32.

21) The vaccine combination according to embodiments 2-3 and 17-20, wherein the nucleic acid encoding a polypeptide comprising SEQ ID NO: 28 has at least 95% sequence identity to SEQ ID NO: 29 and wherein the nucleic acid encoding SEQ ID NO: 31 has at least 95% sequence identity to SEQ ID NO: 32.

22) The vaccine combination according to embodiments 2-3 and 17-21, wherein the nucleic acid encoding a polypeptide comprising SEQ ID NO: 28 comprises SEQ ID NO: 29 and wherein the nucleic acid encoding SEQ ID NO: 31 comprises SEQ ID NO: 32.

23) The vaccine combination according to embodiments 2-3 and 17-19, wherein the nucleic acid encoding a polypeptide comprising SEQ ID NO: 28 has at least 90% sequence identity to SEQ ID NO: 30 and wherein the nucleic acid encoding SEQ ID NO: 31 has at least 90% sequence identity to SEQ ID NO: 33.

24) The vaccine combination according to embodiments 2-3, 17-19 and 23, wherein the nucleic acid encoding a polypeptide comprising SEQ ID NO: 28 has at least 95% sequence identity to SEQ ID NO: 30 and wherein the nucleic acid encoding SEQ ID NO: 31 has at least 95% sequence identity to SEQ ID NO: 33.

25) The vaccine combination according to embodiments 2-3, 17-19 and 23-24, wherein the nucleic acid encoding a polypeptide comprising SEQ ID NO: 28 comprises SEQ ID NO: 29 and wherein the nucleic acid encoding SEQ ID NO: 31 comprises SEQ ID NO: 32.

26) The vaccine combinations according to any one of embodiments 1-25, wherein derivatives of MVA-BN are characterized: i) in being capable of reproductive replication in chicken embryo fibroblasts (CEF) cells and the Baby Hamster Kidney cell line BHK, but not capable of reproductive replication in the human cell lines HaCat, HeLa, and 143B; and ii) by a failure to replicate in a mouse strain that is incapable of producing mature B and T cells and as such is severely immune compromised and highly susceptible to a replicating virus.

27) The vaccine combination according to any one of embodiments 1-26, wherein the recombinant adenovirus vector is selected from the group consisting of rAd26 and rAd35.

28) The vaccine combination according to any one of embodiments 1-27, wherein the recombinant adenovirus vector is rAd26.

29) The vaccine combination according to any one of embodiments 1-27, wherein the recombinant adenovirus vector is rAd35.

30) The vaccine combination according to any one of embodiments 1-29, wherein the first vaccine comprises a first recombinant adenovirus vector comprising the first nucleic acid encoding the first polypeptide comprising SEQ ID NO: 1 and a second recombinant adenovirus vector comprising the second nucleic acid encoding the second polypeptide comprising SEQ ID NO: 20.

31) A recombinant Modified Vaccinia Ankara (MVA) vector comprising: (a) a nucleic acid encoding at least one of a polypeptide comprising the amino acid sequence of SEQ ID NO: 1 and a polypeptide comprising the amino acid sequence of SEQ ID NO: 3, and (b) another nucleic acid encoding at least one of a polypeptide comprising the amino acid sequence of SEQ ID NO: 20 and a polypeptide comprising the amino acid sequence of SEQ ID NO: 22;
wherein the MVA vector is MVA-BN or derivatives thereof 32) The recombinant Modified Vaccinia Ankara (MVA) vector according to embodiment 31, wherein the MVA vector comprises a nucleic acid encoding a polypeptide comprising SEQ ID NO: 1 and a nucleic acid encoding a polypeptide comprising SEQ ID NO: 20.

33) The recombinant MVA vector according to any one of embodiments 31-32, wherein the MVA vector further comprises at least one of a nucleic acid encoding a polypeptide comprising the amino acid sequence of SEQ ID NO: 28 and a nucleic acid encoding a polypeptide comprising the amino acid sequence of SEQ ID NO: 31.

34) The recombinant MVA vector according to any one of embodiments 31-33, wherein the polypeptide comprising SEQ ID NO:1 further comprises SEQ ID NO: 28 and wherein the polypeptide comprising SEQ ID NO: 20 further comprises SEQ ID NO: 31.

35) The recombinant MVA vector according to embodiment 31, wherein the MVA vector comprises a nucleic acid encoding a polypeptide comprising SEQ ID NO: 3 and a nucleic acid encoding a polypeptide comprising SEQ ID NO: 22.

36) The recombinant MVA vector according to claim 31, wherein the nucleic acid encoding a polypeptide comprising SEQ ID NO: 1 is part of a nucleic acid encoding a polypeptide comprising SEQ ID NO: 3, and wherein the nucleic acid encoding a polypeptide comprising SEQ ID NO: 20 is part of a nucleic acid encoding a polypeptide encoding SEQ ID NO: 22.

37) The recombinant MVA vector according to any one of embodiments 31-36, wherein the nucleic acid encoding a polypeptide comprising SEQ ID NO: 1 has at least 90% sequence identity to the polynucleotide sequence of SEQ ID NO: 2 and the nucleic acid encoding a polypeptide comprising SEQ ID NO: 20 has at least 90% sequence identity to the polynucleotide sequence of SEQ ID NO: 21.

38) The recombinant MVA vector according to any one of embodiments 31-37, wherein the nucleic acid encoding a polypeptide comprising SEQ ID NO: 1 has at least 95% sequence identity to SEQ ID NO: 2 and the nucleic acid encoding a polypeptide comprising SEQ ID NO: 20 has at least 95% sequence identity to SEQ ID NO: 21.

39) The recombinant MVA vector according to any one of embodiments 31-38, wherein the nucleic acid encoding a polypeptide comprising SEQ ID NO: 1 comprises SEQ ID NO: 2 and the nucleic acid encoding a polypeptide comprising SEQ ID NO: 20 comprises SEQ ID NO: 21.

40) The recombinant MVA vector according to any one of embodiments 31 and 35, wherein the nucleic acid encoding SEQ ID NO: 3 has at least 90% sequence identity to the polynucleotide sequence of SEQ ID NO: 4 or SEQ ID NO: 24 and the nucleic acid encoding SEQ ID NO: 22 has at least 90% sequence identity to the polynucleotide sequence of SEQ ID NO: 23 or SEQ ID NO: 25.

41) The recombinant MVA vector according to any one of embodiments 31, 35 and 40, wherein the nucleic acid encoding SEQ ID NO: 3 has at least 95% sequence identity to SEQ ID NO: 4 or SEQ ID NO: 24 and the nucleic acid encoding SEQ ID NO: 22 has at least 95% sequence identity to SEQ ID NO: 23 or SEQ ID NO: 25.

42) The recombinant MVA vector according to any one of embodiments 31, 35 and 40-41, wherein the nucleic acid encoding SEQ ID NO: 3 comprises SEQ ID NO: 4 or SEQ ID NO: 24 and the nucleic acid encoding SEQ ID NO: 22 comprises SEQ ID NO: 23 or SEQ ID NO: 25.

43) The recombinant MVA vector according to any one of embodiments 31, 35 and 40-42, wherein the nucleic acid encoding SEQ ID NO: 3 has at least 90% sequence identity to SEQ ID NO: 4 and the nucleic acid encoding SEQ ID NO: 22 has at least 90% sequence identity to SEQ ID NO: 23.

44) The recombinant MVA vector according to any one of embodiments 31, 35, and 40-43, wherein the nucleic acid encoding SEQ ID NO: 3 has at least 95% sequence identity to SEQ ID NO: 4 and the nucleic acid encoding SEQ ID NO: 22 has at least 95% sequence identity to SEQ ID NO: 23.

45) The recombinant MVA vector according to any one of embodiments 31, 35 and 40-44, wherein the nucleic acid encoding SEQ ID NO: 3 comprises SEQ ID NO: 4 and the nucleic acid encoding SEQ ID NO: 22 comprises SEQ ID NO: 23.

46) The recombinant MVA vector according to any one of embodiments 31, 35 and 40-42, wherein the nucleic acid encoding SEQ ID NO: 3 has at least 90% sequence identity to SEQ ID NO: 24 and the nucleic acid encoding SEQ ID NO: 22 has at least 90% sequence identity to SEQ ID NO: 25.

47) The recombinant MVA vector according to any one of embodiments 31, 35, 40-42 and 46, wherein the nucleic acid encoding SEQ ID NO: 3 has at least 95% sequence identity to SEQ ID NO: 24 and the nucleic acid encoding SEQ ID NO: 22 has at least 95% sequence identity to SEQ ID NO: 25.

48) The recombinant MVA vector according to any one of embodiments 31, 35, 40-42 and 46-47, wherein the nucleic acid encoding SEQ ID NO: 3 comprises SEQ ID NO: 24 and the nucleic acid encoding SEQ ID NO: 22 comprises SEQ ID NO: 25.

49) A recombinant MVA vector comprising at least one nucleic acid encoding a polypeptide comprising a sequence selected from the group consisting of: SEQ ID NO: 1, SEQ ID NO: 3, SEQ ID NO: 20, and SEQ ID NO:22, wherein the at least one nucleic acid is operably linked to a promoter comprising at least one of a nucleic acid having at least 95% sequence identity to the polynucleotide sequence of SEQ ID NO: 26 and a nucleic acid having at least 95% sequence identity to the polynucleotide sequence of SEQ ID NO: 27.

50) The recombinant MVA vector according to embodiment 49, wherein the promoter comprises at least one of SEQ ID NO:26 and SEQ ID NO: 27.

51) The recombinant MVA vector according to any one of embodiments 49-50, wherein the promoter is SEQ ID NO:26.

52) The recombinant MVA vector according to any one of embodiments 49-50, wherein the promoter is SEQ ID NO:27.

53) The recombinant MVA vector according to any one of embodiments 49-51, wherein SEQ ID NO: 1 or SEQ ID NO: 3 is operably linked to SEQ ID NO: 26.
54) The recombinant MVA vector according to embodiment 53, wherein SEQ ID NO: 3 is operably linked to SEQ ID NO: 26.
55) The recombinant MVA vector according to any one of embodiments 49-50 or 52, wherein SEQ ID NO: 20 or SEQ ID NO: 22 is operably linked to SEQ ID NO: 27.
56) The recombinant MVA vector according to embodiment 55, wherein SEQ ID NO: 22 is operably linked to SEQ ID NO: 27.
57) The recombinant MVA vector according to any one of embodiments 49 and 53, wherein SEQ ID NO: 1 is encoded by a nucleic acid in accordance with any one of embodiments 5-7 and 36-39.
58) The recombinant MVA vector according to any one of embodiments 49 and 53-54, wherein SEQ ID NO: 3 is encoded by a nucleic acid in accordance with any one of embodiments 4, 8-16, 35, 36, and 40-48.
59) The recombinant MVA vector according to any one of embodiments 49 and 55, wherein SEQ ID NO: 20 is encoded by a nucleic acid according to any one of embodiments 3-7, 32, 34 and 36-39.
60) The recombinant MVA vector according to any one of embodiments 49 and 55-56, wherein SEQ ID NO: 22 is encoded by a nucleic acid according to any one of embodiments 4, 8-16, 35, 36, and 40-48.
61) A vaccine comprising a recombinant MVA vector according to any one of embodiments 31-60 and a pharmaceutically acceptable carrier.
62) A method for treating a persistent HPV infection, vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC)), oropharyngeal cancer, penile cancer, vaginal cancer or anal cancer in a subject, the method comprising administering to the subject a vector, vaccine, or vaccine combination according to any one of embodiments 1-61.
63) A method for inducing an immune response against Human Papilloma Virus (HPV) in a subject, the method comprising:
(a) administering to the subject a first vaccine comprising an immunologically effective amount of either
1. (i) a recombinant adenovirus vector comprising a first nucleic acid encoding a first polypeptide comprising the amino acid sequence of SEQ ID NO:1 and a second nucleic acid encoding a second polypeptide comprising the amino acid sequence of SEQ ID NO: 20, or
2. (ii) a first recombinant adenovirus vector comprising a first nucleic acid encoding a first polypeptide comprising the amino acid sequence of SEQ ID NO:1 and a second recombinant adenovirus vector comprising a second nucleic acid encoding a second polypeptide comprising the amino acid sequence of SEQ ID NO: 20, together with a pharmaceutically acceptable carrier; and
(b) administering to the subject a second vaccine comprising an immunologically effective amount of a recombinant Modified Vaccinia Ankara (MVA) vector comprising a third nucleic acid encoding a third polypeptide comprising the amino acid sequence of SEQ ID NO:1 and a fourth nucleic acid encoding a fourth polypeptide comprising the amino acid sequence of SEQ ID NO: 20, together with a pharmaceutically acceptable carrier;
wherein the first vaccine is administered to the subject as a priming vaccine and the second vaccine is administered to the subject as a boosting vaccine.
64) A method for inducing an immune response against Human Papilloma Virus (HPV) in a subject, the method comprising:
(a) administering to the subject a first vaccine comprising an immunologically effective amount of either
3. (i) a recombinant adenovirus vector comprising a first nucleic acid encoding a first polypeptide comprising the amino acid sequence of SEQ ID NO:1 and a second nucleic acid encoding a second polypeptide comprising the amino acid sequence of SEQ ID NO: 20, or
(ii) a first recombinant adenovirus vector comprising a first nucleic acid encoding a first polypeptide comprising the amino acid sequence of SEQ ID NO:1 and a second recombinant adenovirus vector comprising a second nucleic acid encoding a second polypeptide comprising the amino acid sequence of SEQ ID NO: 20, together with a pharmaceutically acceptable carrier; and
(b) administering to the subject a second vaccine comprising an immunologically effective amount of a recombinant Modified Vaccinia Ankara (MVA) vector comprising a third nucleic acid encoding a third polypeptide comprising the amino acid sequence of SEQ ID NO:1 and a fourth nucleic acid encoding a fourth polypeptide comprising the amino acid sequence of SEQ ID NO: 20, together with a pharmaceutically acceptable carrier;
wherein either the first vaccine or the second vaccine is administered to the subject as a priming vaccine and the other vaccine is administered to the subject as a boosting vaccine.
65) The method according to any one of embodiments 63-64, wherein the first vaccine and the second vaccine each further comprise a nucleic acid encoding a fifth polypeptide comprising the amino acid sequence of SEQ ID NO: 28 and a nucleic acid encoding a sixth polypeptide comprising the amino acid sequence of SEQ ID NO: 31.
66) The method according to any one of embodiments 63-65, wherein each of the first and third polypeptides further comprises SEQ ID NO: 28 and wherein each of the second and third polypeptides further comprises SEQ ID NO: 31.
67) The method according to any one of embodiments 63-66, wherein the first vaccine comprises a first recombinant adenovirus vector comprising a first nucleic acid encoding a first polypeptide comprising SEQ ID NO: 1 or SEQ ID NO: 3 and a second recombinant adenovirus vector comprising a second nucleic acid encoding a second polypeptide comprising SEQ ID NO: 20 or SEQ ID NO: 22.
68) The method according to any one of embodiments 63-67 wherein SEQ ID NO: 1 is encoded by a nucleic acid in accordance with any one of embodiments 5-7 and 36-39.
69) The method according to any one of embodiments 63-67, wherein SEQ ID NO: 3 is encoded by a nucleic acid in accordance with any one of embodiments 4, 8-16, 35, 36 and 40-48.
70) The method according to any one of embodiments 63-67, wherein SEQ ID NO: 20 is encoded by a nucleic acid according to any one of embodiments 3-7, 32, 34 and 36-39.

71) The method according to any one of embodiments 63-67, wherein SEQ ID NO: 22 is encoded by a nucleic acid according to any one of embodiments 4, 8-16, 35, 36 and 40-48.

72) The method according to any one of embodiments 65-66, wherein SEQ ID NO: 28 is encoded by a nucleic acid according to any one of embodiments 17-24.

73) The method according to any one of embodiments 65-66, wherein SEQ ID NO: 31 is encoded by a nucleic acid according to any one of embodiments 17-24.

74) A nucleic acid molecule comprising a polynucleotide sequence selected from the group consisting of SEQ ID NO:24, SEQ ID NO: 25, SEQ ID NO: 30, and SEQ ID NO: 33.

75) A nucleic acid molecule comprising SEQ ID NO:24.

76) A nucleic acid molecule comprising SEQ ID NO:25.

77) A nucleic acid molecule comprising SEQ ID NO: 30.

78) A nucleic acid molecule comprising SEQ ID NO:33.

79) A nucleic acid molecule having at least 90% or 95% sequence identity to the nucleic acid molecules of any one of embodiments 74-78.

80) An isolated nucleic acid molecule comprising the nucleic acid molecule of any one of embodiments 74-79.

81) A vector comprising the nucleic acid molecule of any one of embodiments 74-79.

82) The vector according to embodiment 81, wherein the vector is selected from a poxvirus and an adenovirus.

83) The vector according to any one of embodiments 81-82, wherein the vector is a poxvirus.

84) The vector according to embodiment 83, wherein the poxvirus is an orthopoxvirus or an avipoxvirus.

85) The vector according to embodiment 84, wherein the poxvirus is an orthopoxvirus.

86) The vector according to embodiment 85, wherein the orthopoxvirus is a vaccinia virus.

87) The vector according to embodiment 86, wherein the vaccinia virus is a MVA virus.

88) The vector according to embodiment 87, wherein the MVA virus is MVA-BN or a derivative thereof.

89) The vector according to any one of embodiments 81-82, wherein the vector is an adenovirus.

90) The vector according to embodiment 89, wherein the adenovirus is selected from rAd26 and rAd35.

91) A vaccine combination comprising:
a) a first vaccine comprising an immunologically effective amount of either
  (i) a recombinant adenovirus vector comprising a first nucleic acid encoding a first polypeptide comprising the amino acid sequence of SEQ ID NO: 3 and a second nucleic acid encoding a second polypeptide comprising the amino acid sequence of SEQ ID NO: 22, or
  (ii) a first recombinant adenovirus vector comprising a first nucleic acid encoding a first polypeptide comprising the amino acid sequence of SEQ ID NO: 3 and a second recombinant adenovirus vector comprising a second nucleic acid encoding a second polypeptide comprising the amino acid sequence of SEQ ID NO: 22, together with a pharmaceutically acceptable carrier; and
(b) a second vaccine comprising an immunologically effective amount of a recombinant Modified Vaccinia Ankara (MVA) vector comprising a third nucleic acid encoding a third polypeptide comprising the amino acid sequence of SEQ ID NO: 3 and a fourth nucleic acid encoding a fourth polypeptide comprising the amino acid sequence of SEQ ID NO: 22, together with a pharmaceutically acceptable carrier;
wherein the either the first vaccine or the second vaccine is administered to the subject as a priming vaccine and the other vaccine is administered to the subject as a boosting vaccine; and
wherein the MVA vector comprises MVA-BN or derivatives thereof 92) The vaccine combination according to embodiment 91, wherein a polypeptide comprising SEQ ID NO: 3 is encoded by a nucleic acid in accordance with any one of embodiments 4, 8-16, 35, 36 and 40-48.

93) The vaccine combination according to embodiment 91, wherein a polypeptide comprising SEQ ID NO: 22 is encoded by a nucleic acid according to any one of embodiments 4, 8-16, 35, 36 and 40-48.

94) Use of any one of the nucleic acids, polypeptides, vectors, vaccines, or vaccine combinations according to any one of embodiments 1-61 and 74-93 in treating a persistent HPV infection, vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC)), oropharyngeal cancer, penile cancer, vaginal cancer or anal cancer in a subject in need thereof.

95) Use of any one of the nucleic acids, polypeptides, vectors, vaccines, or vaccine combinations according to any one of embodiments 1-61 and 74-93 in the preparation of a pharmaceutical composition or medicament for inducing an immune response against Human Papilloma Virus (HPV) in a subject in need thereof.

96) A kit comprising any one of the nucleic acids, polypeptides, vectors, vaccines, or vaccine combinations according to any one of embodiments 1-61 and 74-93.

97) The vaccine combination according to embodiment 30, wherein the first recombinant adenovirus vector is rAd26 and the second recombinant adenovirus vector is rAd26.

98) The vaccine combination according to embodiment 97, wherein the first recombinant adenovirus vector comprises a first nucleic acid encoding a first polypeptide comprising SEQ ID NO: 3 and the second recombinant adenovirus vector comprises a second nucleic acid encoding a second polypeptide comprising SEQ ID NO: 22.

99) The vaccine combination according to embodiment 91, wherein the first vaccine comprises an immunologically effective amount of a recombinant adenovirus vector comprising a first nucleic acid encoding a first polypeptide comprising SEQ ID NO: 3 and a second nucleic acid encoding a second polypeptide comprising SEQ ID NO: 22, together with a pharmaceutically acceptable carrier.

100) The vaccine combination according to embodiment 99, wherein the recombinant adenovirus vector is rAd26.

101) The vaccine combination according to embodiment 91, wherein the first vaccine comprises an immunologically effective amount of a first recombinant adenovirus vector comprising a first nucleic acid encoding a first polypeptide comprising SEQ ID NO: 3 and a second recombinant adenovirus vector comprising a second nucleic acid encoding a second polypeptide comprising SEQ ID NO: 22, together with a pharmaceutically acceptable carrier.

102) The vaccine combination according to embodiment 101, wherein the first recombinant adenovirus vector is rAd26 and the second recombinant adenovirus vector is rAd26.

103) The vaccine combination according to any one of embodiments 91 and 99-102, wherein the first vaccine is a priming vaccine and the second vaccine is a boosting vaccine.

104) A method for treating persistent HPV infection, vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC)), oropharyngeal cancer, penile cancer, vaginal cancer or anal cancer in a subject in need thereof, the method comprising:

(a) administering to the subject a first vaccine comprising an immunologically effective amount of either 4. (i) a recombinant adenovirus vector comprising a first nucleic acid encoding a first polypeptide comprising the amino acid sequence of SEQ ID NO:1 and a second nucleic acid encoding a second polypeptide comprising the amino acid sequence of SEQ ID NO: 20, or 5. (ii) a first recombinant adenovirus vector comprising a first nucleic acid encoding a first polypeptide comprising the amino acid sequence of SEQ ID NO:1 and a second recombinant adenovirus vector comprising a second nucleic acid encoding a second polypeptide comprising the amino acid sequence of SEQ ID NO: 20, together with a pharmaceutically acceptable carrier; and (b) administering to the subject a second vaccine comprising an immunologically effective amount of a recombinant Modified Vaccinia Ankara (MVA) vector comprising a third nucleic acid encoding a third polypeptide comprising the amino acid sequence of SEQ ID NO:1 and a fourth nucleic acid encoding a fourth polypeptide comprising the amino acid sequence of SEQ ID NO: 20, together with a pharmaceutically acceptable carrier;

wherein the first vaccine is administered to the subject as a priming vaccine and the second vaccine is administered to the subject as a boosting vaccine.

105) The method according to any one of embodiments 63, 64 or 104, wherein the first vaccine comprises an immunologically effective amount of a first recombinant adenovirus vector comprising a first nucleic acid encoding a first polypeptide comprising SEQ ID NO: 1 and a second recombinant adenovirus vector comprising a second nucleic acid encoding a second polypeptide comprising SEQ ID NO: 20, together with a pharmaceutically acceptable carrier.

106) The method according to embodiment 105, wherein the first recombinant adenovirus vector is rAd26 and the second recombinant adenovirus vector is rAd26.

107) THE METHOD ACCORDING TO ANY ONE OF EMBODIMENTS 63, 64 OR 104, WHEREIN THE FIRST VACCINE COMPRISES AN IMMUNOLOGICALLY EFFECTIVE AMOUNT OF A RECOMBINANT ADENOVIRUS VECTOR COMPRISING A FIRST NUCLEIC ACID ENCODING A FIRST POLYPEPTIDE COMPRISING SEQ ID NO: 1 AND A SECOND NUCLEIC ACID ENCODING A SECOND POLYPEPTIDE COMPRISING SEQ ID NO: 20, TOGETHER WITH A PHARMACEUTICALLY ACCEPTABLE CARRIER

108) THE METHOD ACCORDING TO EMBODIMENT 107, WHEREIN THE RECOMBINANT ADENOVIRUS VECTOR IS RAD26.

109) THE METHOD ACCORDING TO ANY ONE OF EMBODIMENTS 104-108, WHEREIN THE NUCLEIC ACID ENCODING A POLYPEPTIDE COMPRISING SEQ ID NO: 1 IS PART OF A NUCLEIC ACID ENCODING A POLYPEPTIDE COMPRISING SEQ ID NO: 3, AND WHEREIN THE NUCLEIC ACID ENCODING A POLYPEPTIDE COMPRISING SEQ ID NO: 20 IS PART OF A NUCLEIC ACID ENCODING A POLYPEPTIDE ENCODING SEQ ID NO: 22.

110) A recombinant Modified Vaccinia Ankara (MVA) vector comprising: (a) a nucleic acid encoding at least one of a polypeptide comprising the amino acid sequence of SEQ ID NO: 1 and a polypeptide comprising the amino acid sequence of SEQ ID NO: 3, and (b) a nucleic acid encoding at least one of a polypeptide comprising the amino acid sequence of SEQ ID NO: 20 and a polypeptide comprising the amino acid sequence of SEQ ID NO: 22;

6. wherein at least one of the nucleic acids from (a) and (b) is inserted in the MVA intergenic region (IGR) 88/89.

111) The recombinant MVA vector according to embodiment 110, wherein the nucleic acids from both (a) and (b) are inserted into the MVA intergenic region (IGR) 88/89.

112) The recombinant MVA vector according to any one of embodiments 110-111, wherein the MVA is MVA-BN or derivatives thereof.

113) The recombinant Modified Vaccinia Ankara (MVA) vector according to any one of embodiments 110-112, wherein the MVA vector comprises a nucleic acid encoding a polypeptide comprising SEQ ID NO: 1 and a nucleic acid encoding a polypeptide comprising SEQ ID NO: 20.

114) The recombinant MVA vector according to any one of embodiments 110-113, wherein the MVA vector further comprises at least one of a nucleic acid encoding a polypeptide comprising SEQ ID NO: 28 and a nucleic acid encoding a polypeptide comprising SEQ ID NO: 31.

115) The recombinant MVA vector according to any one of embodiments 110-114, wherein the polypeptide comprising SEQ ID NO:1 further comprises SEQ ID NO: 28 and wherein the polypeptide comprising SEQ ID NO: 20 further comprises SEQ ID NO: 31.

116) The recombinant MVA vector according to embodiment 110, wherein the MVA vector comprises a nucleic acid encoding a polypeptide comprising SEQ ID NO: 3 and a nucleic acid encoding a polypeptide comprising SEQ ID NO: 22.

The practice of this invention will employ, unless otherwise indicated, conventional techniques of immunology, molecular biology, microbiology, cell biology, and recombinant DNA, which are within the skill of the art. See e.g. Sambrook, Fritsch and Maniatis, Molecular Cloning: A Laboratory Manual, 2$^{nd}$ edition, 1989; Current Protocols in Molecular Biology, Ausubel F M, et al., eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

The invention is further explained in the following examples. The examples do not limit the invention in any way. They merely serve to clarify the invention.

EXAMPLES

Example 1: Construction of a Designer Polypeptide Comprising Essentially all HPV16 E6 and E7 CTL Epitopes We designed a novel, non-tumorigenic polypeptide (and nucleic acid encoding such) that contains essentially all CTL epitopes of HPV16 E6 and E7 proteins, and has a minimum number of anticipated/predicted strong neo-epitopes (neo-epitopes meaning epitopes not present in the wild type HPV16 E6 and E7 proteins). A polypeptide of the invention (also sometimes referred to as 'E6E7SH' herein) for HPV16 comprises a sequence as provided in SEQ ID NO: 1. A codon-optimized nucleic acid encoding this polypeptide is provided in SEQ ID NO: 2.

The molecules of the invention are single molecules, which provides manufacturing advantages over strategies where multiple molecules are used. In addition, a polypeptide of the invention comprises essentially all putative CTL epitopes that are present in wild-type E6 and E7 of HPV16, and at the same time have a minimum number of anticipated/predicted strong neo-epitopes that could potentially be immunodominant and thus divert the immune response from relevant wild-type CTL epitopes. Thus the constructs of the present invention are immunologically more favourable than molecules described by others that either lack possible CTL epitopes and/or that contain more or stronger neo-epitopes.

For instance, the construct of SEQ ID NO: 1 contains only one neo-epitope with a length of nine amino acids with a predicted binding affinity <50 nM for the 20 most common HLA-A, 20 most common HLA-B and 20 most common HLA-C alleles (HLA-A*01:01, HLA-A*02:01, HLA-A*02:03, HLA-A*02:06, HLA-A*02:07, HLA-A*03:01, HLA-A*11:01, HLA-A*23:01, HLA-A*24:02, HLA-A*26:01, HLA-A*29:02, HLA-A*30:01, HLA-A*30:02, HLA-A*31:01, HLA-A*32:01, HLA-A*33:01, HLA-A*33:03, HLA-A*34:01, HLA-A*68:01, HLA-A*68:02, HLA-B*07:02, HLA-B*07:04, HLA-B*08:01, HLA-B*13:01, HLA-B*15:01, HLA-B*18:01, HLA-B*35:01, HLA-B*37:01, HLA-B*39:01, HLA-B*40:01, HLA-B*40:02, HLA-B*40:06, HLA-B*44:02, HLA-B*44:03, HL-B*46:01, HLA-B*48:01, HLA-B*51:01, HLA-B*52:01, HLA-B*53:01, HLA-B*58:01, HLA-C*07:02, HLA-C*04:01, HLA-C*03:04, HLA-C*01:02, HLA-C*07:01, HLA-C*06:02, HLA-C*03:03, HLA-C*08:01, HLA-C*15:02, HLA-C*12:02, HLA-C*02:02, HLA-C*05:01, HLA-C*14:02, HLA-C*03:02, HLA-C*16:01, HLA-C*08:02, HLA-C*12:03, HLA-C*04:03, HLA-C*17:01, HLA-C*14:03), as determined using the ANN (Lundegaard et al., 2008, *Nucl Acids Res* 36: W509-12) and SMM method (Peters et al., 2003, *Bioinformatics* 19: 1765-72) for HLA-A and HLA-B and the NetMHCpan method (Hoof et al., 2009, *Immunogenetics* 61: 1-13) for HLA-C of the prediction tool for 'Peptide binding to MHC class I molecules' at the IEDB website (http://tools.immuneepitope.org/analyze/html/mhc_binding.html, version 2009-09-01B).

As a non-limiting example, using the SMM prediction tool at the IEDB website, the shuffled E6 and E7 sequences as described by Oosterhuis et al., 2011, *Int J Cancer* 129: 397-406 and Öhlschläger et al., 2006, *Vaccine* 24: 2880-93 contain each nine potential strong unique neo-epitopes (ANN or SMM IC50<50 nM) for the 20 most HLA-A and —B, in the core part. This even excludes the appendices used in that approach (in which appendices will further contribute to additional neo-epitopes, and may miss out on more native MHC II epitopes due to the limited length of the 'overlap'). Indeed, a reportedly improved molecule containing a variant with shuffled E6 and E7 proteins that was described in WO 2013/083287, contains 22 unique neo-epitopes with a length of nine amino acids with a predicted IC50<50 nM (ANN, SMM or NetMHCPan) for the 20 most common HLA-A, 20 most common HLA-B and 20 most common HLA-C alleles.

Hence, the designer molecules of the invention clearly are favourable in having much lower number of predicted neo-epitopes compared to other published approaches where E6 and E7 where shuffled to remove functionality.

Nucleic acid encoding our thus designed HPV16 E6E7SH molecule (i.e. a polypeptide having amino acid sequence as provided in SEQ ID NO:1) was synthesized, the nucleic acid sequence comprising SEQ ID NO: 2, and flanked by a HindIII site and a Kozak sequence on the 5'end and an XbaI site on the 3' site (custom synthesis and standard molecular cloning at Invitrogen Life technologies, Germany).

The synthezised fragments were cloned using HindIII and XbaI into a standard expression vector, pCDNA2004.Neo, harbouring both a bacterial resistance marker (Ampiciline) and a mammalian resistance marker (Neomycine), to obtain plasmid vectors encoding a molecule of the invention, e.g. for (transient) transfection based experiments.

These molecules could be used as such, but also as the basis for further molecules that contain additional features. As non-limiting examples, some further variants were prepared as described below.

The HPV16 E6E7SH fusion protein sequence can be combined with sequences of other HPV16 early proteins to target individuals with persistent infection and to broaden the immune repertoire in an immunized individual. Immune responses against E2 have been suggested to play an important role in the clearance of HPV16 infections (de Jong et al., 2002, *Cancer Res* 62: 472-479). Fusion of E2 to E6E7SH will give a vaccine component that harbours antigens against the stages of HPV-related cancer from persistent infection to invasive cancer or recurrent/refractory disease after LEEP surgery. Therefore, as a non-limiting example of such embodiments, we prepared a sequence coding for a fusion protein of E6E7SH with E2 at its N-terminus. In the E2 sequence modifications can be made to abrogate DNA binding activity that might affect gene expression in cells expressing the fusion protein. We mutated Glycine at position 293, Lysine at position 299 and Cysteine at position 300 of the wt HPV16 E2 protein into respectively Valine, Methionine and Arginine. Each of these mutations on its own already completely abrogates the binding of E2 to DNA sequences that harbour E2 binding domains (Prakash et al., 1992, *Genes Dev* 6: 105-16).

The resulting polypeptide is referred to as HPV16 E2E6E7SH and comprises SEQ ID NO: 3. A codon-optimized sequence encoding this polypeptide was prepared and is provided in SEQ ID NO: 4.

We also constructed a variant wherein the same E2 mutant protein was fused to the C-terminus of the HPV16 E6E7SH fusion polypeptide, giving rise to a polypeptide referred to as HPV16 E6E7E2SH, which comprises SEQ ID NO: 5. The sequence encoding this construct is provided as SEQ ID NO: 6.

For control purposes, we also constructed sequences encoding a polypeptide that contains the wild-type sequences for full-length HPV16 E6 and E7 as a fusion protein (E6 from aa 1 to 158 directly fused to E7 from aa 1 to 98, named herein E6E7 wt).

We also tested the effect of adding leader sequences to the polypeptide. As a non-limiting example, a sequence encoding an IgE leader sequence (see e.g. U.S. Pat. No. 6,733,994) [the sequence of the leader peptide is provided in SEQ ID NO: 7] was fused at the N-terminus of some of the constructs, e.g. in the E6E7 wt construct, which rendered LSE6E7 wt, and in the E2E6E7SH construct, which rendered LSE2E6E7SH. The effect thereof was significantly (p<0.05) enhanced immunogenicity in comparison to the same antigen without the LS sequence as measured by E7-tetramer analysis in immunized mice (as can for instance be seen in FIG. 9).

The sequences that encode the E6E7SH polypeptides of the invention, with or without E2, can for instance be expressed from DNA constructs, from RNA or from viral vectors. FIG. 1 demonstrates expression in HEK-293T cells upon transient transfection with DNA vectors expressing the transgenes as described above. After transfection, cells were harvested and cell extracts were analyzed by SDS-PAGE and western blotting with an antibody against HPV16 E7. This experiment demonstrates expression of the expected fusion proteins of appropriate size upon transfection of the expression vectors.

Adenoviral vectors can be used to express the E6E7, either with or without E2, and with or without additional sequences to augment the immunogenicity of the encoded fusion protein.

The genes, coding for HPV16 E6E7 wt control or HPV16 designer sequences described above were gene optimized for human expression and synthesized, at Geneart. A Kozak sequence (5' GCCACC 3') was included directly in front of the ATG start codon, and two stop codons (5' TGA TAA 3') were added at the end of the respective coding sequence. The genes were inserted in the pAdApt35BSU plasmid and in the pAdApt26 plasmid (Havenga et al., 2006, *J Gen Virol* 87, 2135-43) via HindIII and XbaI sites.

All adenoviruses were generated in PER.C6 cells by single homologous recombination and produced as previously described (for rAd35: Havenga et al., 2006, *J Gen Virol* 87: 2135-43; for rAd26: Abbink et al., 2007, *J Virol* 81: 4654-63). PER.C6 cells (Fallaux et al., 1998, *Hum Gene Ther* 9: 1909-17) were maintained in Dulbecco's modified Eagle's medium (DMEM) with 10% fetal bovine serum (FBS), supplemented with 10 mM MgCl2.

Briefly, PER.C6 cells were transfected with Ad vector plasmids, using Lipofectamine according to the instructions provided by the manufacturer (Life Technologies). Cells were harvested one day after full cytopathic effect (CPE) was reached, freeze-thawed, centrifuged for 5 min at 3,000 rpm, and stored at −20° C. The viruses were plaque purified and amplified in PER.C6 cells cultured in a single well of a multiwell 24 tissue culture plate. Further amplification was carried out in PER.C6 cells cultured in a T25 tissue culture flask and subsequently in a T175 tissue culture flask. Of the crude lysate prepared from the cells obtained after the T175 flask, 3 to 5 ml was used to inoculate 24×T1000 five-layer tissue culture flasks containing 70% confluent layers of PER.C6 cells. The virus was purified using a two-step CsCl purification method. Finally, the virus was stored in aliquots at −85° C.

Ad35.HPV16-E6E7 wt, and Ad35.HPV16-E6E7SH are recombinant adenovirus serotype 35 (Ad35) vectors comprising the codon-optimized nucleotide sequences for the expression of, respectively, a fusion protein of the wild type HPV16 E6 and E7 proteins (E6E7 wt), and a designer fusion protein variant as described above (E6E7SH, having the amino acid sequence provided in SEQ ID NO: 1). The combined E6 and E7 sequences were placed under the control of a CMV promoter in the E1 region of the E1,E3 deleted adenovirus genome. Ad26.HPV16-E6E7 wt, and Ad26.HPV16-E6E7SH are the equivalent vectors based on recombinant adenovirus serotype 26.

Similarly, Ad26 and Ad35-based recombinant adenoviral vectors were produced that encode the HPV16 E2E6E7SH (SEQ ID NO: 3) variant. Likewise, Ad26 and Ad35 encoding the HPV16 E6E7E2SH (SEQ ID NO: 5) variant were produced. Also, an Ad35 vector encoding the E2E6E7SH fusion protein with an IgE leader sequence at the N-terminus was produced, named Ad35.HPV16-LSE2E6E7SH. Also a control adenovirus with the E6E7 wt fused to the IgE leader sequence at the N-terminus was produced.

The recombinant adenoviruses were produced on PER.C6 cells and purified by centrifugation on cesium chloride gradients.

Further examples of constructs that were coupled to repressor systems are provided in a later example below.

Example 2. Lack of Transforming Activity of the HPV16 Designer Constructs

Wild-type HPV16 E6 and E7 proteins have tumorigenic potential, which is apparent as transforming activity in certain assays, such as colony formation in a soft-agar assay (Massimi and Banks, 2005, *Methods Mol Med* 119: 381-395). The E6E7SH polypeptide as described in example 1 comprises the fragments of the E6 and E7 proteins in a re-ordered fashion. This is expected to remove the tumorigenic potential, as can be measured for instance by a significantly reduced transforming activity as compared to either of wt E6 and E7 proteins in such assays.

Others reported that gene-shuffled variants of HPV16 E6 and E7 have indeed lost their oncogenic potential (Öhlschläger et al., 2006, *Vaccine* 24: 2880-93; Henken et al., 2012, *Vaccine* 30: 4259-66), demonstrating that gene shuffling destroys the wild-type functions of E6 and E7 proteins.

Figure 2:
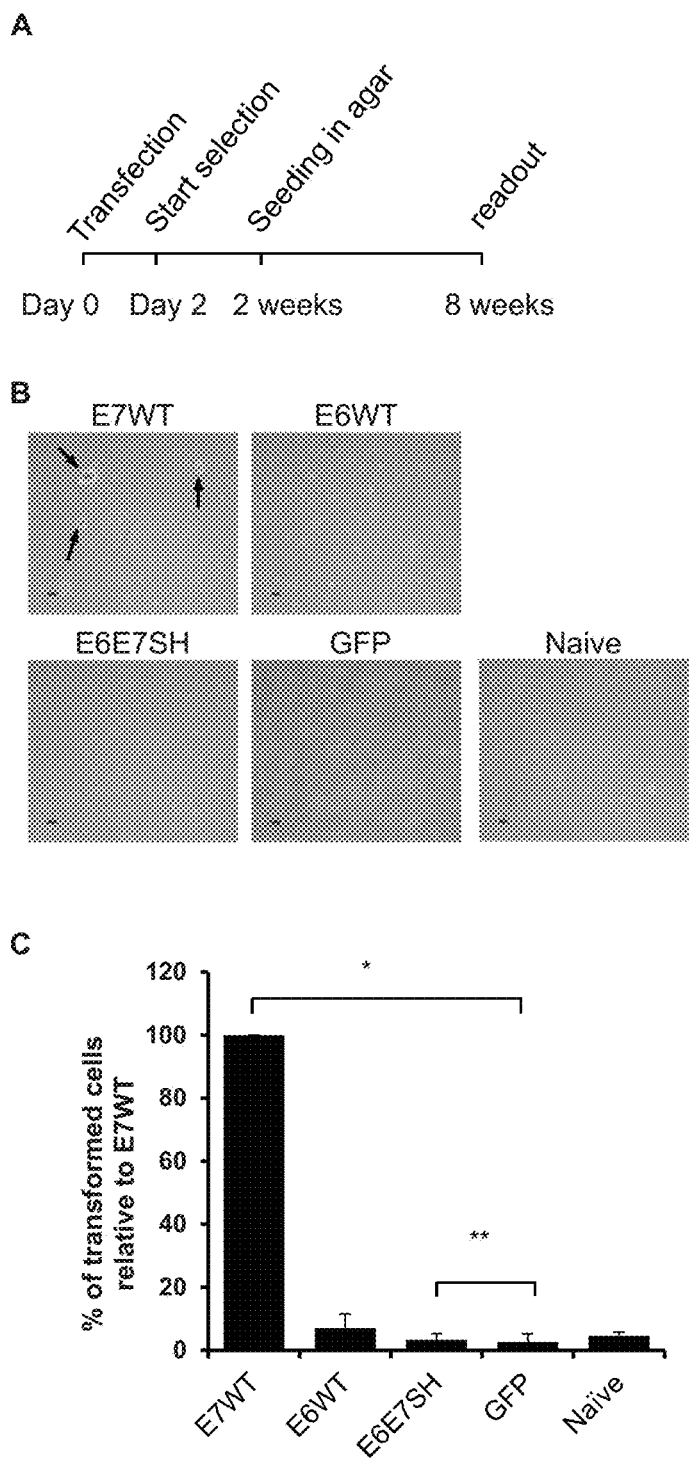
FIG. 2. Colony formation in soft agar. A) Schematic representation of the setup of the soft-agar assay. B) Representative microscopic images at 40× magnification of the cells in agar six weeks post seeding. The white arrows highlight colonies observed in the E7 wt transfected cells. C) Colony quantification six weeks post seeding in agar using the Gelcount™ and associated software. *: $p<0.05$ (Poisson regression model); **: non-inferior (generalized linear model with non-inferiority margin of 5%).

To assess the loss of tumorigenic properties, we assessed the ability of our E6E7SH constructs to confer the ability to grow in soft agar upon NIH 3T3 cells (as described by e.g. Massimi and Banks, 2005, *Methods Mol Med* 119: 381-395). Transfection of NIH3T3 cells with a plasmid expressing the wild type HPV16 E7 resulted consistently in colony formation. In these assays, expression of wild type HPV16 E6 alone did not cause colony formation above background. This is in line with published observations that E7 wt is much more efficient than E6 wt in this assay (Sedman et al., 1991, *J Virol* 65: 4860-66). Transfection with our E6E7SH construct did not lead to growth of colonies of cells in soft agar (FIG. 2) in four independent experiments, demonstrating that nucleic acids encoding a polypeptide of the invention, E6E7SH, have lost the transforming capacity that is associated with E7.

Figure 3:
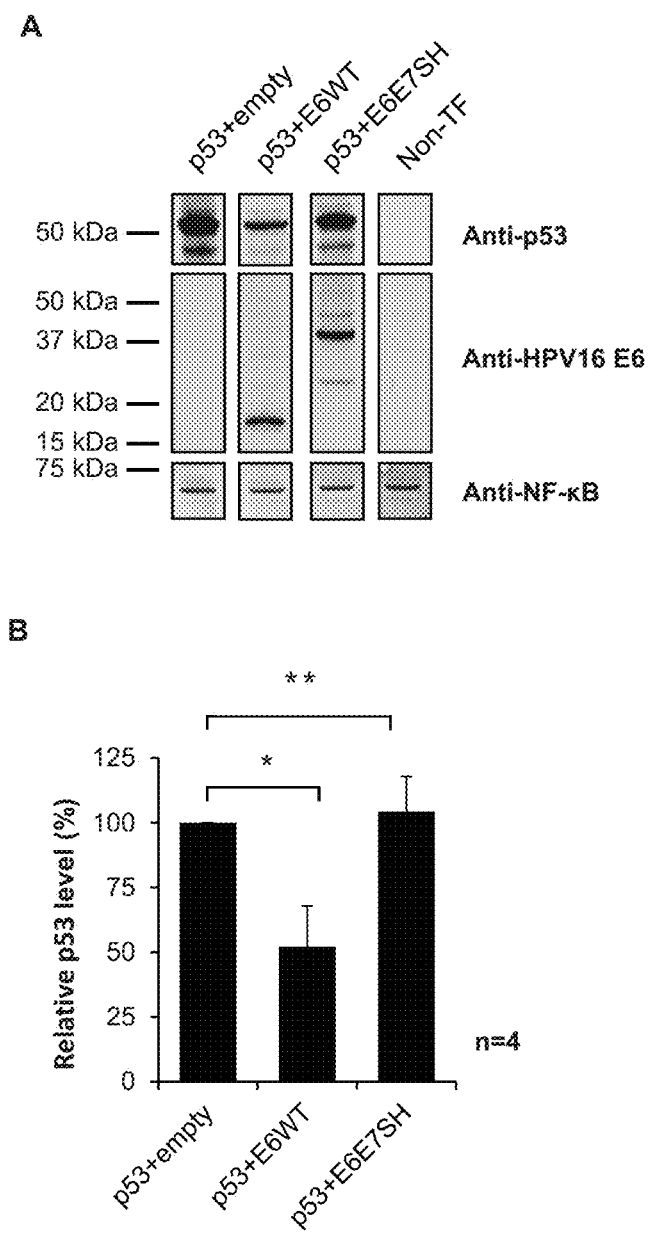
FIG. 3. HPV16 E6E7SH has lost E6 and E7 activities. A) Representative western blot demonstrating absence of p53 degradation by E6E7SH. Human p53 null NCI-H1299 cells were co-transfected with a plasmid expressing p53 in combination with a plasmid expressing HPV16 E6 wild-type, HPV16 E6E7SH or the empty vector. Non-TF indicates non-transfected cells. 24 hours after transfection cell lysates were prepared and 30 μg of total protein was loaded on gel. Upper panel—p53 staining, middle panel—E6 staining, lower panel—NF-kB staining (loading control). (B) Quantification of p53 levels in four independent assays. The p53 signal was normalized to the NF-κB signal. C) Western blot demonstrating lack of pRb degradation by E6E7SH. pRb null Saos-2 cells were transfected with a plasmid expressing pRb in combination with a plasmid expressing HPV16 E7 wild-type, HPV16 E6E7SH or the empty vector. Non-TF indicates non-transfected cells. 24 hours after transfection cell lysates were prepared and 10 μg of total protein was loaded on gel. Upper panel—pRb staining, middle panel—E7 staining, lower panel—NF-κB staining (loading control). D) Quantification of pRb levels in four independent assays. The pRb signal was normalized to the NF-κB signal. *: $p<0.05$ (ANOVA models); **: non-inferior (testing was based on 95% CI's derived from ANOVA models. Non-inferiority margin was set at 75%).

The tumorigenic potential of E6 and E7 is associated with their ability to reduce the levels of the cellular proteins p53 and pRb respectively. p53 and pRb degradation assays were performed to demonstrate that nucleic acid encoding a polypeptide of the invention, E6E7SH, construct does not have the biological activity associated with the wild-type E6 and E7 at the molecular level. In short, HPV16 E6 wt and our E6E7SH construct were expressed in NCI-H1299 cells that lack endogenous p53 for the p53 degradation assay. For the pRb degradation assay HPV16 E7 wt and the E6E7SH construct were expressed in pRb null Saos-2 cells. As can be seen in FIG. 3, co-expression of p53 with E6 wt, but not with E6E7SH, leads to reduced p53 levels (panels A and B). Likewise, panels 3C and 3D show that co-expression of pRb with E7 wt, but not with E6E7SH, leads to reduced pRB levels. These data demonstrate that nucleic acid encoding a polypeptide of the invention has no ability to form colonies in soft agar and does not contain main biological activities of the wild-type E6 and E7 polypeptides, namely the inactivation of p53 and pRb respectively.

Figure 4:
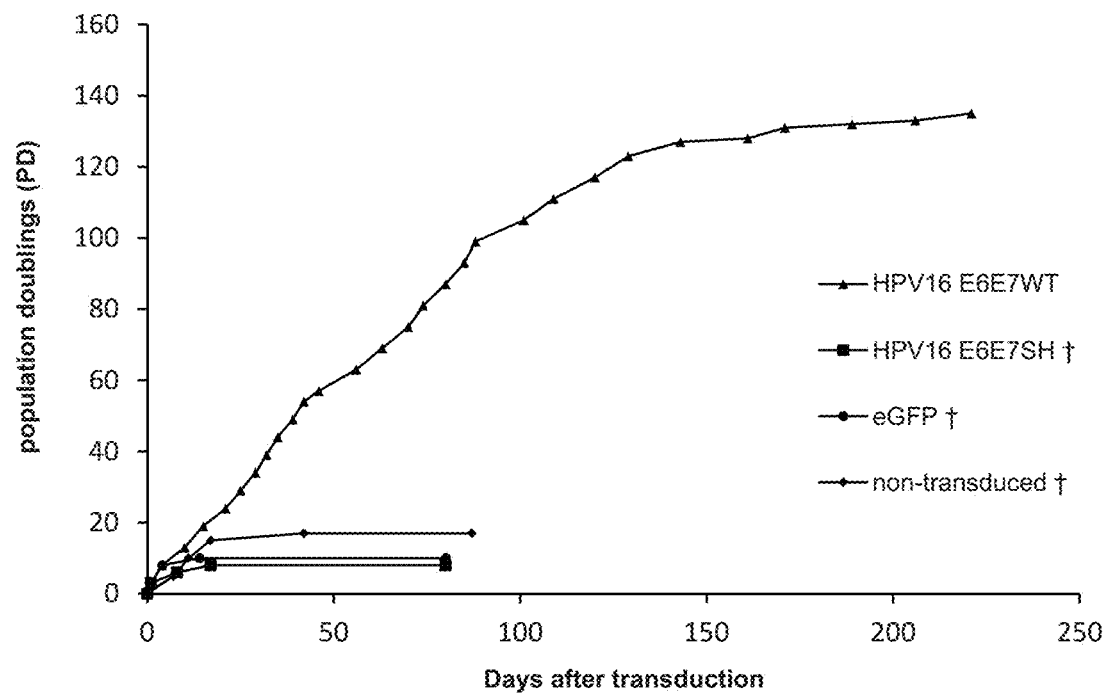
FIG. 4. HPV16 E6E7SH does not immortalize primary human epidermal keratinocytes. Primary human epidermal keratinocytes were transduced with lentiviruses encoding either the wild-type E6- and E7-encoding open reading frame of HPV16 (E6E7 wt), the HPV16 E6E7SH sequence or eGFP. Non-transduced donor cells were used as a control. Only expression of E6E7 wt induces immortalization of primary keratinocytes as indicated by the extended lifespan and hTERT activation around day 200 (not shown). The cross symbol indicates that the cells died in senescence and could not be further cultured. For details see example 2. Similar results were obtained in two additional donors (not shown).

To further demonstrate the safety of nucleic acid constructs encoding polypeptide of the invention, we made use of primary human foreskin keratinocytes that are the natural target cells for HPV mediated transformation. Immortalization of primary human keratinocytes requires the action of both E6 and E7 wild-type (Munger et al., 1989, *J Virol* 63: 4417-21). This assay is probably the physiologically most relevant in vitro assay to demonstrate the safety of our constructs (Massimi and Banks, 2005, *Methods Mol Med* 119: 381-395). Cells transduced with lentiviruses expressing wild type E6 and E7 from HPV16 (E6E7 wt) induce immortalization in primary keratinocytes as indicated by the extension of their lifespan as compared to non-transduced control cells (FIG. 4) and activation of hTERT, the catalytic subunit of telomerase (data not shown). Expression of a polypeptide of the invention (E6E7SH) is not able to to extend the lifespan compared to GFP-transduced or non-transduced keratinocytes. A similar result was obtained in two additional independent donors (data not shown). Taken together these data demonstrate that our constructs have lost the ability to induce immortalization in primary human keratinocytes, that are considered a highly physiological model.

Another construct wherein comparable fragments of HPV16 E6 and E7 were recombined in a different order was also incapable of immortalization of primary human foreskin keratinocytes. However, an expanded life span up to approximately 120-150 days was observed for that construct. This indicates some unpredictability in this field, and demonstrates the superiority of the selected designer molecules according to the invention in this safety-related aspect.

All together the experiments in this example provide strong evidence of the lack of transforming activity of nucleic acids encoding HPV16 designer polypeptides according to the invention, and thus a strongly improved safety over HPV16 E6 and E7 wt constructs.

Example 3. Immune Responses to the HPV16 E6E7SH Designer Constructs

We have prepared DNA vectors and adenoviral vectors, as described in example 1.

Figure 5:
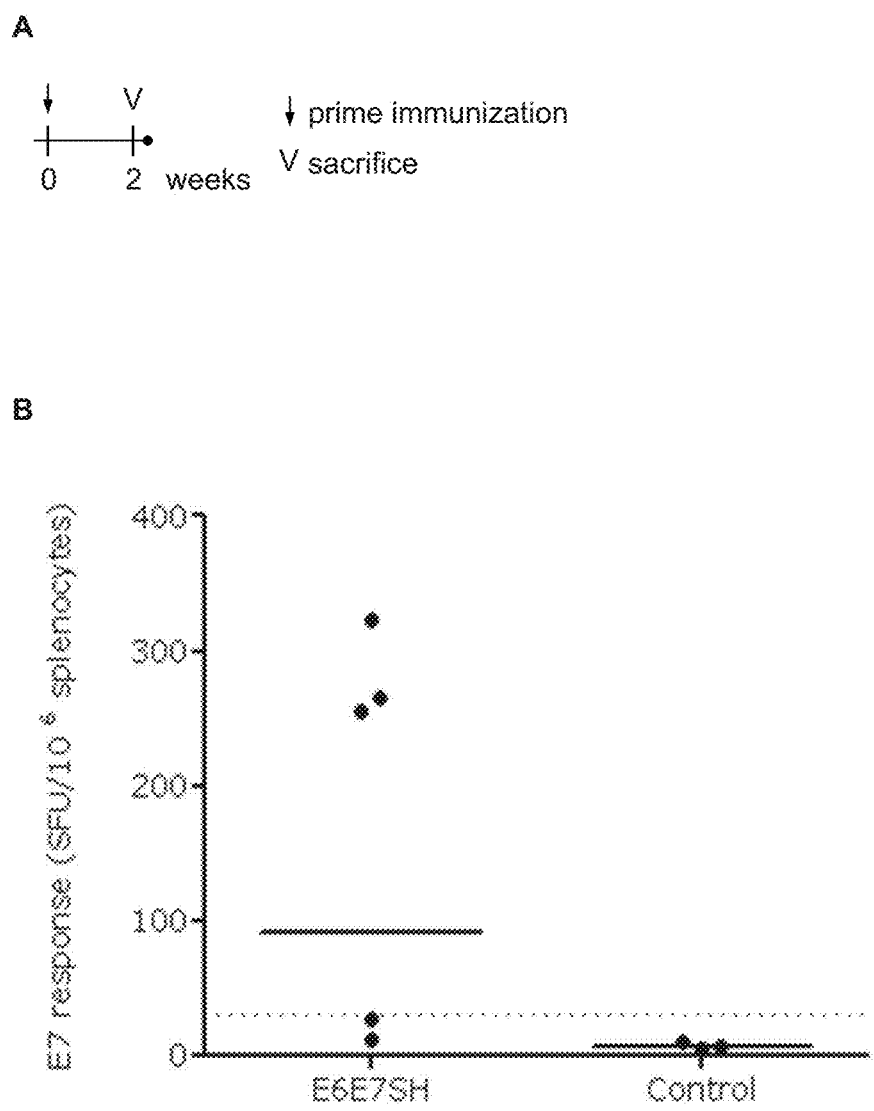
FIG. 5. Immune response induced by HPV16 E6E7SH after DNA immunization—IFNγ ELISPOT analysis. A. Immunization scheme. CB6F1 mice were immunized with DNA plasmids expressing HPV16 E6E7SH or a plasmid expressing no transgene (control). Two weeks after immunization the mice were sacrificed and isolated splenocytes were stimulated overnight with 15mer peptide pools corresponding to E7. B. HPV16 E7-specific immune responses in individual mice as measured by IFNγ ELISPOT assays are given as spot forming units (SFU) per $10^6$ splenocytes.

We used the CB6F1 mouse strain for measuring immune responses, based on initial experiments where mice where immunized with DNA plasmids encoding wild type E2, or E6 or E7, and immunization with HPV16 E2, E6 and E7 antigens induced a broader cellular immune response in CB6F1 than in C57BL/6 mice or Balb/c mice. In a separate experiment mice were immunized with DNA vectors encoding molecules of the invention and cellular immune responses were measured. HPV16 E7-specific immune responses could be measured in mice immunized with DNA plasmids expressing E6E7SH (FIG. 5).

The following data shown in this example are from mouse experiments that were carried out with adenoviral vectors.

To evaluate the vaccine induced immunogenicity, CB6F1 mice were immunized with adenovectors (Ad35) expressing HPV16 E6E7 wt, LSE6E7 wt, E6E7SH or adenovectors not encoding a transgene (Empty). Two doses were tested for administration to the mice: $5*10^9$ viral particles (vp) and $1*10^{10}$ vp. Two and eight weeks after immunization the mice were sacrificed and isolated splenocytes were stimulated overnight with an HPV16 E7 15mer peptide pool. E7-specific responses at two weeks and at eight weeks were analyzed by IFNγ ELISPOT. The data are presented in FIG. 6.

This shows that immunization of mice with Ad35.HPV16-E6E7SH induces E7-specific immune responses as measured by ELISPOT analysis. In addition, the results in FIG. 6 demonstrates the possibility to enhance the immune response against an adenoviral expressed transgene by adding an N-terminal leader sequence to the transgene.

Figure 7:
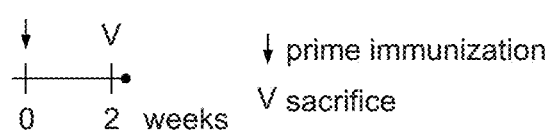
FIG. 7. Immunogenicity of HPV16 E2E6E7SH-E7-tetramer staining. (A). Immunization scheme. CB6F1 mice were immunized with $1*10^{10}$ vp of adenovectors expressing the transgenes as indicated. Two weeks after immunization the mice were sacrificed and isolated splenocytes analyzed for the presence of CD8+ cells capable of interacting with $E7_{49-57}$-H2-Db tetramers (B). The percentage of E7-tetramer positive CD8+ T-cells is indicated on the y-axis. ANOVA Post-hoc Bonferroni statistical analysis was performed on log transformed data, the differences between the different E6E7SH variants were not statistically significant.
Figure 7:

Next the effect of adding HPV16 E2 to the HPV16 E6E7SH polypeptide with respect to immunogenicity was tested. The Ad35 vectors encoded polypeptides that had E2 either fused to the N-terminus (E2E6E7SH) or to the C-terminus (E6E7E2SH). CB6F1 mice were immunized with a dose of $1\times10^{10}$ vp. FIG. 7 (E7-tetramer staining) and FIG. 8 (Panel C, IFNγ ELISPOT) show the immune responses against E7, which for the designer constructs including E2 tends to be higher in comparison to the construct without E2, although the differences were not statistically significant. The response against E2 was higher for adenoviral vectors encoding only E2 compared to the response for adenoviral vectors that had E2 fused to the E6E7SH designer polypeptide (FIG. 8B), with differences being significant for both E2 vs E2E6E7SH and E2 vs E6E7E2SH (p-value: <0.05).

It is concluded that the designer constructs that further include E2 can still provide an immune response against E7, and in addition also provide an immune response against E2, thus increasing the breadth of the immune response over the constructs that do not include E2.

Figure 8:
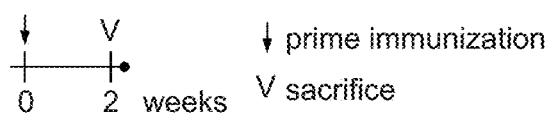
FIG. 8. Immunogenicity of HPV16 E2E6E7SH—IFNγ ELISPOT analysis. (A). Immunization scheme. CB6F1 mice were immunized with adenovectors expressing the transgenes indicated below panels B and C. Two weeks after immunization the mice were sacrificed and isolated splenocytes were stimulated overnight with 15mer peptide pools corresponding to E2 (B), E6 (not shown) or E7 (C). Responses are given as SFU per $10^6$ splenocytes. ANOVA Post-hoc Bonferroni statistical analysis was performed on log transformed data. The E2 response induced by Aden-ovectors encoding E2 alone is higher than the response induced by the polypeptides of the invention that include the E6 and E7 fragments. The difference is significant for E2 vs E2E6E7SH and E2 vs E6E7E2SH (*: p<0.05). ANOVA Post-hoc Bonferroni statistical analysis was performed on log transformed data.
Figure 8:
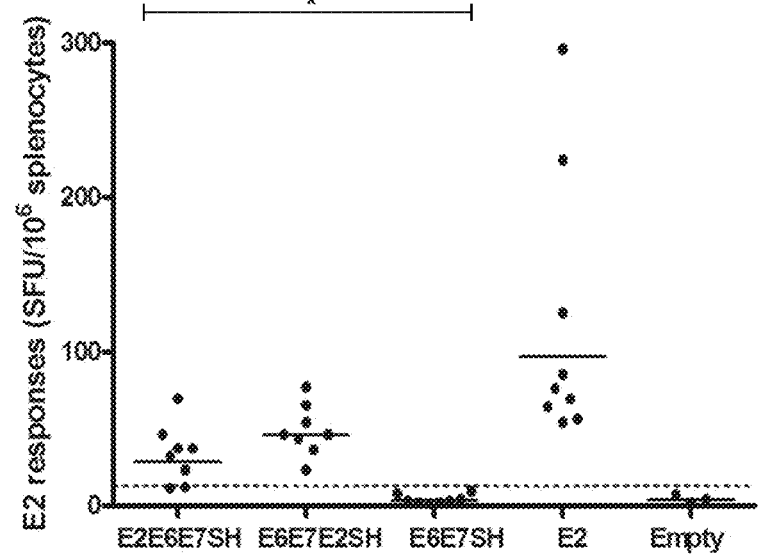
Figure 8:
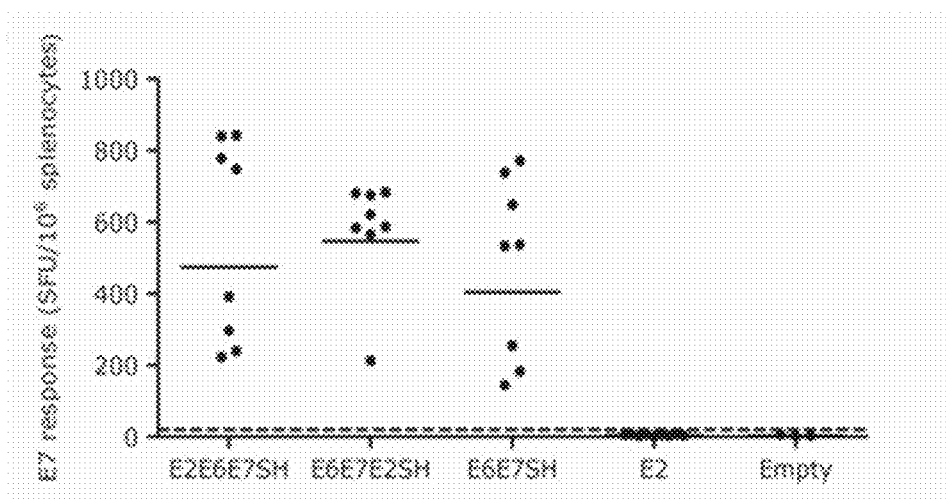
Figure 9:
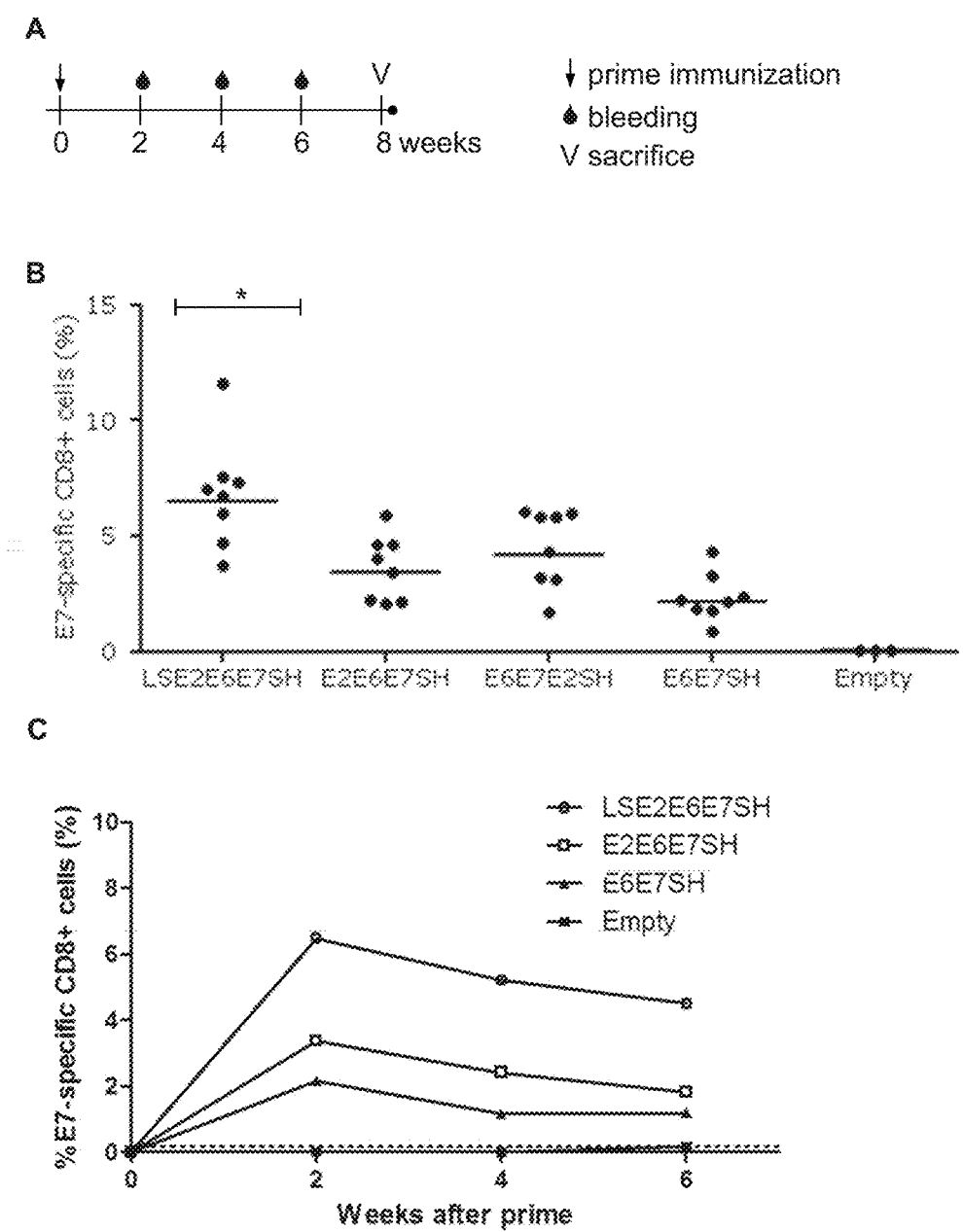
FIG. 9. Sustained HPV16 immune responses in immunized mice. In particular, (A) Immunization scheme. CB6F1 mice were immunized with $1*10^{10}$ vp of Ad35 vectors expressing variants HPV16 LSE2E6E7SH, HPV16 E2E6E7SH, HPV16 E6E7SH, or with an adenovector not expressing a transgene (Emtpy). Blood samples were taken every two weeks to determine the percentage E7-specific CD8+ T-cells by tetramer staining. (B) Immune responses two weeks after immunization. The vector including a leader sequence induced a higher response than vectors without the leader sequence; LSE2E6E7SH vs E2E6E7SH (*: p<0.05). (C) Kinetics of the responses. ANOVA Post-hoc Bonferroni statistical analysis was performed on log transformed data of the week 2 data set. The E7 response induced by molecules including E2 tend to be higher compared to the molecule without E2, though the results were not statistically significant.

Addition of a leader sequence was shown to result in higher E7-specific responses when fused to the N-terminus of the fusion protein of wild type E6 and E7 (FIG. 6C). Similarly, the effect of the leader sequence on immunogenicity of the E2E6E7SH fusion protein was determined. Therefore, Ad35 vectors encoding the HPV16 designer polypeptide, with or without N-terminal E2 and an Ad35 vector encoding LSE2E6E7SH were used for immunization of mice and blood samples were taken at two-week intervals to measure E7-specific immune responses (FIG. 9). As shown in FIGS. 7 and 8 the presence of E2 at either N- or C-terminally fused to E6E7SH tended to increase the immune responses. Addition of the IgE leader sequence further increased the E7-specific response (FIG. 9B). Over time sustained immune responses were observed for all three adenoviral vectors that encoded designer molecules according to the invention, and the highest response after the immunization corresponded with the highest responses over the duration of the experiment.

It is concluded that the responses that are induced by the designer construct that further includes N-terminal E2 can be increased by addition of specific sequences, e.g., the IgE leader sequence, that target the encoded protein to specific cellular compartments.

The cellular immune response against the peptide of the invention can be induced with different types of adenoviral vectors. In the previous experiment we used Ad35 vectors, while in the experiment of FIG. 10, mice were immunized with an Ad26 adenoviral vector expressing HPV16

Figure 10:
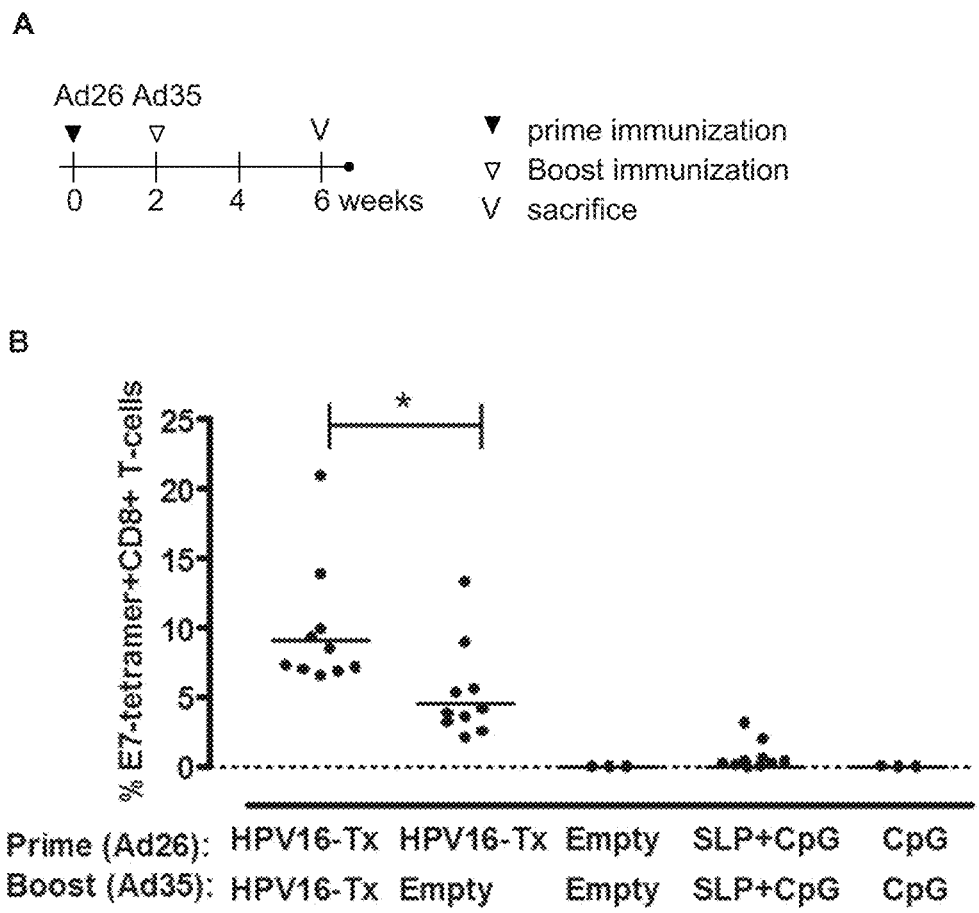
FIG. 10. Use of different Adenoviral vectors to boost immune responses. (A). Immunization scheme. CB6F1 mice were immunized with an Ad26 vector expressing HPV16 E2E6E7SH (HPV16-Tx) or with an Ad26 vector expressing no transgene (empty). Two weeks later the immunizations were repeated with Ad35-based vectors as indicated below the figure. Four weeks after the second immunization the mice were sacrificed and blood samples were used to determine the percentage of E7-specific CD8+ T-cells by tetramer staining (B). * indicates the comparison of Ad26.HPV16-Tx/Ad35.HPV16-Tx versus Ad26.HPV16-Tx/Ad35.Empty, p<0.05 (student t-test on log transformed data, with alpha=0.01 for multiple comparisons).

E2E6E7SH. The data show that also immunization with an Ad26-based vaccine induced E7-specific T-cells. In addition, the results demonstrate that a second immunization with an Ad35 adenoviral vector expressing HPV16 E2E6E7SH further boosted the cellular immune responses (FIG. 10).

Example 4. Immunogenicity of HPV16 Designer Constructs in Rhesus Macaques

Figure 11:
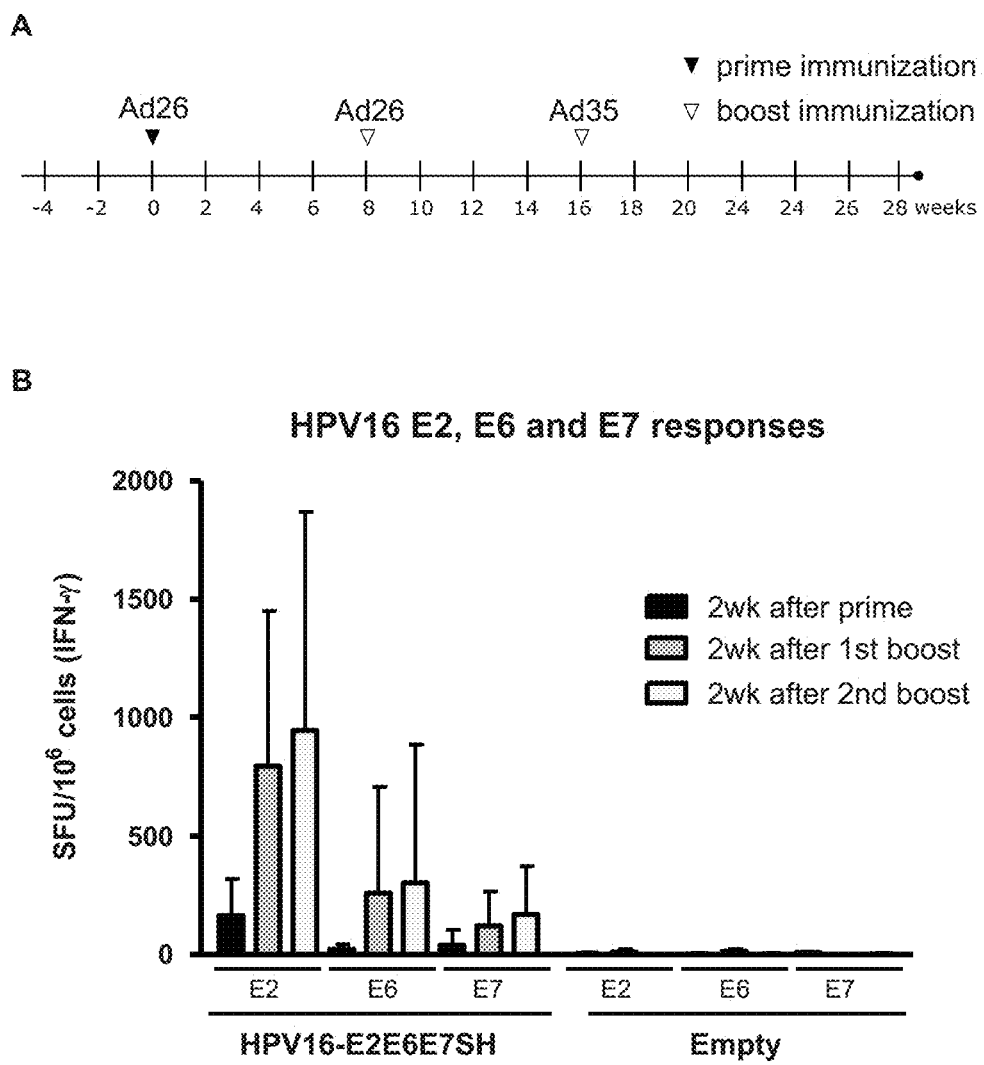
FIG. 11. Cellular immunogenicity of HPV16 E2E6E7SH in Rhesus macaques. (A) Immunization scheme. Rhesus macaques were immunized at day 0: Eight animals received Ad26.HPV16-E2E6E7SH and two control animals received Ad26.Empty by intramuscular immunization (i.m). A boost immunization was given (Ad26.HPV16-E2E6E7SH or Ad26.Empty) at 8 weeks. At 16 weeks, animals received a second boost immunization with Ad35 vectors expressing the same HPV16 E2E6E7SH, while control animals received Ad35.Empty. The dose of adenovectors was $1*10^{11}$vp per immunization. Blood drawings were performed at several time points. (B) Cellular immune responses in PBMCs were measured by IFNγ ELISPOT. PBMCs were stimulated with peptide pools corresponding to HPV16 E2, E6 or E7 and the number of spot-forming units (SFU) in $1*10^6$PBMCs are depicted. The empty control animal (n=2) showed no detectable response. For details see example 4.

To evaluate the ability of the adenoviral vectors expressing the designer sequence of the invention to induce immune responses in non-human primates, rhesus macaques were immunized by intramuscular injection with adenovectors (Ad26) expressing HPV16 E2E6E7SH or adenovectors not encoding a transgene (Empty), with a dose of $1*10^{11}$ vp. Eight weeks after the immunization the immune responses were boosted by immunization with Ad26 vectors expressing the same antigen. At week 16 the animals received one more injection with the Ad35 vectors expressing the same antigen. Blood samples were taken at several time points and isolated white blood cells were stimulated overnight with a peptide pools corresponding to HPV16 E2, E6 or E7. Specific responses were measured by IFNγ ELISPOT. The data are presented in FIG. 11. In addition at week 10 and week 18 post prime immunization, the cellular immune response specific to peptides spanning the novel junctions in the invention was evaluated. The induction of IFNγ response was in all animals below the limit of detection of <50 SFU per $1*10^6$ PBMC (data not shown).

The data show that immunization of non-human primates with Ad26.HPV16-E2E6E7SH resulted in cellular immune responses against all three HPV16 proteins that are present in the encoded transgene, but not against the novel junctions. Responses could be boosted by the additional immunization with Ad26.HPV16-E2E6E7SH and additional boost at week 16 with the corresponding Ad35 vector further increased the HPV16 E2, E6 and E7-specific immune responses.

In a separate experiment (not shown), Rhesus macaques were immunized by intravaginal administration with a combination of two adenoviral vectors, one expressing HPV16 E6E7SH and the other the HPV16 L1 protein. Low but measurable cellular responses were measured in peripheral mononuclear blood cells against both E6 and E7. In these experiments, strong cellular immune responses against L1 were detected.

Example 5. Therapeutic Efficacy in a Mouse Tumor Model

A polypeptide of the invention for HPV16 (comprising SEQ ID NO: 1) is capable of inducing HPV16-specific cellular immune response in animals, which can exert a therapeutic effect on cells expressing HPV16 E6 and/or E7. Therapeutic immunization, i.e. immunization after tumor growth has started, can be used to demonstrate efficacy of a therapeutic HPV vaccine candidate. The therapeutic effect of Ad26 and Ad35 vectors was tested in mice that were injected with TC-1 cells (mouse cells expressing HPV16 E6 and E7) (Lin et al., 1996, Cancer Res 56: 21-6). TC-1 cells will form solid tumor within a few days to weeks after sub-cutaneous injection in mice. Without vaccine the tumors grew rapidly and reach a pre-determined size of 1000 mm³ within 30 days (panels D and E). Upon reaching this size the mice are sacrificed for ethical reasons.

Figure 12:
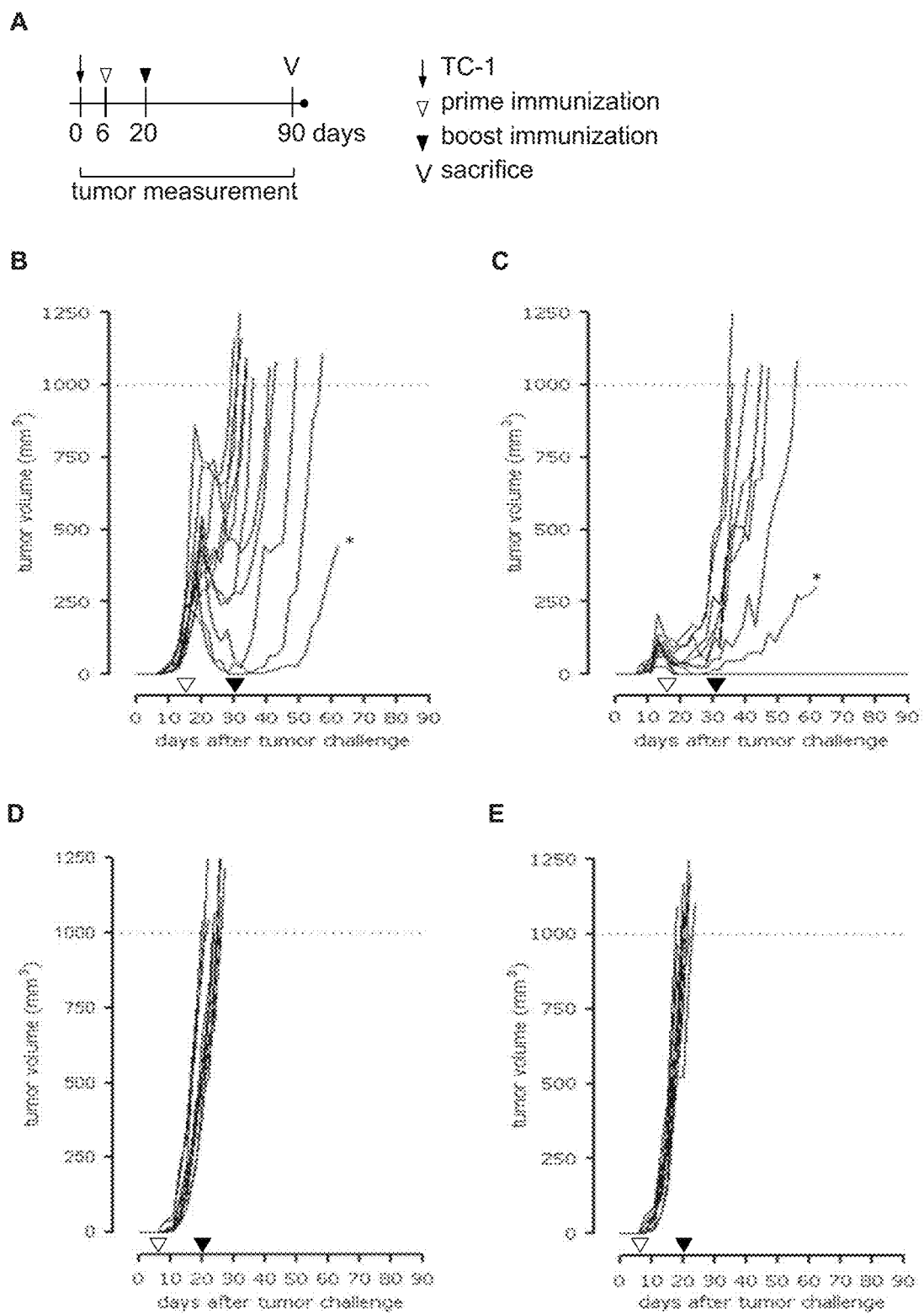
FIG. 12. Therapeutic effect of Adenovectors expressing HPV16-E2E6E7SH. (A) TC-1 injection and immunization scheme. CB6F1 mice were injected sub-cutaneously with $1*10^5$ TC-1 cells at day 0. After six days, when tumors were palpable, mice were immunized with two SLPs covering HPV16 E6 and E7 immunodominant epitopes (i.e., HPV16 E6, aa41-65 (KQQLLRREVYDFAFRDLCIVYRDGN; SEQ ID NO: 18) and HPV16 E7 aa 43-77 (GQAEP-DRAHYNIVTFCCKCDSTLRLCVQSTHVDIR; SEQ ID NO: 19)) at 150 µg in a final volume of 200 µl 0.9% saline supplemented with 5 nmol ODN1826-CpG (B) or Ad26.HPV16-E2E6E7SH (C). Control mice received either CpG alone (D) or Ad26.Empty (E). All mice received a boost immunization at day 20. Mice that received Ad26 vectors in the prime immunization were subsequently immunized with the corresponding Ad35 vectors. The other mice received, SLP adjuvanted with CpG or CpG alone as in the prime immunizations. (B-E) Tumor measurement in TC-1 injected mice. Tumor volume was calculated as (width$^2$*length)/2. Mice were sacrificed when tumor volumes surpassed 1000 mm$^3$. Two mice had to be sacrificed due to weight loss of more than 20% (indicated with asterisks). (F-G) Close up of panels B and C for first 35 days. (H) Survival after TC-1 injection. The survival of mice treated with Ad.HPV16-E2E6E7SH was significantly increased compared with mice immunized with SLP and CpG (Log-rank test p<0.05). Three mice immunized with the Ad.HPV16-E2E6E7SH were tumor free at the end of the experiment (at day 92).

With a prime-boost immunization scheme with SLPs (used as a positive control; Kenter et al., 2009, N Engl J Med 361:1838-47; Zwaveling et al., 2002, J Immunol 169:350-8) or adenoviral vectors expressing HPV16-E2E6E7SH, a marked decrease of the growth of TC-1 induced tumors was observed (FIG. 12, panels B and C). Closer inspection of the first 30 days after the prime immunizations (Panels F and G) shows that the immunization with the adenovectors expressing E2E6E7SH have a substantially larger impact on tumor growth than immunization with the SLPs. The initial growth rate is much lower and in most cases the tumors shrunk. In 3 out of 11 mice immunized with the adenoviral vectors, the tumors were completely eradicated, which is reflected in the survival plot (panel H).

In conclusion, immunization with adenoviral vectors expressing an HPV16 designer polypeptide of the invention significantly reduced tumor growth or completely eradicated established tumors in a well-established challenge model for HPV16-induced cancer.

Example 6: Employment of Repressor Systems to Improve the Productivity and Genetic Stability of Adenoviral Vectors Expressing HPV-Derived Antigens It has previously been reported that transgenes inserted into adenovirus vectors under the control of powerful constitutively active promoters can, depending on the properties of the transgene product, negatively impact vector production (Yoshida & Yamada, 1997, Biochem Biophys Res Commun 230:426-30; Rubinchik et al., 2000, Gene Ther 7:875-85; Matthews et al., 1999, J Gen Virol 80:345-53; Edholm et al., 2001, J Virol 75:9579-84; Gall et al., 2007, Mol Biotechnol 35:263-73). Examples of transgene-dependent vector productivity issues include inefficient vector rescue and growth, low final vector yields, and, in severe cases, rapid outgrowth of viral mutants with defective transgene cassettes. To solve these issues, multiple studies explored the possibility to silence vector transgene expression during vector replication in producer cells (Matthews et al., 1999, J Gen Virol 80:345-53; Edholm et al., 2001, J Virol 75:9579-84; Gall et al., 2007, Mol Biotechnol 35:263-73; Cottingham et al., 2012, Biotechnol Bioeng 109:719-28; Gilbert et al., 2014, J Virol Methods 208:177-88). In this regard, different repression systems have previously been implemented in the context of Ad vectors and have indeed shown to improve vector productivity and genetic stability for vectors encoding different types of (inhibitory) transgenes.

It was observed that some of the adenovirus vectors described herein, as well as some other adenoviral vectors encoding certain HPV antigen variants, displayed some of the transgene-dependent vector productivity issues described above, and therefore could possibly be further improved in that respect. We therefore sought to investigate whether usage of systems to repress vector transgene expression can improve production characteristics of Ad vectors expressing HPV-derived antigens as those described herein. For this purpose, we implemented two existing repressor-operator systems, i.e. TetR/TetO (Yao & Eriksson, 1999, Hum Gene Ther 10:419-22, EP0990041B1) and CymR/CuO (Mullick et al., 2006, BMC Biotechnol 6:43), into our adenovirus vector platform. Both the TetR/TetO and the CymR/CuO system have previously been used by others to improve adenovirus vector productivity through vector transgene silencing during vector replication (Gall et al., 2007, Mol Biotechnol 35:263-73; Cottingham et al., 2012, Biotechnol Bioeng 109:719-28; Gilbert et al., 2014, J Virol Methods 208:177-88). Implementation of these two systems involved the generation of adenoviral vectors expressing genes of interest under the control of either a TetO or a CuO sequence-containing CMV promoter. Furthermore, the implementation entailed the generation of cell lines stably expressing the respective cognate repressors proteins (i.e. TetR or CymR).

Several E1-deleted, Ad26- and Ad35-based vectors were generated in which sequences encoding heterologous polypeptides were operably linked to a CMV promoter containing either TetO or CuO operator sequences. First, certain TetO- or CuO-containing sequences (SEQ ID NO: 11 and SEQ ID NO: 12, respectively) were inserted near the transcription start site (TSS) of the CMV promoter (SEQ ID NO: 13) of pAdapt26 and pAdapt35.Bsu plasmids (Abbink et al., 2007, *J Virol* 81:4654-63; Havenga et al., 2006, *J Gen Virol* 87:2135-43). The operator-containing sequences were inserted at precisely the same positions of the CMV promoter as previously described for the two systems (Yao & Eriksson, 1999, *Human Gene Ther* 10:419-22; EP0990041B1: Mullick et al., 2006, *BMC Biotechnol* 6:43; EP1385946B1). Specifically, relative to the TSS (as originally assigned; Stenberg et al. 1984, *J Virol* 49:190-9), the TetO- and CuO-containing sequences were inserted directly downstream of positions −20 and +7, respectively. In SEQ ID NO: 13, these two positions correspond to positions 716 and 742, respectively. The resulting operator-containing CMV promoters are termed, respectively, CMVTetO and CMVCuO. Next, different transgenes were inserted downstream of the (modified) CMV promoters of the resulting constructs using HindIII and XbaI restriction sites. These transgenes included genes encoding a fusion protein of green fluorescent protein and luciferase (GFP-Luc), HPV16 LSE2E6E7SH as described above in example 1, and another polypeptide with some similarity to HPV16 LSE2E6E7SH (a construct referred to in this example as 'HPVAg'). HPVAg comprises the same leader sequence as present in LSE2E6E7SH, as well as E2, E6, and E7 sequences of HPV16. Using methods as described herein, the resulting modified pAdapt26 and pAdapt35.Bsu plasmids were used for the generation of adenoviral vectors expressing the above mentioned reporter and HPV transgenes under the control of either the CMVTetO or the CMVCuO promoter.

Cell lines expressing either TetR or CymR were generated by stable transfection of PER.C6® cells using, respectively, plasmid pcDNA™6/TR (LifeTechnologies, V1025-20) and a derivative of pcDNA™6/TR in which the TetR-coding sequence (SEQ ID NO: 14, which encodes polypeptide SEQ ID NO: 15) is replaced by a codon-optimized CymR-coding sequence (SEQ ID NO: 16, which encodes polypeptide SEQ ID NO: 17). Stable cell line generation was performed largely as described by the supplier of pcDNA™6/TR using a transient transfection-based assay to screen for cell clones capable of repressing expression of CMVTetO- or CMVCuO-driven genes. The resulting PER.C6/TetR and PER.C6/CymR cell lines were analyzed for their ability to repress transgene expression during vector replication in these cells. Experiments conducted with vectors expressing GFP-Luc under the control of operator-containing CMV-promoters showed at least a 10-fold reduction of luciferase gene expression throughout the complete virus replication cycle in the cell lines expressing the repressor corresponding to the respective operator sequences (data not shown). This confirmed that the PER.C6/TetR and PER.C6/CymR cell lines were capable of repressing vector transgene expression in the context of replicating adenovirus vectors.

Figure 13:
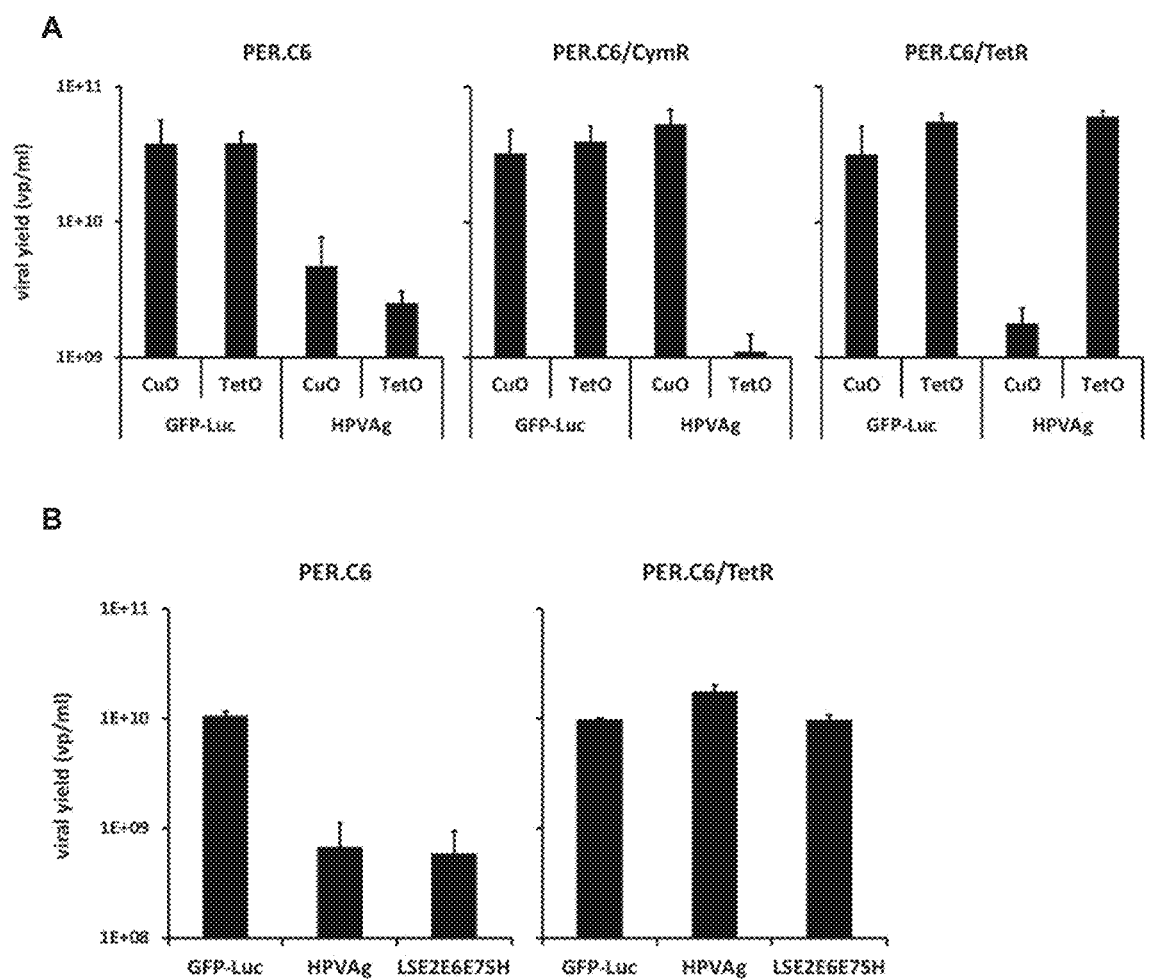
FIG. 13. Adenoviral vectors carrying transgenes encoding either HPVAg or LSE2E6E7SH show increased viral yields on cells capable of repressing transgene expression. A) Viral yield assay for Ad35 vectors. PER.C6, PER.C6/CymR, and PER.C6/TetR cells were infected by Ad35 vectors carrying GFP-Luc- or HPVAg-encoding transgenes. These transgenes were driven by either CuO- or TetO-containing CMV promoters. Viral yields were determined four days after infection by an Ad35 hexon-specific qPCR-based method. B) Viral yield assay for Ad26 vectors. PER.C6 and PER.C6/TetR cells were infected by Ad26 vectors carrying GFP-Luc, HPVAg, or LSE2E6E7SH-encoding transgenes, which were all driven by a TetO-containing CMV promoter. Viral yields were determined three days after infection by an Ad26 hexon-specific qPCR-based method. For details see Example 6.

The effect of TetR- and CymR-mediated repression of adenovector transgene expression on vector yields was investigated for Ad35-based vectors expressing HPVAg (FIG. 13A). To this end, PER.C6, PER.C6/TetR, and PER.C6/CymR cell lines, seeded at $3*10^5$ cells per well in 24-well plate wells, were subjected to quadruplicate infections—at 1000 virus particles per cell and for a duration of three hours—by vectors expressing HPVAg from either CMVTetO or CMVCuO promoters. As controls, parallel infections were performed with corresponding vectors expressing GFP-Luc instead of HPVAg. Four days after infection, crude viral lysates were prepared by subjecting the contents of the wells (i.e. infected cells and medium) to two freeze-thaw cycles. Adenovector titers were subsequently determined by an Ad35 hexon sequence-specific quantitative PCR-based protocol that uses a purified Ad35 vector with known virus particle titer as a standard. The results show that both the TetO- and the CuO-containing HPVAg-encoding Ad35 vectors, compared to the control vectors expressing GFP-Luc, display decreased vector yields on normal PER.C6 cells. By contrast, when produced on cells expressing their cognate repressors (i.e. TetR and CymR, respectively), these same vectors gave yields as high as those obtained with the control vectors. These data indicate that repression of transgene expression during vector production in producer cells can be beneficial for the productivity of Ad35 vectors carrying HPVAg as a transgene.

The effect that repression of adenovector transgene expression may have on vector yields was also investigated for vectors derived from adenovirus serotype 26 (Ad26) (FIG. 13B). In an assay performed essentially as described above for the Ad35 vectors, Ad26 vectors carrying CMVTetO promoter-controlled transgenes encoding either GFP-Luc, HPVAg, or LSE2E6E7SH were used to infect PER.C6 and PER.C6/TetR cells at 1500 virus particles per cell. Three days later the infections were harvested and virus particle titers determined by an Ad26 hexon sequence-specific quantitative PCR-based method. The results show that on PER.C6 cells the yields for the vectors encoding HPVAg and LSE2E6E7SH are lower than obtained with the control vector encoding GFP-Luc. In contrast, on PER.C6/TetR cells, both these vectors showed titers that are as high as that obtained for the control vector. Together with the results above (for Ad35 vectors), these data indicate that repression of transgene expression during adenovector production increases the yields of vectors expressing HPVAg and LSE2E6E7SH.

We have observed major issues regarding the genetic stability of an adenovirus vector that carried a CMV promoter-driven transgene for HPVAg. For example, it was observed that after several passaging rounds of this vector on PER.C6 the majority of the vector population consisted of a mutant vector that carried a large deletion in the HPVAg coding sequence (data not shown).

Figure 14:
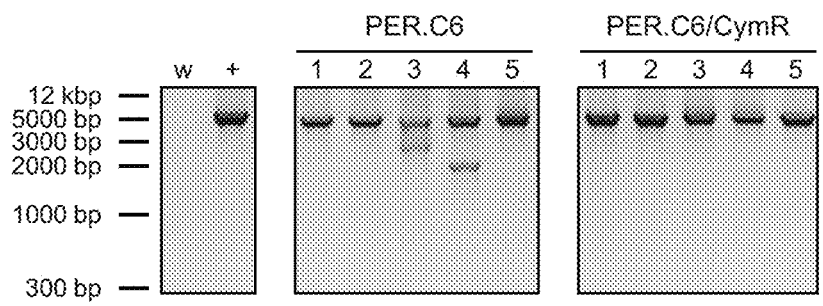
FIG. 14. Employment of a repressor system to repress transgene expression during vector production prevents transgene cassette instability in an adenoviral vector carrying an HPVAg-encoding transgene. An Ad35 vector expressing HPVAg under the control of CMVCuO was rescued by DNA transfection on either PER.C6 or PER.C6/CymR cell lines. Resultant viral plaques were picked—five per cell line—and used for consecutive infection rounds on the respective cell lines. A) Analysis of the integrity of the vector transgene cassette region by PCR after 10 viral passages. PCR products obtained from viral isolates passaged on PER.C6 and PER.C6/CymR are shown in the middle and right panels, respectively. The full-length-appearing PCR products obtained for PER.C6-passaged viral isolates 1, 2, 4, and 5, and those seen for PER.C6/CymR-passaged isolates 1 to 5 were analyzed by Sanger DNA sequencing. Analysis of the chromatogram traces (not shown) revealed that all isolates grown on PER.C6, but not those grown on PER.C6/CymR, contained either frameshifting small deletions or premature stop mutations within the coding sequence for HPVAg. B) Analysis of the ability of the vectors to express HPVAg after seven viral passages. A549 cells were transduced by the PER.C6- and PER.C6/CymR-grown viral isolates and HPVAg expression was analyzed by Western Blot using an HPV16 E7-specific antibody. The predicted size for HPVAg is 83 kDa. For details see Example 6.
Figure 14:
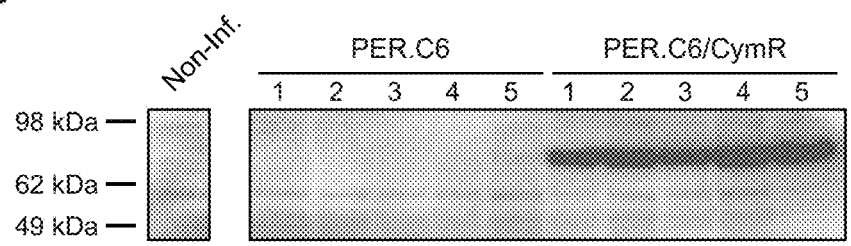

We reasoned that employment of a transgene expression repression system, such as one of the two described above, could prevent genetic stability issues associated with transgenes, such as HPVAg that are inhibitory to vector growth. To test this, an Ad35-based vector with CMVCuO promoter-driven HPVAg expression was assessed for transgene cassette stability upon growth of the vector on either PER.C6 or PER.C6/CymR cells (FIG. 14). In brief, vector DNA was transfected into the two different cell lines and resultant viral plaques were allowed to grow under an agarose layer. From each of the two transfections, five viral plaques were isolated and separately passaged further on the same cell line (i.e. as used for the transfection), for ten consecutive viral passages. Transgene integrity was assessed by PCR amplification of the transgene cassette at viral passage number ten (VPN10), and the subsequent analysis of resultant PCR products by gel electrophoresis and Sanger sequencing. In addition, at VPN7, the passaged viral clones were assessed for their ability to express HPVAg. This was done by using the passaged viral isolates to infect A549 cells at 1000 virus particles per cell, lysing the cells at 48 hours post infection, and subsequently analyzing the expression of HPVAg by western blotting using a monoclonal antibody directed against HPV16 E7 (Santa-Cruz Biotechnology). The results of the gel electrophoresis and sequencing analyses showed that all five viral isolates that had been passaged on PER.C6 each carried either small frameshifting deletions or premature stop mutations within the transgene cassette. By contrast, such deletions or mutations could not be detected in any of the vector isolates that had been passaged on the cell line expressing CymR (PER.C6/CymR). In agreement with these data, all PER.C6/CymR-propagated vector isolates were able to express HPVAg, while all PER.C6-grown vectors completely lost this ability, suggesting defective transgene cassettes for these vectors. In conclusion, our data demonstrate that employment of a repressor system, as for instance the CymR/CuO system, to repress vector transgene expression during vector propagation is an effective means to prevent severe transgene cassette instability, such as that seen for vectors carrying a transgene expressing HPVAg.

Example 7: Construction of a Designer Polypeptide Comprising Essentially all HPV18 E6 and E7 CTL Epitopes Similar to our design for HPV16 E6 and E7, we designed a novel, non-tumorigenic polypeptide (and nucleic acid encoding such) that contains essentially all CTL epitopes of HPV18 E6 and E7 proteins, and has a minimum number of anticipated/predicted strong neo-epitopes (neo-epitopes meaning epitopes not present in the wild type HPV18 E6 and E7 proteins). A polypeptide of the invention for HPV18 (also sometimes referred to as HPV18 'E6E7SH' herein) comprises the amino acid sequence as provided in SEQ ID NO: 20. A codon-optimized nucleic acid encoding this polypeptide is provided in SEQ ID NO: 21.

The molecules of the invention for HPV18 have the same advantages as described under example 1 for HPV16. They are single molecules, which provides manufacturing advantages over strategies where multiple molecules are used. In addition, a polypeptide of the invention comprises essentially all putative CTL epitopes that are present in wild-type E6 and E7 of HPV18, and at the same time have a minimum number of anticipated/predicted strong neo-epitopes that could potentially be immunodominant and thus divert the immune response from relevant wild-type CTL epitopes. Thus the constructs of the present invention are immunologically more favourable than molecules described by others that either lack possible CTL epitopes and/or that contain more or stronger neo-epitopes.

For instance, the HPV18 designer construct of SEQ ID NO: 20 contains only five neo-epitopes with a length of nine amino acids with a predicted binding affinity <50 nM for the 20 most common HLA-A, 20 most common HLA-B and 20 most common HLA-C alleles, as described in example 1 for the HPV16 designer construct (having SEQ ID NO: 1).

Nucleic acid encoding our thus designed HPV18 E6E7SH molecule (i.e. a polypeptide having amino acid sequence as provided in SEQ ID NO:20) was synthesized, the nucleic acid sequence comprising SEQ ID NO: 21, and flanked by a HindIII site and a Kozak sequence on the 5'end and an XbaI site on the 3' site (custom synthesis and standard molecular cloning at Invitrogen Life technologies, Germany).

The synthezised fragments were cloned using HindIII and XbaI into a standard expression vector, pCDNA2004.Neo, harbouring both a bacterial resistance marker (Ampiciline) and a mammalian resistance marker (Neomycine), to obtain plasmid vectors encoding an HPV18 designer molecule of the invention, e.g. for (transient) transfection based experiments.

These molecules could be used as such, but also as the basis for further molecules that contain additional features. As non-limiting examples, some further variants were prepared as described below.

The HPV18 E6E7SH fusion protein sequence can be combined with sequences of other HPV18 early proteins to target individuals with persistent infection and to broaden the immune repertoire in an immunized individual. As a non-limiting example of such embodiments, we prepared a sequence coding for a fusion protein of E6E7SH with E2 at its N-terminus. We mutated Glycine at position 294, Lysine at position 300 and Cysteine at position 301 of the wt HPV18 E2 protein (Genbank: AAP20597.1) into respectively Valine, Methionine and Arginine to abrogate DNA binding activity. Each of these mutations on its own already completely abrogates the binding of E2 to DNA sequences that harbour E2 binding domains (Prakash et al., 1992, *Genes Dev* 6: 105-16).

The resulting polypeptide is referred to as HPV18 E2E6E7SH and comprises SEQ ID NO: 22. A codon-optimized sequence encoding this polypeptide was prepared and is provided in SEQ ID NO: 23.

Figure 15:
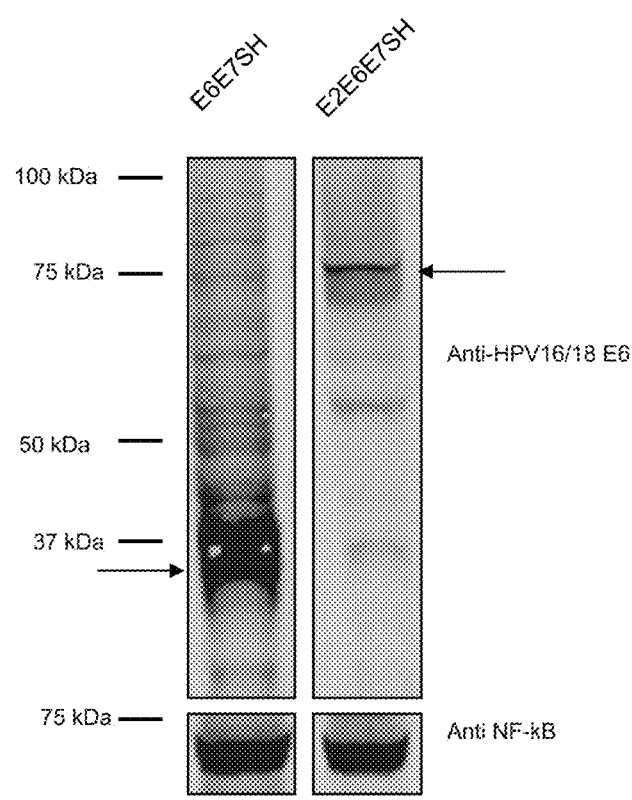
FIG. 15. Expression of fusion proteins of HPV18 E6 and E7. HEK-293T cells were transiently transfected with DNA vectors expressing the transgenes indicated above the figure. 24 hr after transfection the cells were harvested and cell extracts were analyzed by SDS-PAGE and western blotting with an antibody against HPV18 E6 (upper panel). A loading control showing NF-kB (lower panel) confirms similar loading of cell lysates in both lanes. A molecular weight marker is indicated on the left and arrows indicate the fusion proteins. Expected sizes: E6E7SH approx. 38 kDa; E2E6E7SH approx. 75 kDa.

The sequences that encode the HPV18 E6E7SH polypeptides of the invention, with or without E2, can for instance be expressed from DNA constructs, from RNA or from viral vectors. FIG. 15 demonstrates expression in HEK-293T cells upon transient transfection with DNA vectors expressing transgenes as described above. After transfection, cells were harvested and cell extracts were analyzed by SDS-PAGE and western blotting with an antibody that recognizes E6 of HPV18. This experiment demonstrates expression of the expected fusion proteins of appropriate size upon transfection of the expression vectors.

Adenoviral vectors can be used to express the E6E7, either with or without E2, and with or without additional sequences to augment the immunogenicity of the encoded fusion protein.

The genes, coding for HPV18 designer sequences described above were gene optimized for human expression and synthesized, at Geneart. A Kozak sequence (5' GCCACC 3') was included directly in front of the ATG start codon, and two stop codons (5' TGA TAA 3') were added at the end of the respective coding sequence. The genes were inserted in the pAdApt35BSU plasmid and in the pAdApt26 plasmid (Havenga et al., 2006, *J Gen Virol* 87, 2135-43) via HindIII and XbaI sites.

Ad35.HPV18-E6E7SH is a recombinant adenovirus serotype 35 (Ad35) vector comprising the codon-optimized nucleotide sequences for the expression of the HPV18 designer fusion protein variant as described above (HPV18 E6E7SH, having the amino acid sequence provided in SEQ ID NO: 20). The combined E6 and E7 sequences were placed under the control of a CMV promoter in the E1 region of the E1,E3 deleted adenovirus genome. Ad26.HPV18-E6E7SH is the equivalent vector based on recombinant adenovirus serotype 26.

Similarly, Ad26 and Ad35-based recombinant adenoviral vectors were produced that encode the HPV18 E2E6E7SH (SEQ ID NO: 22) variant.

All adenoviruses were generated, prepared, purified and stored as described in example 1 above.

Example 8. Lack of Transforming Activity of the HPV18 Designer Constructs

The E6 and E7 proteins of HPV18 have tumorigenic potential, which is apparent as transforming activity in certain assays, such as colony formation in a soft-agar assay (Massimi and Banks, 2005, *Methods Mol Med* 119: 381-395). The E6E7SH polypeptide as described in example 7 comprises the fragments of the E6 and E7 proteins in a re-ordered fashion. This is expected to remove the tumorigenic potential, as can be measured for instance by lack of transforming activity as compared to either of wt E6 and E7 proteins in such assays.

Others reported that gene-shuffled variants of HPV16 E6 and E7 have indeed lost their oncogenic potential (Öhlschläger et al., 2006, *Vaccine* 24: 2880-93; Henken et al., 2012, *Vaccine* 30: 4259-66), demonstrating that gene shuffling destroys the wild-type functions of HPV16 E6 and E7 proteins. In example 2, we have shown that our designer construct for HPV16 has lost its E6 and E7 activities.

Figure 16:
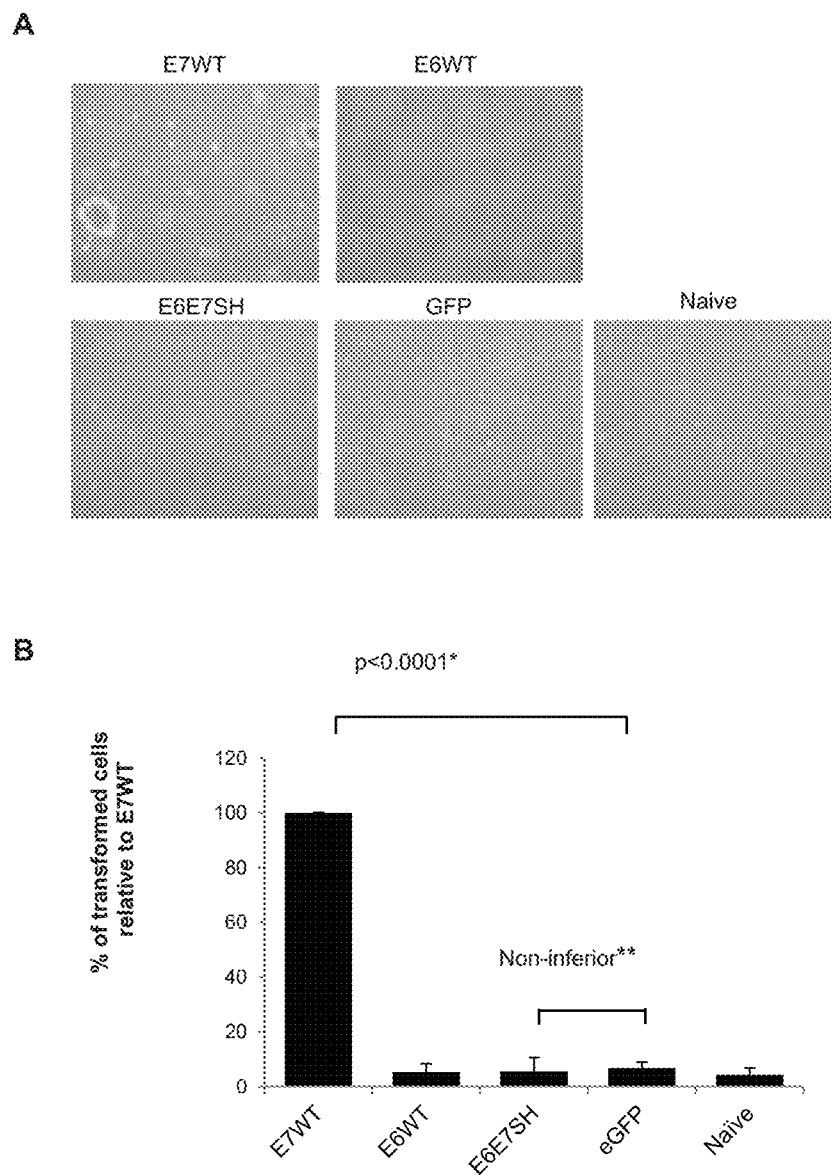
FIG. 16. No colony formation in soft agar by the HPV18 E6E7SH designer construct. A) Representative microscopic images at 40× magnification of the cells in agar six weeks post seeding. Large colonies are observed in the E7 wt transfected cells. B) Colony quantification six weeks post seeding in agar using the Gelcount™ and associated software. *: $p<0.05$ (Poisson regression model); **: non-inferior (generalized linear model with non-inferiority margin of 5%).

To assess the loss of tumorigenic properties, we assessed the ability of our HPV18 E6E7SH construct to confer the ability to grow in soft agar upon NIH 3T3 cells (as described by e.g. Massimi and Banks, 2005, *Methods Mol Med* 119: 381-395). Transfection of NIH3T3 cells with a plasmid expressing the wild type HPV18 E7 resulted consistently in colony formation. Similar to the results obtained with HPV16 E6, expression of wild type HPV18 E6 alone did not cause colony formation above background. Transfection with our HPV18 E6E7SH construct did not lead to growth of colonies of cells in soft agar (FIG. 16) in four independent experiments, demonstrating that nucleic acids encoding a polypeptide of the invention, HPV18 E6E7SH, have lost the transforming capacity that is associated with E7.

Figure 17:
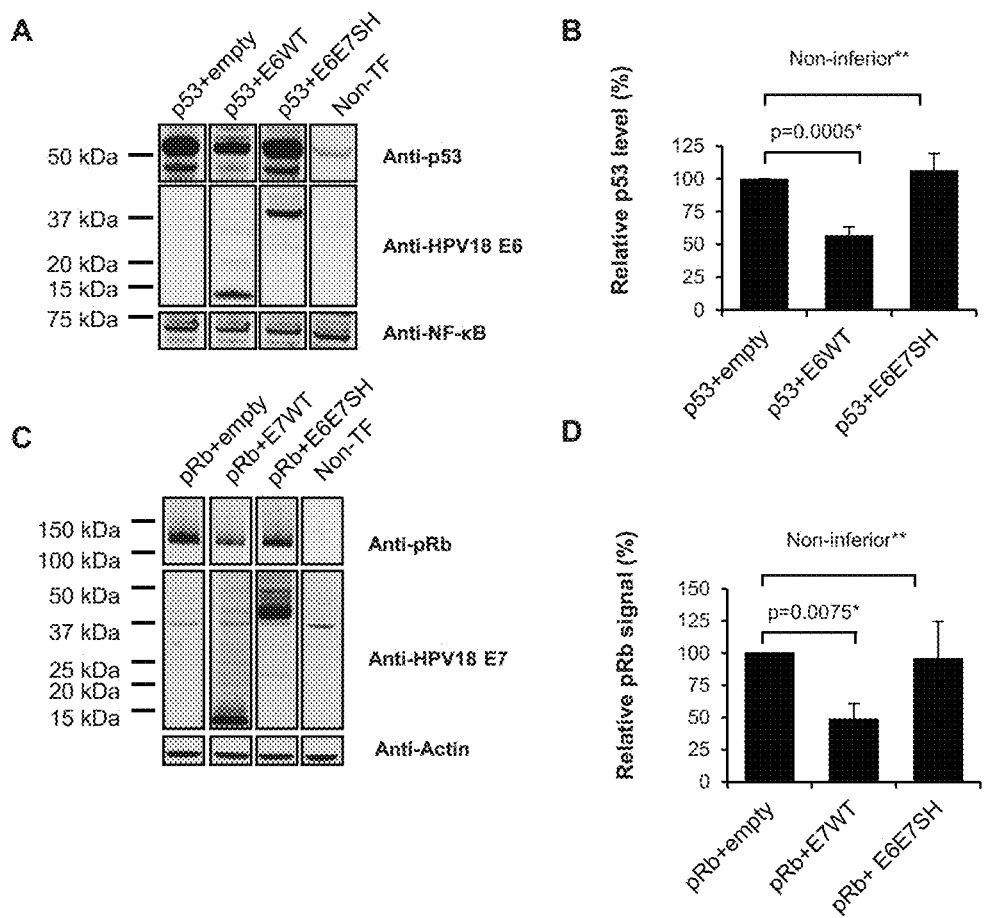
FIG. 17. HPV18 E6E7SH has lost the ability to degrade p53 and pRb. (A) Representative western blot demonstrating absence of p53 degradation by HPV18 E6E7SH. Human p53 null NCI-H1299 cells were co-transfected with a plasmid expressing p53 in combination with a plasmid expressing HPV18 E6 wild-type, E6E7SH or the empty vector. Non-TF indicates non-transfected cells. 24 hours after transfection cell lysates were prepared and 30 μg of total protein was loaded on gel. Upper panel—p53 staining, middle panel—E6 staining, lower panel—NF-kB staining (loading control). (B) Quantification of p53 levels in four independent assays. The p53 signal was normalized to the NF-κB signal. C) Western blot demonstrating lack of pRb degradation by HPV18 E6E7SH. pRb null Saos-2 cells were transfected with a plasmid expressing pRb in combination with a plasmid expressing HPV18 E7 wild-type, E6E7SH or the empty vector. Non-TF indicates non-transfected cells. 24 hours after transfection cell lysates were prepared and 10 μg of total protein was loaded on gel. Upper panel—pRb staining, middle panel—E7 staining, lower panel—NF-κB staining (loading control). D) Quantification of pRb levels in four independent assays. The pRb signal was normalized to the NF-κB signal. *: $p<0.05$ (ANOVA models); **: non-inferior (testing was based on 95% CI's derived from ANOVA models. Non-inferiority margin was set at 75%).

The tumorigenic potential of E6 and E7 is associated with their ability to reduce the levels of the cellular proteins p53 and pRb respectively. p53 and pRb degradation assays were performed to demonstrate that nucleic acid encoding a polypeptide of the invention, HPV18 E6E7SH, does not have the biological activity associated with the wild-type E6 and E7 at the molecular level. In short, HPV18 E6 wt and our HPV18 E6E7SH construct were expressed in NCI-H1299 cells that lack endogenous p53 for the p53 degradation assay. For the pRb degradation assay HPV18 E7 wt and the HPV18 E6E7SH construct were expressed in pRb null Saos-2 cells. As can be seen in FIG. 17, co-expression of p53 with HPV18 E6 wt, but not with HPV18 E6E7SH, leads to reduced p53 levels (panels A and B). Likewise, panels 17C,D show that co-expression of pRb with HPV18 E7 wt, but not with HPV18 E6E7SH, leads to reduced pRB levels. These data demonstrate that nucleic acid encoding an HPV18 designer polypeptide of the invention has no ability to form colonies in soft agar and does not contain main biological activities of the wild-type HPV18 E6 and E7 polypeptides, namely the inactivation of p53 and pRb respectively.

Figure 18:
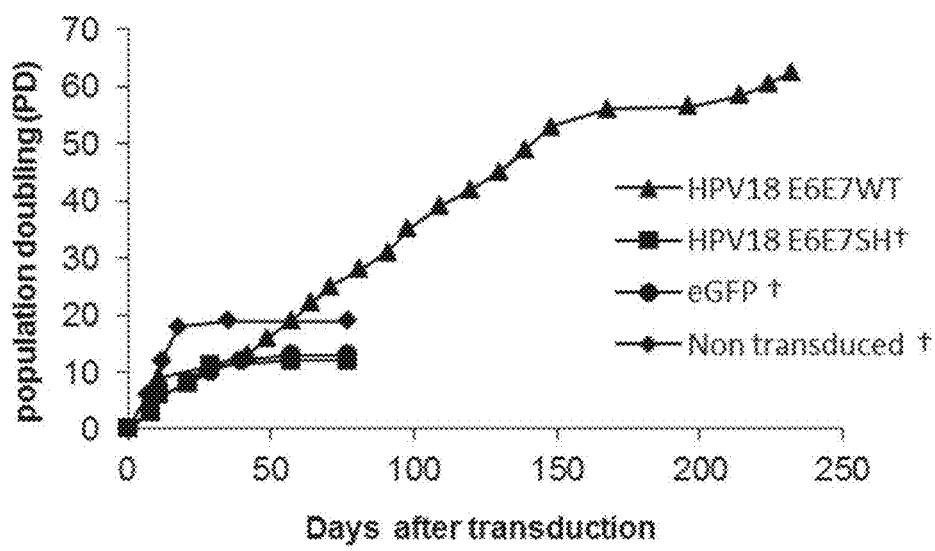
FIG. 18. HPV18 E6E7SH does not immortalize primary human genital keratinocytes. Primary human genital keratinocytes were transduced with lentiviruses encoding either the wild-type E6- and E7-encoding open reading frame of HPV18 (E6E7 wt), the E6E7SH sequence or eGFP. Non-transduced donor cells were used as a control. Only expression of HPV18 E6E7 wt induces immortalization of primary keratinocytes as indicated by the extended lifespan (and hTERT activation around day 200, data not shown). The cross symbol indicates that the cells died in senescence and could not be further cultured. For details see example 8. Similar results were obtained in two additional donors (data not shown).

To further demonstrate the safety of nucleic acid constructs encoding polypeptide of the invention, we made use of primary human genital keratinocytes derived from neonatal foreskin (HEKn cells) that closely resemble the natural target cells for HPV mediated transformation. Immortalization of primary human keratinocytes requires the action of both E6 and E7 wild-type (Munger et al., 1989, *J Virol* 63: 4417-21). This assay is probably the physiologically most relevant in vitro assay to demonstrate the safety of our constructs (Massimi and Banks, 2005, *Methods Mol Med* 119: 381-395). Cells transduced with lentiviruses expressing wild type E6 and E7 from HPV18 (E6E7 wt) induce immortalization in primary keratinocytes as indicated by the extension of their lifespan as compared to non-transduced control cells (FIG. 18) and activation of hTERT, the catalytic subunit of telomerase (data not shown). Expression of the HPV18 designer polypeptide of the invention (HPV18 E6E7SH) is not able to to extend the lifespan compared to GFP-transduced or non-transduced keratinocytes. A similar result was obtained in two additional independent donors (data not shown). Taken together these data demonstrate that our constructs have lost the ability to induce immortalization in primary human keratinocytes, that are considered a highly physiological model.

Another construct wherein comparable fragments of HPV18 E6 and E7 were recombined in a different order was also incapable of immortalization of primary human foreskin keratinocytes. However, and similar to the results with an alternative E6E7 sequence for HPV16 (See example 2), an expanded life span was observed for that alternative HPV18 construct. This indicates some unpredictability in this field, and demonstrates the superiority of the selected designer molecules according to the invention in this safety-related aspect.

All together the experiments in this example provide strong evidence of the lack of transforming activity of nucleic acids encoding polypeptides according to the invention, and thus a strongly improved safety over HPV18 E6 and E7 wt constructs.

Example 9. Immune Responses to the HPV18 E6E7SH Designer Constructs

We have prepared DNA vectors and adenoviral vectors, as described in example 7. To evaluate the vaccine induced immunogenicity, CB6F1 mice were immunized with adenovectors (Ad35) expressing HPV18 E6E7SH or E2E6E7SH, or with adenovectors not encoding a transgene (Empty) as controls. Two weeks after the prime immunization the mice were sacrificed and isolated splenocytes were stimulated overnight with an HPV18 E6 15mer peptide pool. E6-specific immune responses were analyzed by intracellular cytokine staining. In a separate experiment, CB6F1 mice were immunized with adenovectors (Ad35 or Ad26) expressing HPV18 E2E6E7SH or with adenovectors not encoding a transgene (Empty) as control.

Figure 19:
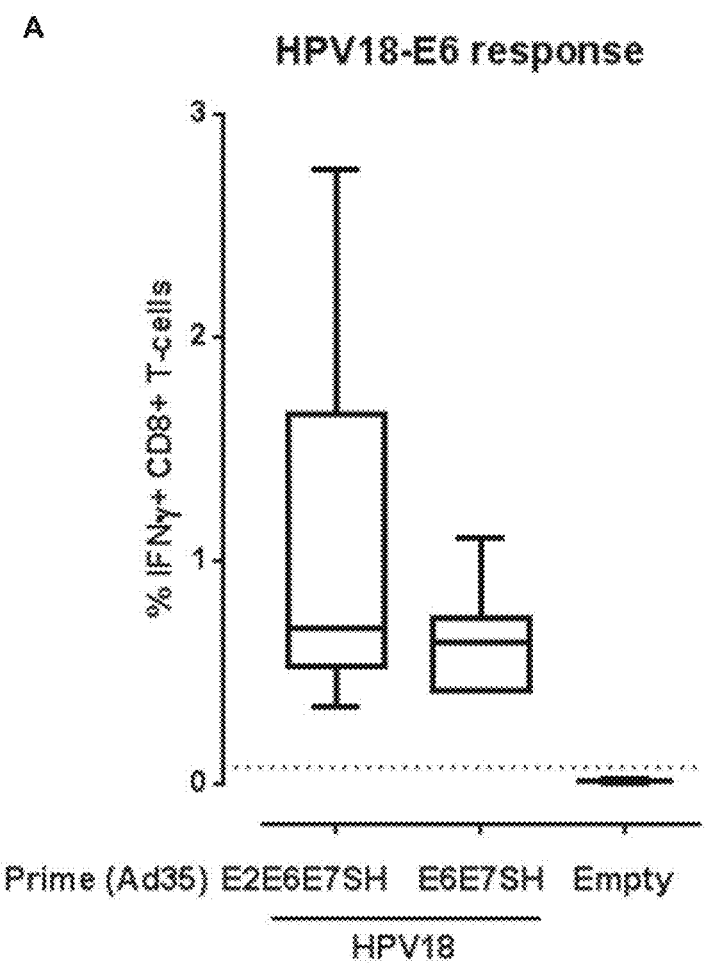
FIG. 19. Immunogenicity of HPV18 E6E7SH variants—Intracellular Cytokine staining. CB6F1 mice were immunized with adenovectors expressing the transgenes indicated below the panels. Two weeks after immunization the mice were sacrificed and isolated splenocytes were stimulated overnight with 15mer peptide pools corresponding to HPV18 E6. Responses are given as percentage of IFNγ-positive CD8+ T-cells.

FIG. 19A shows that immunization of mice with Ad35.HPV18-E6E7SH induces E6-specific immune responses as measured by ICS analysis. In addition, the results in FIG. 19A demonstrate that fusion of E2 to the N-terminus of the designer construct does not decrease the immunogenicity, despite the lower expression of this E2E6E7 variant that was observed upon transfection (FIG. 15). FIG. 19B shows that immunization of mice with Ad35.HPV18-E6E7SH or Ad26.HPV18-E2E6E7SH induces comparable percentage of IFNγ-producing HPV18-E6 specific CD8 T-cells.

The cellular immune response against the peptide of the invention can be induced with different types of adenoviral vectors. In the experiment presented in FIG. 19B, mice were immunized with either Ad26 or Ad35 adenoviral vectors expressing HPV18 E2E6E7SH. The data show that these adenoviral vectors induced HPV18 E6-specific T-cells to similar levels.

Figure 20:
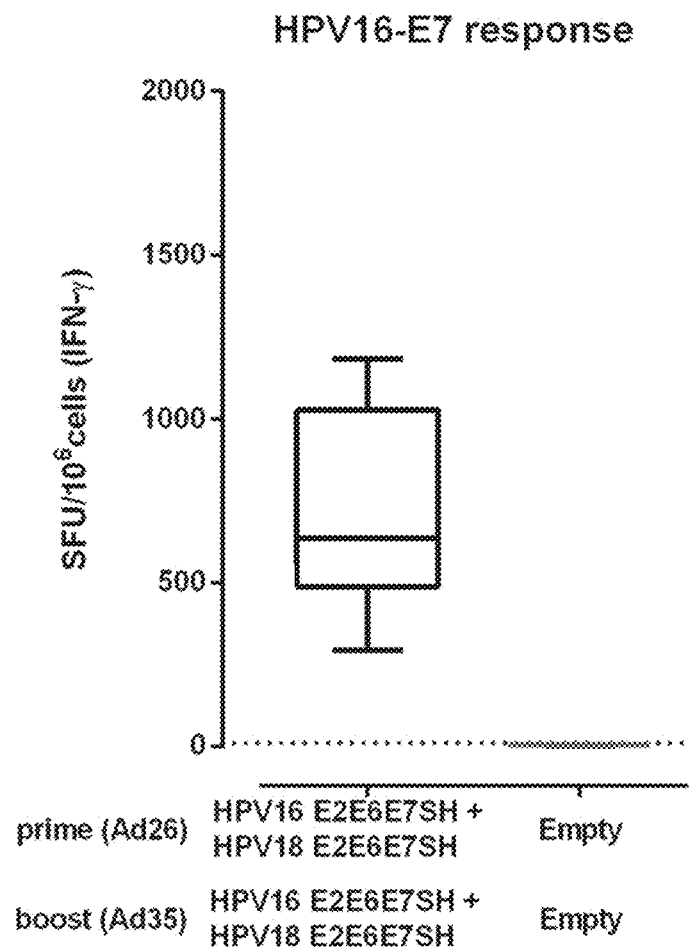
FIG. 20. Immunogenicity of combined HPV16 and HPV18 vectors—IFNγ ELISPOT analysis. CB6F1 mice were immunized with adenovectors (type 26) expressing the E2E6E7SH transgenes from both HPV16 (encoding SEQ ID NO: 3) and HPV18 (encoding SEQ ID NO: 22). Four weeks after prime immunization the mice received an heterologous boost immunization with adenoviral vectors of type 35 with the same E2E6E7SH transgenes. Two weeks after the boost immunization the mice were sacrificed and isolated splenocytes were stimulated overnight with 15mer peptide pools corresponding to HPV16 E7 (A) or HPV18 E6 (B). Responses are given as SFU per $10^6$ splenocytes.

Example 10. Combining Adenoviral Vectors Expressing HPV16 and HPV18 Designer Constructs Combining designer constructs for different HPV types offers the possibility to make a treatment vaccine for different HPV types. To evaluate the ability of the adenoviral vectors expressing different designer sequences to induce immune responses, mice were immunized by intramuscular injection with the adenovectors (Ad26) expressing HPV16 E2E6E7SH (encoding protein comprising amino acid sequence set forth in SEQ ID NO: 3) and with Ad26 expressing HPV18 E2E6E7SH (encoding protein comprising amino acid sequence set forth in SEQ ID NO: 22) with a dose of $1*10^{10}$ vp for each vector or adenovectors not encoding a transgene (Empty). Four weeks after the immunization the immune responses were boosted by immunization with Ad35 vectors expressing the same antigens. Immune responses were measured two weeks after the boost immunization. Cells were stimulated overnight with peptide pools corresponding to E6 of HPV18 or E7 of HPV16 and responses were measured by IFNγ ELISPOT. The data are presented in FIG. 20.

The data show that immunization of mice with Ad26/35 vectors expressing HPV16 E2E6E7SH and HPV18 E2E6E7SH resulted in cellular immune responses against both (i.e. HPV16 and HPV18) designer proteins.

In an independent experiment with a similar immunization schedule (Ad26 prime and Ad35 boost) we compared the immune response induced by Ad expressing HPV16 E2E6E7SH and Ad expressing HPV18 E2E6E7SH together to that induced in mice immunized with Ad expressing HPV16 E2E6E7SH alone or Ad expressing HPV18 E2E6E7SH alone. Immune responses were measured two weeks after boost immunization, and cells were stimulated overnight with peptide pools corresponding to E2, E6 or E7 of HPV16 and HPV18 and the responses were measured by IFNγ ELISPOT as well as intracellular cytokine staining. Although co-administration in a single composition of Ad expressing HPV16 E2E6E7SH and Ad expressing HPV18 E2E6E7SH did result in an overall lower magnitude of CD4 and CD8 responses as compared to animals that were only immunized with the individual vaccine components, the co-administration induced a similar breadth of the immune responses (data not shown).

Co-administration of HPV16 E2E6E7SH and HPV18 E2E6E7SH expressing constructs according to the invention is thus possible to induce cellular immune responses to both HPV16 and HPV18.

Example 11. Immunogenicity of Combined Designer Constructs in Rhesus Macaques

Figure 21:
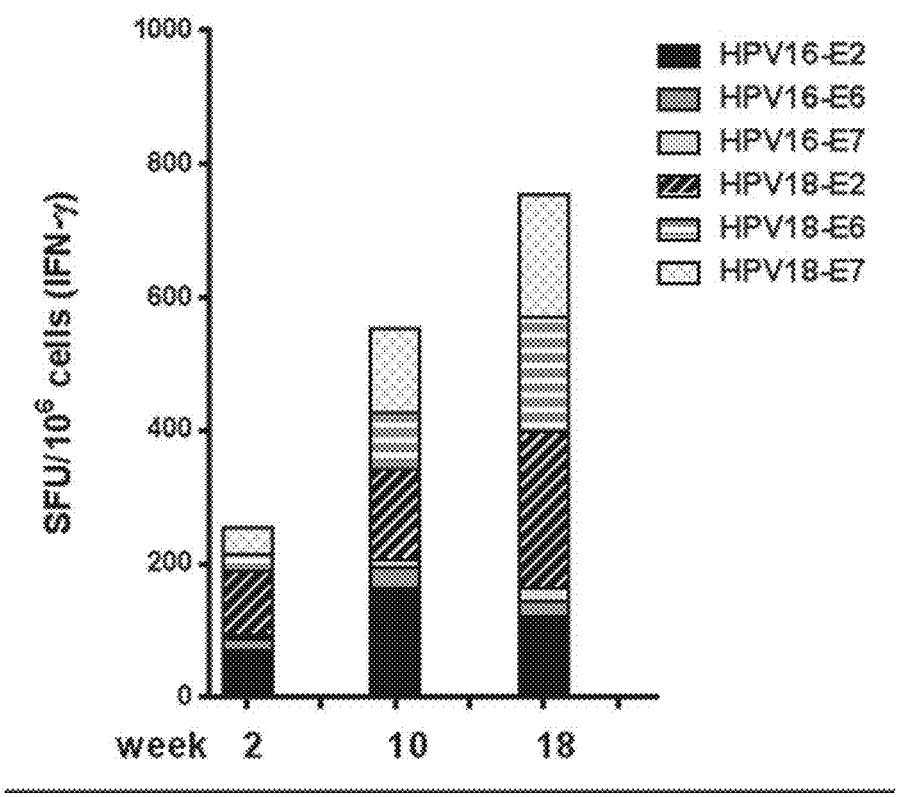
FIG. 21. Cellular immunogenicity of combined HPV16 and HPV18 vaccine in Rhesus macaques. Rhesus macaques were immunized according to the scheme as presented in FIG. 11, with a combination of HPV16 and HPV18 designer constructs. At day 0: Eight animals received a mixture of Ad26.HPV16-E2E6E7SH and Ad26.HPV18-E2E6E7SH by intramuscular immunization (i.m). A boost immunization with the same vectors was given at 8 weeks. At 16 weeks, animals received a second boost immunization with a mixture of two Ad35 vectors expressing the same HPV16 and HPV18 E2E6E7SH fusion proteins. The dose of adenovectors was $1*10^{11}$ vp per vector per immunization. Blood drawings were performed at several time points. Cellular immune responses in PBMCs were measured by IFNγ ELISPOT. PBMCs were stimulated with peptide pools corresponding to E2, E6 or E7 of HPV16 and HPV18 and the number of spot-forming units (SFU) in $1*10^6$ PBMCs were determined. The figure shows cumulative responses for all six tested peptide pools at 2 weeks after each immunization. For details see example 11.

To evaluate the ability of the adenoviral vectors expressing the designer sequences of the invention to induce immune responses in non-human primates, rhesus macaques were immunized by intramuscular injection with the mix of two separate adenovectors as in the previous example, i.e. Ad26 vectors together expressing HPV16 and HPV18 E2E6E7SH, at a dose of $1*10^{11}$ vp for each vector, or adenovectors not encoding a transgene (Empty). Eight weeks after the immunization, animals received a boost immunization with Ad26 vectors expressing the same antigens. At week 16 the animals received one more injection with the Ad35 vectors expressing the same antigens. Blood samples were taken at several time points and isolated white blood cells were stimulated overnight with peptide pools corresponding to E2, E6 or E7 for both HPV16 and HPV18. Specific responses were measured by IFNγ ELISPOT. The data are presented in FIG. 21. In addition at week 10 and week 18 post prime immunization, the cellular immune response specific to peptides spanning the novel junctions in the HPV18 designer molecules of the invention was evaluated. The induction of IFNγ response against these junctional peptides was in all animals below the limit of detection of <50 SFU per $1*10^6$ PBMC (data not shown).

The data show that immunization of non-human primates with a combination of Ad26 vectors together expressing HPV16 E2E6E7SH and HPV18 E2E6E7SH resulted in cellular immune responses against several of the HPV proteins that are present in the encoded transgenes. Responses could be boosted by the additional immunization with Ad26 vectors. The additional boost immunization at week 16 with the corresponding Ad35 vector further increased the immune responses.

Example 12. Therapeutic Efficacy of Combined Constructs in a Mouse Tumor Model

A polypeptide of the invention corresponding to HPV16 E6 and E7 is capable of inducing cellular immune responses in mice that will lead to a therapeutic effect in the TC-1 model (as shown in example 5). The therapeutic effect of a combination of adenoviral vectors together expressing both HPV16 and HPV18 designer proteins was tested in this same model. Without vaccine the tumors grew rapidly and reach a pre-determined size of 1000 mm³ within 30 days at which point the mice were sacrificed for ethical reasons.

Figure 22:
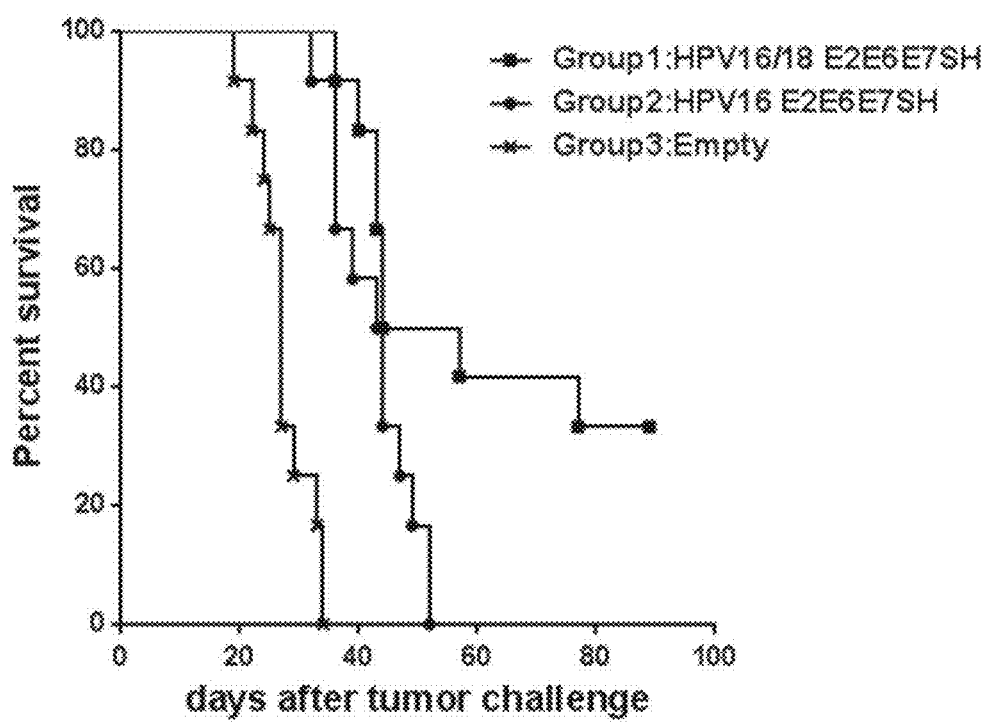
FIG. 22. Therapeutic effect of combined adenovectors expressing HPV16 and HPV18 E2E6E7SH. C57BL/6 mice were injected sub-cutaneously with $5*10^4$ TC-1 cells at day 0. After six days, when tumors were palpable, mice were immunized with Ad26.HPV16-E2E6E7SH or a mixture of Ad26.HPV16-E2E6E7SH and Ad26.HPV18-E2E6E7SH. Control mice received Ad26.Empty. All mice received a boost immunization at day 20 with the corresponding Ad35 vectors. Tumor volume was calculated as $(width^2*length)/2$. Mice were sacrificed when tumor volumes surpassed 1000 $mm^3$. The graphs show survival after TC-1 injection. Three mice immunized with the combined HPV16+HPV18 vaccine were tumor free at the end of the experiment. The median survival time of mice treated with Ad.HPV16-E2E6E7SH was not significantly different compared with mice immunized with Ad.HPV16/18-E2E6E7SH.

In this experiment, C57BL/6 mice were injected subcutaneously with $5*10^4$ TC-1 cells at day 0. After six days, when tumors were palpable, mice were immunized with Ad26.HPV16-E2E6E7SH or a mixture of Ad26.HPV16-E2E6E7SH and Ad26.HPV18-E2E6E7SH. All mice also received a boost immunization at day 20 with the corresponding Ad35 vectors. It was observed that the prime-boost immunizations with adenoviral vectors expressing HPV16 E2E6E7SH prolonged the survival of the mice significantly (FIG. 22). With a combination of adenoviral vectors together expressing both HPV16 E2E6E7SH and HPV18 E2E6E7SH, a similar mean survival time was observed. In the group of mice that received the combination vaccine, three animals were tumor free at the end of the monitoring period of 90 days.

Results from other experiments showed that the prime-boost immunizations with adenoviral vectors together expressing HPV16 E2E6E7SH and HPV18 E2E6E7SH also prolonged the survival of the mice significantly when the prime immunization was administered earlier, e.g., 4 days after the mice were sub-cutaneously injected with the TC-1 cells (data not shown).

In conclusion, immunization with a combination of adenoviral vectors together expressing HPV16- and HPV18-specific designer polypeptides of the invention significantly reduced tumor growth or completely eradicated established tumors in a well-established challenge model for HPV16-induced cancer.

Example 13: Construction of MVA Vector for HPV16E2E6E7 and HPV18E2E6E7 (MVA-BN mBN411)

In the instant example, we have generated an MVA-BN vector including HPV16 E2E6E7 and HPV18 E2E6E7. It is understood that MVA-BN vectors can be used to express the E6E7, either with or without E2, and with or without additional sequences to augment the immunogenicity of the encoded polypeptide.

We designed a novel nucleic acid (SEQ ID NO: 24) coding for the polypeptide HPV16 E2E6E7 (SEQ ID NO: 3) and a novel nucleic acid (SEQ ID NO: 25) coding for the polypeptide HPV18 E2E6E7 (SEQ ID NO: 22). The novel nucleic acids were designed for human expression and minimal homology among each other. The nucleic acid sequences were synthesized at Geneart.

The PrMVA13.5long promoter (SEQ ID NO: 26) was included in front of the ATG start codon of HPV16 E2E6E7 and two stop codons (5' TGA TGA 3') were added at the end of the coding sequence. The PrHyb promoter (SEQ ID NO: 27) was included in front of the ATG start codon of HPV18 E2E6E7 and two stop codons (5' TGA TGA 3') were added at the end of the coding sequence. Early termination signals (5' TTTTTAT 3') were inserted behind the respective stop codons of both nucleic acid sequences.

The genes were inserted via SacII and NheI into pBNX202, a transfer vector encoding IGR88/89 MVA-BN homologous regions and therefore allow insertion into an insertion site of IGR88/89 of MVA-BN via homologous recombination. Moreover pBNX202 encodes mRFP1 and ecogpt for positive selection as well as a repetitive sequence of the IGR 88/89 MVA-BN homologous region Flank 2 for later excision of the selection cassette via homologous recombination in the absence of selective pressure.

The MVA based vectors were generated in primary chicken fibroblasts (CEF) and produced as described herein.

The CEF cells were weekly isolated of chicken embryos and maintained in VP-SFM medium without FBS.

Briefly, CEF cells were transfected with MVA vector plasmid, using Fugene according to the instructions provided by the manufacturer (Promega) and a coinfection with MVA-BN has been performed. Cells were harvested after two days, sonified and further plaque purified. The virus was plaque purified and amplified in CEF cells cultured in a single well of a multiwell 24-tissue culture plate or a single well of a multiwell 96-tissue culture plate respectively. Further amplification was carried out in CEF cells cultured in a single well of a multiwell 6-tissue plate and subsequently in a T175 tissue culture flask.

To generate the virus mBN 411A, eleven passages were generated, three passages of which were plaque purifications in VP-SFM medium containing Mycophenolic acid/xanthine and hypoxanthine. To generate mBN411B, seventeen passages were generated, six passage of which were plaque purifications in VP-SFM medium without selective pressure to allow excision of the selection cassette via homologous recombination.

The MVA mBN 411 virus is thus an MVA-BN comprising in its IGR88/89 region a nucleic acid encoding designer polypeptide HPV16 E2E6E7SH (SEQ ID NO: 3) under control of a PrMVA13.5long promoter (SEQ ID NO: 26) and a nucleic acid encoding designer polypeptide HPV18 E2E6E7SH (SEQ ID NO: 22) under control of a PrHyb promoter (SEQ ID NO: 27). The MVA mBN411 virus was used in subsequent experiments in prime-boost regimens with adenovirus vectors encoding designer polypeptides.

Example 14. Immunogenicity of HPV16 and HPV18 Designer Constructs in a Ad26 Prime and MVA Boost Immunization in Mice HPV16 and HPV18-specific immune response induced by a prime immunization with adenovectors (Ad26) and boost immunization with Modified Vaccinia Ankara Virus (MVA) were evaluated. As a priming immunization, mice were vaccinated by intramuscular injection with adenovector (Ad26) expressing HPV16 E2E6E7SH (encoding protein comprising amino acid sequence set forth in SEQ ID NO: 3) and with Ad26 expressing HPV18 E2E6E7SH (encoding protein comprising amino acid sequence set forth in SEQ ID NO: 22), using a dose of $1*10^{10}$ vp for each vector, or as a control with adenovectors not encoding a transgene (Empty). Eight weeks after the prime immunization animals were boost-immunized with MVA expressing the same antigens as during prime immunization (MVA BN mBN 411A, at a dose of $8.9 \times 10^7$ TCID50/mouse), while another group of mice was boost-immunized with Ad35 vectors expressing the same antigens as during prime immunization. Control animals were boost-immunized with an MVA vector not encoding a transgene (Control).

Figure 23:
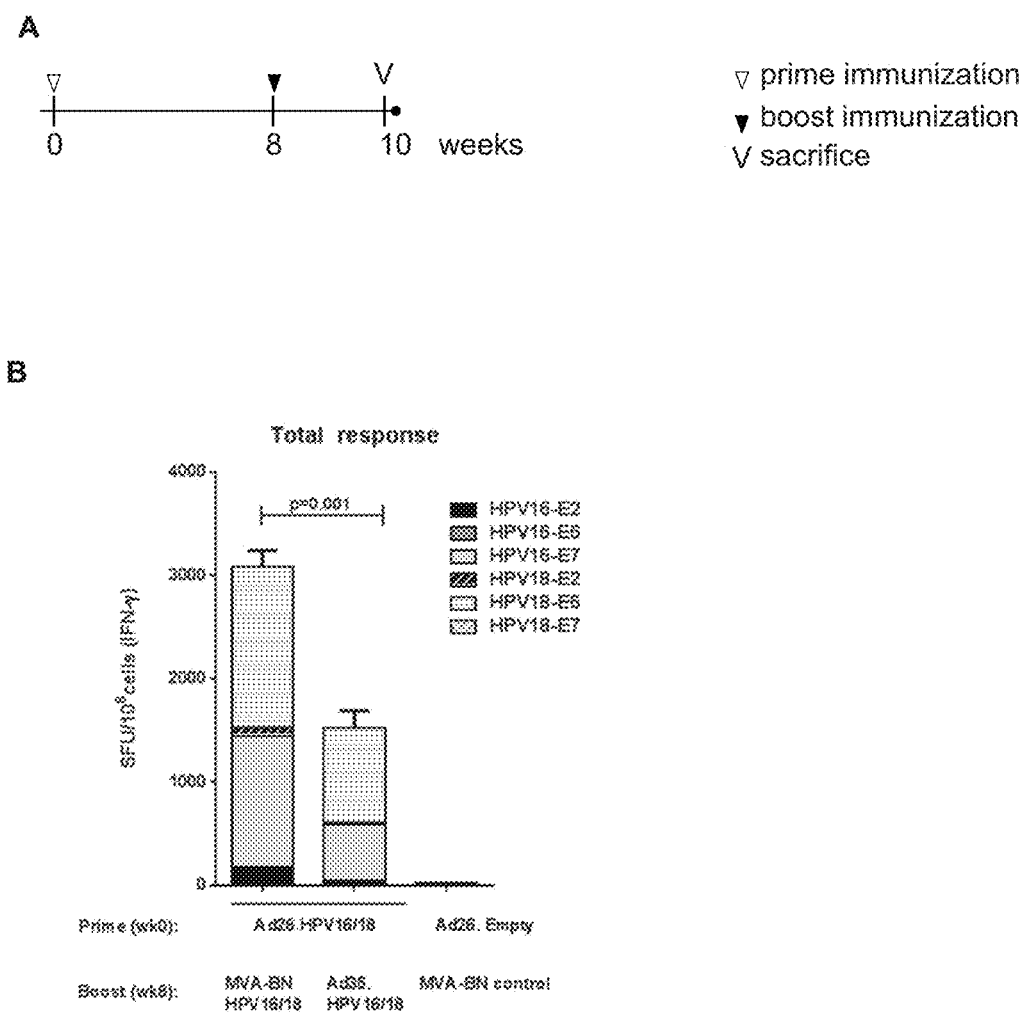
FIG. 23. Use of Modified Vaccinia Ankara (MVA) vectors to boost immune responses. (A). Immunization scheme. CB6F1 mice were immunized with a mixture of an Ad26 vector expressing HPV16 E2E6E7SH (HPV16) and Ad26 vector expressing HPV18 E2E6E7SH, or with an Ad26 vector expressing no transgene (empty). Eight weeks later the immunizations were repeated with an MVA-BN or with an Ad35 vector expressing the same antigen as the Ad26 vectors. Control animals were boost-immunized with an MVA-BN vector expressing no transgene (control). Two weeks after the second immunization the mice were sacrificed and isolated splenocytes were stimulated overnight with 15mer peptide pools corresponding to E2, E6 or E7 of HPV16 and HPV18 E6. (B) shows the total IFNγ response per group as SFU per $10^6$ splenocytes. (student t-test on log transformed data, with alpha=0.05, excluding negative control).

Immune responses were measured two weeks after the boost immunization. Cells were stimulated overnight with peptide pools corresponding to E2, E6 or E7 of HPV16 or HPV18 and responses were measured by IFN$\gamma$ ELISPOT. The data are presented in FIG. 23.

The data show that immunization of mice with either Ad26/Ad35 or Ad26/MVA vectors expressing HPV16 E2E6E7SH and HPV18 E2E6E7SH resulted in cellular immune responses against both (i.e. HPV16 and HPV18) designer proteins. The overall response was highest in animals boost-immunized with MVA expressing HPV16 E2E6E7SH and HPV18 E2E6E7SH.

Example 15. Immunogenicity of HPV16 and HPV18 Designer Constructs in a Ad26 Prime and MVA Boost Immunization in Rhesus Macaques We evaluated the ability of the adenoviral vectors and MVA vectors expressing the designer sequences of the invention to induce immune responses in non-human primates. Rhesus macaques (non-human primates, NHP) were prime immunized by intramuscular injection with the mix of two separate adenovectors as in example 11, i.e. Ad26 expressing HPV16 E2E6E7SH and Ad26 expressing HPV18 E2E6E7SH, at a dose of $1*10^{11}$ vp for each adenoviral vector. Eight weeks after the prime immunization, animals were boosted with MVA-BN (mBN 411A, a vector expressing these same antigens, at a dose of about $1.80 \times 10^8$ TCID50/NHP).

Figure 24:
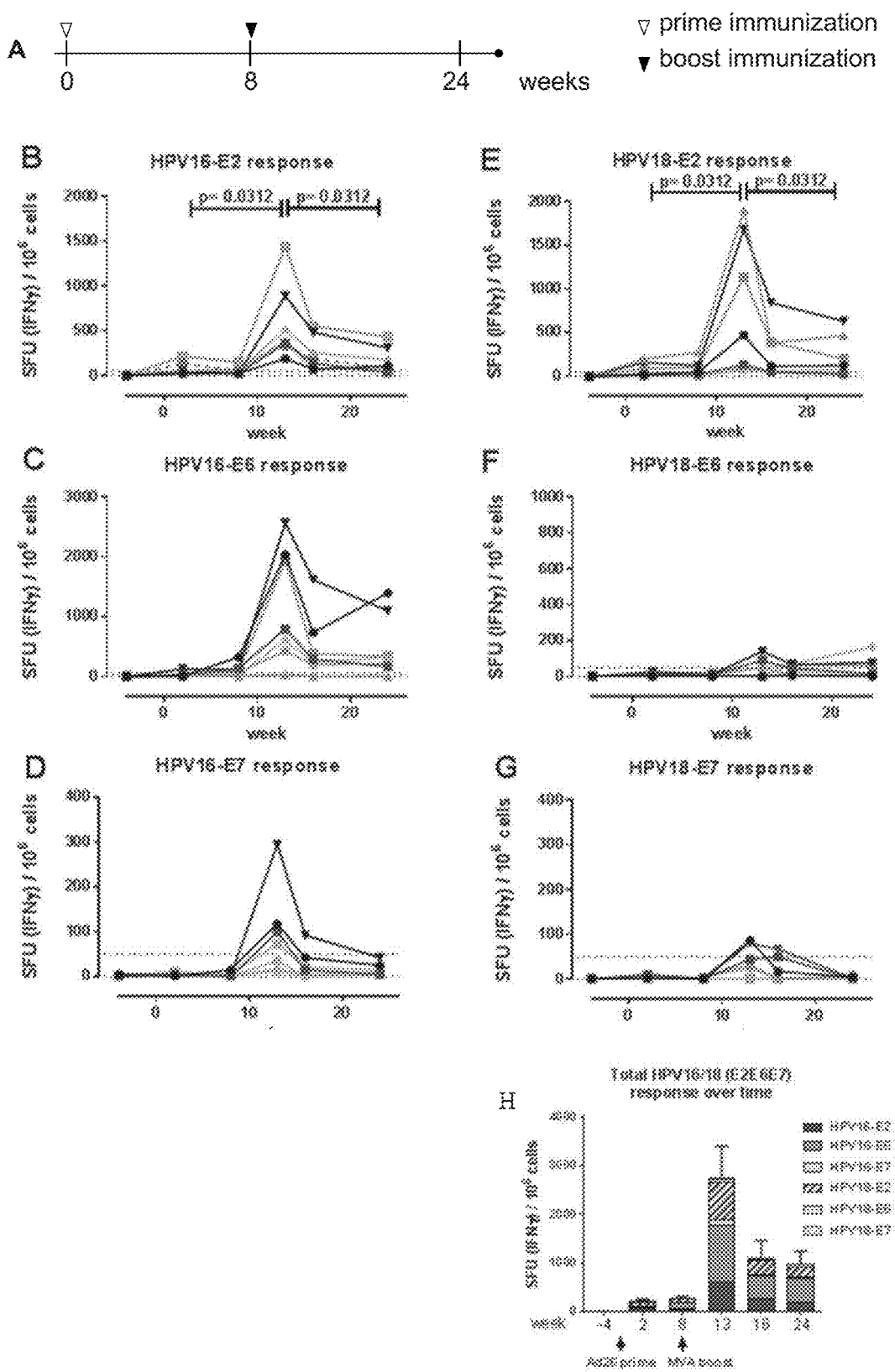
FIG. 24. Cellular immunogenicity induced by Ad26 prime and MVA boost in Rhesus macaques. Rhesus macaques were immunized according to the scheme as presented in FIG. 24A, with a combination of HPV16 and HPV18 designer constructs. At day 0: Several animals received a mixture of Ad26.HPV16-E2E6E7SH and Ad26.HPV18-E2E6E7SH by intramuscular immunization (i.m). A boost immunization MVA-BN encoding HPV16 E2E6E7SH and HPV18 E2E6E7SH vectors was given at 8 weeks. The dose of adenovectors was $1*10^{11}$ vp per vector. The dose of MVA was $1.8\times10^8$ $TCID^{50}$. Blood drawings were performed at several time points. Cellular immune responses in PBMCs were measured by IFNγ ELISPOT. PBMCs were stimulated with peptide pools corresponding to HPV16 E2 (B), HPV16 E6 (C), HPV16 E7 (D), HPV18 E2 (E), HPV18 E6 (F), HPV18 E7 (G) and the number of spot-forming units (SFU) in $1*10^6$ PBMCs were determined and shown in FIG. 24B-24G, respectively.

Blood samples were taken at several time points and isolated white blood cells are stimulated overnight with peptide pools corresponding to E2, E6 or E7 for both HPV16 and HPV18. Specific responses are measured by IFN$\gamma$ ELISPOT. The data are presented in FIG. 24.

The data show that immunization of Rhesus macaques with Ad/MVA expressing HPV16 E2E6E7SH and HPV18 E2E6E7SH resulted in cellular immune responses against the designed antigens. Moreover the induced cellular responses appear to be broadened by MVA boosting, with responses against 3-5 of the 6 different HPV16 and HPV18 antigens that are expressed by the vaccine vectors.

Example 16. Therapeutic Efficacy of HPV16 and HPV18 Designer Constructs in a Ad26 Prime and MVA Boost Immunization in Mice The therapeutic effect of a prime boost immunization with adenoviral vectors and MVA expressing HPV16 and HPV18 designer proteins were tested in the same TC-1 model as described under example 12. The tumor growth was followed over time, animals are sacrificed for ethical reasons once the tumor volume reaches >1000 mm$^3$.

The experimental design is as follows:

| Group (n = 36 total) | Tumor cell inoculation (day 0) | Prime day 6 (dose) | Boost day 20 (dose) | Sacrifice (day) |
|---|---|---|---|---|
| 1. Pos control (n = 12) | 50,000 TC-1 cells | Ad26.HPV16-Tx + Ad26.HPV18-Tx ($1 \times 10^{10}$ vp/vector) | Ad35.HPV16-Tx + Ad35.HPV18-Tx ($1 \times 10^{10}$ vp/vector) | 90 or earlier if tumor volume >1000 mm$^3$ |
| 2. Test (n = 12) | 50,000 TC-1 cells | Ad26.HPV16-Tx + Ad26.HPV18-Tx ($1 \times 10^{10}$ vp/vector) | MVA-BN-HPV16/18-Tx ($8.9 \times 10^7$ TCID50) | 90 or earlier if tumor volume >1000 mm$^3$ |
| 3. Neg control (n = 12) | 50,000 TC-1 cells | Ad26.empty ($1 \times 10^{10}$ vp/vector) | MVA-BN-control ($8.9 \times 10^7$ TCID50) | 90 or earlier if tumor volume >1000 mm$^3$ |

Treatment Groups.

At the day of priming tumors were palpable in minimum 50% of the animals. (HPV16-Tx and HPV18-Tx are indications for the constructs of the invention encoding polypeptides having SEQ ID NOs: 3 and 20, respectively).

Blood was drawn before TC-1 tumor cell inoculation, at day 19 (i.e. one day before boost administration) and at day 34 (i.e. two weeks after boost administration), and in some mice blood was also drawn at day 90 after TC-1 tumor cell inoculation.

Figure 25:
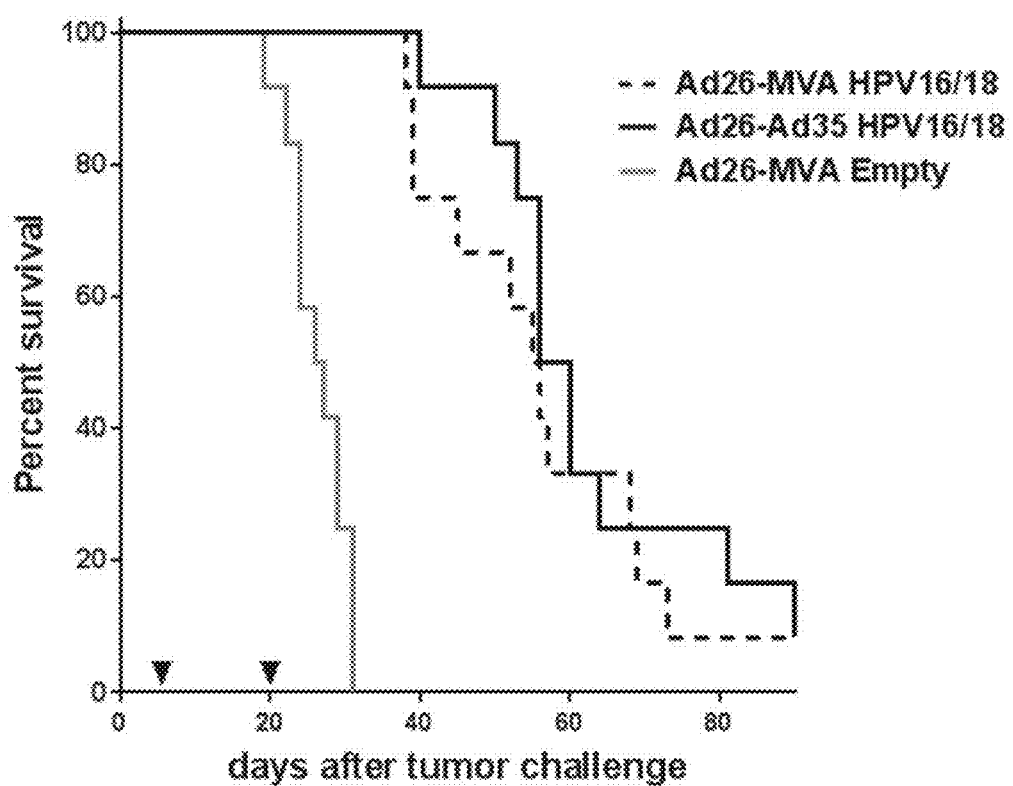
FIG. 25. Therapeutic effect of Ad26 priming and boost with either Ad35 or MVA vectors expressing HPV16 and HPV18 E2E6E7SH. C57BL/6 mice were injected sub-cutaneously with $5*10^4$ TC-1 cells at day 0. After six days, when tumors were palpable, mice were immunized with a mixture of Ad26.HPV16-E2E6E7SH and Ad26.HPV18-E2E6E7SH. Control mice received Ad26.Empty. Mice received a boost immunization at day 20 with Ad35 vectors or MVA encoding HPV16/18 E2E6E7SH. Control animals were immunized with a MVA not encoding a transgene. Tumor volume was calculated as (width$^2$*length)/2. Mice were sacrificed when tumor volumes surpassed 1000 mm$^3$. The graphs show survival after TC-1 injection. One mouse boost immunized with Ad35.HPV16 E2E6E7SH and Ad35.HPV18 E2E6E7SH and one mouse boost immunized with MVA-BN HPV16/18 E2E6E7SH were tumor free at the end of the experiment. The median survival time of mice boosted with Ad35.HPV16/18-E2E6E7SH was not significantly different compared with mice boost immunized with MVA-BN HPV16/18-E2E6E7SH.

In this experiment, C57BL/6 mice were injected subcutaneously with $5*10^4$ TC-1 cells at day 0. After six days, when tumors were palpable, mice were immunized with a mixture of Ad26.HPV16-E2E6E7SH and Ad26.HPV18-E2E6E7SH. Mice received a boost immunization at day 20 with either Ad26.HPV16-E2E6E7SH and Ad26.HPV18-E2E6E7SH or MVA-BN-HPV16/18-Tx. Control mice were primed with an Ad26 not encoding a transgene and boosted with a MVA not encoding a transgene. Animals immunized with either Ad26/Ad35 encoding E2E6E7SH or MVA-BN encoding HPV16/18 E2E6E7SH resulted in a comparable prolonged survival and median survival time; in both groups one mouse was alive and tumor free at the end of the monitoring period of 90 days. The data are represented in FIG. 25.

The examples in the specification are considered as exemplary only, with a true scope and spirit of the invention being indicated by the following claims.

REFERENCES

Abbink P, Lemckert A A, Ewald B A, Lynch D M, Denholtz M, Smits S, Holterman L, Damen I, Vogels R, Thorner A R, O'Brien K L, Carville A, Mansfield K G, Goudsmit J, Havenga M J, Barouch D H (2007) Comparative seroprevalence and immunogenicity of six rare serotype recombinant adenovirus vaccine vectors from subgroups B and D. J Virol 81:4654-4663

Ausubel F M (1995) Short protocols in molecular biology: a compendium of methods from Current protocols in molecular biology. Wiley, [Chichester]

Brokaw J L, Blanco M, McBride A A (1996) Amino Acids Critical for the Functions of the Bovine Papillomavirus Type 1 E2 Transactivator. J Virol 70: 23-29

Cottingham M G, Carroll F, Morris S J, Turner A V, Vaughan A M, Kapulu M C, Colloca S, Siani L, Gilbert S C, Hill A V (2012) Preventing spontaneous genetic rearrangements in the transgene cassettes of adenovirus vectors. Biotechnol Bioeng 109:719-728

Daayana S, Elkord E, Winters U, Pawlita M, Roden R, Stern P L, Kitchener H C (2010) Phase II trial of imiquimod and HPV therapeutic vaccination in patients with vulval intraepithelial neoplasia. Br J Cancer 102:1129-1136 de Jong A, van der Burg S H, Kwappenberg K M, van der Hulst J M, Franken K L, Geluk A, van Meijgaarden K E, Drijfhout J W, Kenter G, Vermeij P, Melief C J, Offringa R (2002) Frequent detection of human papillomavirus 16 E2-specific T-helper immunity in healthy subjects. Cancer Res 62:472-479

Edholm D, Molin M, Bajak E, Akusjarvi G (2001) Adenovirus vector designed for expression of toxic proteins. J Virol 75:9579-9584

Evans R K, Nawrocki D K, Isopi L A, Williams D M, Casimiro D R, Chin S, Chen M, Zhu D M, Shiver J W, Volkin D B (2004) Development of stable liquid formulations for adenovirus-based vaccines. J Pharm Sci 93:2458-2475

Fallaux F J, Bout A, van der Velde I, van den Wollenberg D J, Hehir K M, Keegan J, Auger C, Cramer S J, van Ormondt H, van der Eb A J, Valerio D, Hoeben R C (1998) New helper cells and matched early region 1-deleted adenovirus vectors prevent generation of replication-competent adenoviruses. Hum Gene Ther 9:1909-1917

Frøkær S, Hovgaard L (2000) Pharmaceutical formulation development of peptides and proteins. Taylor & Francis, London Gall J G, Lizonova A, EttyReddy D, McVey D, Zuber M, Kovesdi I, Aughtman B, King C R, Brough D E (2007) Rescue and production of vaccine and therapeutic adenovirus vectors expressing inhibitory transgenes. Mol Biotechnol 35:263-273

Gao G P, Engdahl R K, Wilson J M (2000) A cell line for high-yield production of E1-deleted adenovirus vectors without the emergence of replication-competent virus. Hum Gene Ther 11:213-219

Gennaro A R (1990) Remington's pharmaceutical sciences. Mack

Gilbert R, Guilbault C, Gagnon D, Bernier A, Bourget L, Elahi S M, Kamen A, Massie B (2014) Establishment and validation of new complementing cells for production of E1-deleted adenovirus vectors in serum-free suspension culture. J Virol Methods 208:177-188

Hamid O, Carvajal R D (2013) Anti-programmed death-1 and anti-programmed death-ligand 1 antibodies in cancer therapy. Expert Opin Biol Ther 13:847-861

Harlow E, Lane D (1988) Antibodies: a laboratory manual. Cold Spring Harbor Laboratory, New York Havenga M, Vogels R, Zuijdgeest D, Radosevic K, Mueller S, Sieuwerts M, Weichold F, Damen I, Kaspers J, Lemckert A, van Meerendonk M, van der Vlugt R, Holterman L, Hone D, Skeiky Y, Mintardjo R, Gillissen G, Barouch D, Sadoff J, Goudsmit J (2006) Novel replication-incompetent adenoviral B-group vectors: high vector stability and yield in PER.C6 cells. J Gen Virol 87:2135-2143

Henken F E, Oosterhuis K, Ohlschlager P, Bosch L, Hooijberg E, Haanen J B, Steenbergen R D (2012) Preclinical safety evaluation of DNA vaccines encoding modified HPV16 E6 and E7. Vaccine 30:4259-4266

Hildesheim A, Herrero R, Wacholder S, Rodriguez A C, Solomon D, Bratti M C, Schiller J T, Gonzalez P, Dubin G, Porras C, Jimenez S E, Lowy D R (2007) Effect of human papillomavirus 16/18 L1 viruslike particle vaccine among young women with preexisting infection: a randomized trial. JAMA 298:743-753

Hoganson D K, Ma J C, Asato L, Ong M, Printz M A, Huyghe B G, Sosnowshi B A, D'Andrea M J (2002) Development of a stable adenoviral vector formulation. Bioprocess J 1:43-48

Hoof I, Peters B, Sidney J, Pedersen L E, Sette A, Lund O, Buus S, Nielsen M (2009) NetMHCpan, a method for MHC class I binding prediction beyond humans. Immunogenetics 61:1-13

Horwitz M S (1996) Adenoviruses. In: Fields B N, Knipe D M, Baines J D (eds) Virology. Raven Press Ltd, New York Kenter G G, Welters M J, Valentijn A R, Lowik M J, Berends-van der Meer D M, Vloon A P, Essahsah F, Fathers L M, Offringa R, Drijfhout J W, Wafelman A R, Oostendorp J, Fleuren G J, van der Burg S H, Melief C J (2009) Vaccination against HPV-16 oncoproteins for vulvar intraepithelial neoplasia. N Engl J Med 361:1838-1847

Kibbe A H (2000) Handbook of pharmaceutical excipients. Pharmaceutical Press, London Kim T J, Jin H T, Hur S Y, Yang H G, Seo Y B, Hong S R, Lee C W, Kim S, Woo J W, Park K S, Hwang Y Y, Park J, Lee I H, Lim K T, Lee K H, Jeong M S, Surh C D, Suh Y S, Park J S, Sung Y C (2014) Clearance of persistent HPV infection and cervical lesion by therapeutic DNA vaccine in CIN3 patients. Nat Commun 5:5317 (doi: 10.1038/ncomms6317)

Kovesdi I, Hedley S J (2010) Adenoviral producer cells. Viruses 2:1681-1703

Lin K Y, Guarnieri F G, Staveley-O'Carroll K F, Levitsky H I, August J T, Pardoll D M, Wu T C (1996) Treatment of established tumors with a novel vaccine that enhances major histocompatibility class II presentation of tumor antigen. Cancer Res 56:21-26

Lundegaard C, Lamberth K, Harndahl M, Buus S, Lund O, Nielsen M (2008) NetMHC-3.0: accurate web accessible predictions of human, mouse and monkey MHC class I affinities for peptides of length 8-11. Nucleic Acids Res 36:W509-512

Massimi P, Banks L (2005) Transformation Assays for HPV Oncoproteins. In: Davy C, Doorbar J (eds) Human Papillomaviruses: Methods and Protocols. Vol 119: Methods in Molecular Medicine Springer, Berlin, pp 381-395

Matthews D A, Cummings D, Evelegh C, Graham F L, Prevec L (1999) Development and use of a 293 cell line expressing lac repressor for the rescue of recombinant adenoviruses expressing high levels of rabies virus glycoprotein. J Gen Virol 80 (Pt 2):345-353

McPherson M J, Hames B D, Taylor G R (1995) PCR 2: a practical approach. IRL Press at Oxford University Press, Oxford Mellman I, Coukos G, Dranoff G (2011) Cancer immunotherapy comes of age. Nature 480:480-489

Mullick A, Xu Y, Warren R, Koutroumanis M, Guilbault C, Broussau S, Malenfant F, Bourget L, Lamoureux L, Lo R, Caron A W, Pilotte A, Massie B (2006) The cumate gene-switch: a system for regulated expression in mammalian cells. BMC Biotechnol 6:43

Munger K, Phelps W C, Bubb V, Howley P M, Schlegel R (1989) The E6 and E7 genes of the human papillomavirus type 16 together are necessary and sufficient for transformation of primary human keratinocytes. J Virol 63:4417-4421

Ogun S A, Dumon-Seignovert L, Marchand J B, Holder A A, Hill F (2008) The oligomerization domain of C4-binding protein (C4 bp) acts as an adjuvant, and the fusion protein comprised of the 19-kilodalton merozoite surface protein 1 fused with the murine C4 bp domain protects mice against malaria. Infect Immun 76:3817-3823

Oosterhuis K, Aleyd E, Vrijland K, Schumacher T N, Haanen J B (2012a) Rational Design of DNA Vaccines for the Induction of Human Papillomavirus Type 16 E6- and E7-Specific Cytotoxic T-Cell Responses. Hum Gene Ther 23:1301-1312

Oosterhuis K, Ohlschlager P, van den Berg J H, Toebes M, Gomez R, Schumacher T N, Haanen J B (2011) Preclinical development of highly effective and safe DNA vaccines directed against HPV 16 E6 and E7. Int J Cancer 129:397-406

Oosterhuis K, van den Berg J H, Schumacher T N, Haanen J B (2012b) DNA vaccines and intradermal vaccination by DNA tattooing. Curr Top Microbiol Immunol 351:221-250

Peters B, Tong W, Sidney J, Sette A, Weng Z (2003) Examining the independent binding assumption for binding of peptide epitopes to MHC-I molecules. Bioinformatics 19:1765-1772

Prakash S S, Grossman S R, Pepinsky R B, Laimins L A, Androphy E J (1992) Amino acids necessary for DNA contact and dimerization imply novel motifs in the papillomavirus E2 trans-activator. Genes Dev 6:105-116

Rubinchik S, Ding R, Qiu A J, Zhang F, Dong J (2000) Adenoviral vector which delivers FasL-GFP fusion protein regulated by the tet-inducible expression system. Gene Ther 7:875-885

Sambrook J F E F M T (1989) Molecular cloning: a laboratory manual. Cold Spring Harbor Laboratory, Cold Spring Harbor, N.Y.

Sakai H, Yasugi T, Benson J D, Dowhanick J J, Howley P M (1996) Targeted Mutagenesis of the Human Papillomavirus Type 16 E2 Transactivation Domain Reveals Separable Transcriptional Activation and DNA Replication Functions. J Virol 70: 1602-1611

Sedman S A, Barbosa M S, Vass W C, Hubbert N L, Haas J A, Lowy D R, Schiller J T (1991) The full-length E6 protein of human papillomavirus type 16 has transforming and trans-activating activities and cooperates with E7 to immortalize keratinocytes in culture. J Virol 65:4860-4866

Shenk T (1996) Adenoviridae and their Replication. In: Fields B N, Knipe D M, Baines J D (eds) Virology. Raven Press Ltd, New York Smahel M, Sima P, Ludvikova V, Vonka V (2001) Modified HPV16 E7 Genes as DNA Vaccine against E7-Containing Oncogenic Cells. Virology 281:231-238 van der Burg S H, Melief C J (2011) Therapeutic vaccination against human papilloma virus induced malignancies. Curr Opin Immunol 23:252-257

Watson J D (1992) Recombinant DNA. Scientific American Books, New York

Wieking B G, Vermeer D W, Spanos W C, Lee K M, Vermeer P, Lee W T, Xu Y, Gabitzsch E S, Balcaitis S, Balint J P, Jr., Jones F R, Lee J H (2012) A non-oncogenic HPV 16 E6/E7 vaccine enhances treatment of HPV expressing tumors. Cancer Gene Ther 19:667-674

Yan J, Reichenbach D K, Corbitt N, Hokey D A, Ramanathan M P, McKinney K A, Weiner D B, Sewell D (2009) Induction of antitumor immunity in vivo following delivery of a novel HPV-16 DNA vaccine encoding an E6/E7 fusion antigen. Vaccine 27:431-440

Yao F, Eriksson E (1999) A novel tetracycline-inducible viral replication switch. Hum Gene Ther 10:419-427

Yoshida Y, Hamada H (1997) Adenovirus-mediated inducible gene expression through tetracycline-controllable transactivator with nuclear localization signal. Biochem Biophys Res Commun 230:426-430

Yugawa T, Kiyono T (2009) Molecular mechanisms of cervical carcinogenesis by high-risk human papillomaviruses: novel functions of E6 and E7 oncoproteins. Rev Med Virol 19:97-113

Zwaveling S, Ferreira Mota S C, Nouta J, Johnson M, Lipford G B, Offringa R, van der Burg S H, Melief C J (2002) Established human papillomavirus type 16-expressing tumors are effectively eradicated following vaccination with long peptides. J Immunol 169:350-358

We claim:

1. A vaccine combination comprising:
   a) a first vaccine comprising an immunologically effective amount of either
   (i) a recombinant adenovirus vector comprising a first nucleic acid encoding a first polypeptide comprising the amino acid sequence of SEQ ID NO: 1 and a second nucleic acid encoding a second polypeptide comprising the amino acid sequence of SEQ ID NO: 20, or
   (ii) a first recombinant adenovirus vector comprising a first nucleic acid encoding a first polypeptide comprising the amino acid sequence of SEQ ID NO: 1 and a second recombinant adenovirus vector comprising a second nucleic acid encoding a second polypeptide comprising the amino acid sequence of SEQ ID NO: 20,
   together with a pharmaceutically acceptable carrier; and
   b) a second vaccine comprising an immunologically effective amount of a recombinant Modified Vaccinia Ankara (MVA) vector comprising a third nucleic acid encoding a third polypeptide comprising the amino acid sequence of SEQ ID NO: 1 and a fourth nucleic acid encoding a fourth polypeptide comprising SEQ ID NO: 20, together with a pharmaceutically acceptable carrier; wherein the MVA vector comprises MVA-BN or derivatives thereof.

2. The vaccine combination according to claim 1, wherein the first vaccine and the second vaccine each further comprise a nucleic acid encoding a fifth polypeptide comprising the amino acid sequence of SEQ ID NO: 28 and a nucleic acid encoding a sixth polypeptide comprising the amino acid sequence of SEQ ID NO: 31.

3. The vaccine combination according to claim 1, wherein the first polypeptide and the third polypeptide each further comprise the amino acid sequence of SEQ ID NO:28 and wherein the second polypeptide and the fourth polypeptide each further comprise the amino acid sequence of SEQ ID NO: 31.

4. A vaccine combination according to claim 1, wherein the first nucleic acid and the third nucleic acid each encode a polypeptide comprising the amino acid sequence of SEQ ID NO: 3, and wherein the second nucleic acid and the fourth nucleic acid each encode a polypeptide comprising the amino acid sequence of SEQ ID NO: 22.

5. The vaccine combination according to claim 1, wherein the first nucleic acid and the third nucleic acid each have at least 90% sequence identity to the polynucleotide sequence of SEQ ID NO: 2, and the second nucleic acid and the fourth nucleic acid each have at least 90% sequence identity to the polynucleotide sequence of SEQ ID NO: 21.

6. The vaccine combination according to claim 4, wherein the first nucleic acid and the third nucleic acid each have at least 90% sequence identity to the polynucleotide sequence of SEQ ID NO: 4 or SEQ ID NO: 24 and the second nucleic acid and the fourth nucleic acid each have at least 90% sequence identity to the polynucleotide sequence of SEQ ID NO: 23 or SEQ ID NO: 25.

7. The vaccine combination according to claim 1, wherein the recombinant adenovirus vector is rAd26.

8. The vaccine combination according to claim 1, wherein the first vaccine comprises a first recombinant adenovirus vector comprising the first nucleic acid and a second recombinant adenovirus comprising the second nucleic acid.

9. A recombinant Modified Vaccinia Ankara (MVA) vector comprising: (a) a first nucleic acid encoding at least one of a polypeptide comprising the amino acid sequence of SEQ ID NO: 1 and a polypeptide comprising the amino acid sequence of SEQ ID NO: 3, and (b) a second nucleic acid encoding at least one of a polypeptide comprising the amino acid sequence of SEQ ID NO: 20 and a polypeptide comprising the amino acid sequence of SEQ ID NO: 22;
wherein the MVA vector is MVA-BN or derivatives thereof.

10. The recombinant Modified Vaccinia Ankara (MVA) vector according to claim 9, wherein the first nucleic acid encodes the polypeptide comprising the amino acid sequence of SEQ ID NO: 1, and the second nucleic acid encodes the polypeptide comprising the amino acid sequence of SEQ ID NO: 20.

11. The recombinant MVA vector according to claim 9, wherein the first nucleic acid encodes the polypeptide comprising the amino acid sequence of SEQ ID NO: 3, and the second nucleic acid encodes the polypeptide comprising the amino acid sequence of SEQ ID NO: 22.

12. The recombinant MVA vector according to claim 10, wherein the first nucleic acid has at least 90% sequence identity to the polynucleotide sequence of SEQ ID NO: 2, and the second nucleic acid has at least 90% sequence identity to the polynucleotide sequence of SEQ ID NO: 21.

13. The recombinant MVA vector according to claim 11, wherein the first nucleic acid has at least 90% sequence identity to the polynucleotide sequence of SEQ ID NO: 4 or SEQ ID NO: 24, and the second nucleic acid has at least 90% sequence identity to the polynucleotide sequence of SEQ ID NO: 23 or SEQ ID NO: 25.

14. A recombinant MVA vector comprising at least one nucleic acid encoding at least one polypeptide selected from the group consisting of polypeptides comprising the amino acid sequences of SEQ ID NO: 1, SEQ ID NO: 3, SEQ ID NO: 20, and SEQ ID NO:22, wherein the at least one nucleic acid is operably linked to a promoter comprising at least one of the polynucleotide sequences of SEQ ID NO: 26 and SEQ ID NO: 27.

15. A vaccine comprising a recombinant MVA vector according to claim 9 and a pharmaceutically acceptable carrier.

16. A method for treating a persistent Human Papilloma Virus (HPV) infection, vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC)), oropharyngeal cancer, penile cancer, vaginal cancer or anal cancer in a subject in need thereof, the method comprising administering to the subject the vaccine combination according to claim 1.

17. A method for inducing an immune response against Human Papilloma Virus (HPV) in a subject in need thereof, the method comprising:
  (a) administering to the subject a first vaccine comprising an immunologically effective amount of either
  (i) a recombinant adenovirus vector comprising a first nucleic acid encoding a first polypeptide comprising the amino acid sequence of SEQ ID NO:1 and a second nucleic acid encoding a second polypeptide comprising SEQ ID NO: 20, or
  (ii) a first recombinant adenovirus vector comprising a first nucleic acid encoding a first polypeptide comprising the amino acid sequence of SEQ ID NO:1 and a second recombinant adenovirus vector comprising a second nucleic acid encoding a second polypeptide comprising the amino acid sequence of SEQ ID NO: 20,
  together with a pharmaceutically acceptable carrier; and
    (b) administering to the subject a second vaccine comprising an immunologically effective amount of a recombinant Modified Vaccinia Ankara (MVA) vector comprising a third nucleic acid encoding a third polypeptide comprising the amino acid sequence of SEQ ID NO:1 and a fourth nucleic acid encoding a fourth polypeptide comprising the amino acid sequence of SEQ ID NO: 20, together with a pharmaceutically acceptable carrier;
    wherein the first vaccine is administered to the subject as a priming vaccine and the second vaccine is administered to the subject as a boosting vaccine.

18. The method according to claim 17, wherein the first polypeptide and the third polypeptide each further comprise the amino acid sequence of SEQ ID NO: 28 and wherein the second polypeptide and the fourth polypeptide each further comprise the amino acid sequence of SEQ ID NO: 31.

19. The method according to claim 17, wherein the first vaccine comprises the first recombinant adenovirus vector comprising the first nucleic acid encoding the first polypeptide comprising the amino acid sequence of SEQ ID NO: 1 and the second recombinant adenovirus vector comprising the second nucleic acid encoding the second polypeptide comprising the amino acid sequence of SEQ ID NO: 20.

20. The method according to claim 17, wherein the first vaccine comprises the first recombinant adenovirus vector comprising the first nucleic acid encoding the first polypeptide comprising the amino acid sequence of SEQ ID NO: 3 and the second recombinant adenovirus vector comprising the second nucleic acid encoding the second polypeptide comprising the amino acid sequence of SEQ ID NO: 22.

* * * * *